United States Patent
Lovell et al.

(10) Patent No.: US 11,207,421 B2
(45) Date of Patent: *Dec. 28, 2021

(54) NANOSTRUCTURES COMPRISING COBALT PORPHYRIN-PHOSPHOLIPID CONJUGATES AND POLYHISTIDINE-TAGS

(71) Applicants: The Research Foundation for The State University of New York, Buffalo, NY (US); PATH, Seattle, WA (US)

(72) Inventors: Jonathan Lovell, Niagara Falls (CA); Shuai Shao, Tonawanda, NY (US); Jumin Geng, Williamsville, NY (US); Wei-Chiao Huang, Amherst, NY (US); Shwu-Maan Lee, Rockville, MD (US); Charles Richter King, Washington, DC (US)

(73) Assignees: The Research Foundation for The State University of New York, Amherst, NY (US); PATH, Seattle, WA (US)

(*) Notice: Subject to any disclaimer, the term of this patent is extended or adjusted under 35 U.S.C. 154(b) by 83 days.

This patent is subject to a terminal disclaimer.

(21) Appl. No.: 16/399,581

(22) Filed: Apr. 30, 2019

(65) Prior Publication Data
US 2019/0255188 A1    Aug. 22, 2019

Related U.S. Application Data

(63) Continuation-in-part of application No. 15/566,140, filed as application No. PCT/US2016/028102 on Apr. 18, 2016, now Pat. No. 10,272,160.

(60) Provisional application No. 62/148,292, filed on Apr. 16, 2015.

(51) Int. Cl.
| | |
|---|---|
| *A61K 39/395* | (2006.01) |
| *A61K 47/69* | (2017.01) |
| *A61K 39/145* | (2006.01) |
| *A61K 39/155* | (2006.01) |
| *A61K 39/02* | (2006.01) |
| *C12N 7/00* | (2006.01) |
| *A61P 31/04* | (2006.01) |
| *A61P 31/14* | (2006.01) |
| *A61P 31/16* | (2006.01) |
| *A61K 9/127* | (2006.01) |
| *A61K 39/00* | (2006.01) |

(52) U.S. Cl.
CPC ........ *A61K 47/6911* (2017.08); *A61K 9/1271* (2013.01); *A61K 39/02* (2013.01); *A61K 39/145* (2013.01); *A61K 39/155* (2013.01); *A61K 47/6929* (2017.08); *A61P 31/04* (2018.01); *A61P 31/14* (2018.01); *A61P 31/16* (2018.01); *C12N 7/00* (2013.01); *A61K 2039/552* (2013.01); *A61K 2039/55505* (2013.01); *A61K 2039/6018* (2013.01); *A61K 2039/64* (2013.01); *C12N 2760/16034* (2013.01); *C12N 2760/16071* (2013.01); *C12N 2760/18534* (2013.01); *C12N 2760/18571* (2013.01)

(58) Field of Classification Search
None
See application file for complete search history.

(56) References Cited

U.S. PATENT DOCUMENTS

| | | | |
|---|---|---|---|
| 10,272,160 B2 * | 4/2019 | Lovell | B82Y 5/00 |
| 2004/0258745 A1 | 12/2004 | Kai et al. | |
| 2005/0008687 A1 | 1/2005 | Yuasa et al. | |
| 2006/0166861 A1 | 7/2006 | Kida et al. | |
| 2007/0026057 A1 | 2/2007 | Altin et al. | |
| 2012/0253191 A1 | 10/2012 | Zheng et al. | |
| 2018/0085473 A1 | 3/2018 | Lovell et al. | |

FOREIGN PATENT DOCUMENTS

| | | |
|---|---|---|
| CN | 1279718 A | 1/2001 |
| CN | 101323454 A | 12/2008 |
| WO | 2018/170260 A1 | 9/2018 |

OTHER PUBLICATIONS

Cagdas, M., et al., Chapter 1: Liposomes as Potential Drug Carrier Systems for Drug Delivery, Application of Nanotechnology in Drug Delivery, Jul. 25, 2014, pp. 1-50.

Chikh, G.G.,et al., Attaching histidine-tagged peptides and proteins to lipid-based carriers through use of metal-ion-chelating lipids, Biochimica et Biophysica Acta., Dec. 23, 2002, vol. 1567, pp. 204-212.

Masek, J., et al., Immobilization of histidine-tagged proteins on monodisperse metalochelation liposomes: Preparation and stud of their structure, Analytical Biochemistry, Aug. 21, 2010, vol. 408, pp. 95-104.

Mura, S., et al., Stimuli-responsive nanocarriers for drug delivery, Nature Materials, Oct. 23, 2013, vol. 12, pp. 991-1003.

Shao, S., et al., Functionalization of Cobalt Porphyrin-Phospholipid Bilayers with His-Tagged Ligands and Antigens, Nat Chem., Apr. 20, 2015, vol. 7, pp. 1-20.

Biesaga et al., Porphyrins in analytical chemistry. A review, Talanta, Feb. 7, 2000, vol. 51, No. 2, pp. 209-224.

(Continued)

*Primary Examiner* — Yunsoo Kim
(74) *Attorney, Agent, or Firm* — Hodgson Russ LLP

(57) ABSTRACT

The present disclosure provides nanostructures (e.g., monolayer or bilayer nanostructures) comprising porphyrins with cobalt chelated thereto such that the cobalt metal resides within monolayer or bilayer in the porphyrin macrocycle. The nanostructures can have presentation molecules comprising epitopes from microorganisms with a histidine tag attached thereto, such that at least a part of the his-tag is within the monolayer or bilayer and coordinated to the cobalt metal core and the presentation molecules are exposed to the outside of the nanostructures. The nanostructures can further comprise a cargo. The nanostructures can be used to deliver the cargo to an individual.

21 Claims, 25 Drawing Sheets
Specification includes a Sequence Listing.

(56) References Cited

OTHER PUBLICATIONS

Carter et al., Porphyrin-phopholipid liposomes permeabilized by near-infrared light, Nature Communications, Apr. 3, 2014, vol. 5, No. 1, pp. 1-11.

* cited by examiner

```
                              SEQUENCE LISTING

<160> NUMBER OF SEQ ID NOS: 15

<210> SEQ ID NO 1
<211> LENGTH: 20
<212> TYPE: PRT
<213> ORGANISM: Artificial Sequence
<220> FEATURE:
<223> OTHER INFORMATION: fluorescent reporter peptide

<400> SEQUENCE: 1

Gly Arg Gly Asp Ser Pro Lys Gly Ala Gly Ala Lys Gly His His His
1               5                   10                  15

His His His His
            20

<210> SEQ ID NO 2
<211> LENGTH: 7
<212> TYPE: PRT
<213> ORGANISM: Artificial Sequence
<220> FEATURE:
<223> OTHER INFORMATION: RGD peptide

<400> SEQUENCE: 2

Gly Arg Gly Asp Ser Pro Lys
1               5

<210> SEQ ID NO 3
<211> LENGTH: 13
<212> TYPE: PRT
<213> ORGANISM: Artificial Sequence
<220> FEATURE:
<223> OTHER INFORMATION: fluorescent reporter peptide

<400> SEQUENCE: 3

Gly Arg Gly Asp Ser Pro Lys Gly Ala Gly Ala Lys Gly
1               5                   10

<210> SEQ ID NO 4
<211> LENGTH: 11
<212> TYPE: PRT
<213> ORGANISM: Artificial Sequence
<220> FEATURE:
<223> OTHER INFORMATION: his-tagged peptide

<400> SEQUENCE: 4

Arg Gly Asp Tyr His His His His His His His
1               5                   10

<210> SEQ ID NO 5
<211> LENGTH: 6
<212> TYPE: PRT
<213> ORGANISM: Artificial Sequence
<220> FEATURE:
<223> OTHER INFORMATION: fluorescent reporter peptide

<400> SEQUENCE: 5

Lys Lys Gly Gly Gly Gly
1               5
```

```
<210> SEQ ID NO 6
<211> LENGTH: 8
<212> TYPE: PRT
<213> ORGANISM: Artificial Sequence
<220> FEATURE:
<223> OTHER INFORMATION: fluorescent reporter peptide

<400> SEQUENCE: 6

Lys Lys Gly Gly Gly Gly His His
1               5

<210> SEQ ID NO 7
<211> LENGTH: 10
<212> TYPE: PRT
<213> ORGANISM: Artificial Sequence
<220> FEATURE:
<223> OTHER INFORMATION: fluorescent reporter peptide

<400> SEQUENCE: 7

Lys Lys Gly Gly Gly Gly His His His His
1               5                   10

<210> SEQ ID NO 8
<211> LENGTH: 12
<212> TYPE: PRT
<213> ORGANISM: Artificial Sequence
<220> FEATURE:
<223> OTHER INFORMATION: fluorescent reporter peptide

<400> SEQUENCE: 8

Lys Lys Gly Gly Gly Gly His His His His His His
1               5                   10

<210> SEQ ID NO 9
<211> LENGTH: 14
<212> TYPE: PRT
<213> ORGANISM: Artificial Sequence
<220> FEATURE:
<223> OTHER INFORMATION: fluorescent reporter peptide

<400> SEQUENCE: 9

Lys Lys Gly Gly Gly Gly His His His His His His His His
1               5                   10

<210> SEQ ID NO 10
<211> LENGTH: 16
<212> TYPE: PRT
<213> ORGANISM: Artificial Sequence
<220> FEATURE:
<223> OTHER INFORMATION: fluorescent reporter peptide

<400> SEQUENCE: 10

Lys Lys Gly Gly Gly Gly His His His His His His His His His His
1               5                   10                  15

<210> SEQ ID NO 11
<211> LENGTH: 28
<212> TYPE: PRT
<213> ORGANISM: Artificial Sequence
<220> FEATURE:
<223> OTHER INFORMATION: MPER peptide

<400> SEQUENCE: 11

Asn Glu Gln Glu Leu Leu Glu Leu Asp Lys Trp Ala Ser Leu Trp Asn
1               5                   10                  15

Gly Gly Lys Gly Gly His His His His His His
            20                  25
```

```
<210> SEQ ID NO 12
<211> LENGTH: 19
<212> TYPE: PRT
<213> ORGANISM: Artificial Sequence
<220> FEATURE:
<223> OTHER INFORMATION: MPER peptide

<400> SEQUENCE: 12

Asn Glu Gln Glu Leu Leu Glu Leu Asp Lys Trp Ala Ser Leu Trp Asn
1               5                   10                  15

Gly Gly Lys

<210> SEQ ID NO 13
<211> LENGTH: 20
<212> TYPE: PRT
<213> ORGANISM: Artificial Sequence
<220> FEATURE:
<223> OTHER INFORMATION: cell penetrating peptide

<400> SEQUENCE: 13

His His His His His His His Gly Arg Lys Lys Arg Arg Gln Arg Arg
1               5                   10                  15

Arg Pro Pro Gln
            20

<210> SEQ ID NO 14
<211> LENGTH: 15
<212> TYPE: PRT
<213> ORGANISM: Artificial Sequence
<220> FEATURE:
<223> OTHER INFORMATION: cell penetrating peptide

<400> SEQUENCE: 14

His His His His His His His Arg Arg Arg Arg Arg Arg Arg Arg
1               5                   10                  15

<210> SEQ ID NO 15
<211> LENGTH: 23
<212> TYPE: PRT
<213> ORGANISM: Artificial Sequence
<220> FEATURE:
<223> OTHER INFORMATION: cell penetrating peptide

<400> SEQUENCE: 15

His His His His His His His Arg Gln Ile Lys Ile Trp Phe Gln Asn
1               5                   10                  15

Arg Arg Met Lys Trp Lys Lys
            20
```

NANOSTRUCTURES COMPRISING COBALT PORPHYRIN-PHOSPHOLIPID CONJUGATES AND POLYHISTIDINE-TAGS

CROSS-REFERENCE TO RELATED APPLICATIONS

This application is a continuation-in-part of U.S. patent application Ser. No. 15/566,140, filed on Oct. 12, 2017, which is the national stage entry of International application no. PCT/US2016/028102, filed on Apr. 18, 2016, which claims priority to U.S. Provisional patent application No. 62/148,292, filed on Apr. 16, 2015, the disclosures of which are incorporated herein by reference.

STATEMENT REGARDING FEDERALLY SPONSORED RESEARCH

This invention was made with government support under grant numbers DP5OD017898 and R21AI122964 awarded by the National Institutes of Health. The government has certain rights in the invention.

FIELD OF THE DISCLOSURE

This disclosure relates general to the field of functionalized nanostructures. More particularly, the disclosure relates to nanostructures comprising cobalt-porphyrin.

BACKGROUND OF THE DISCLOSURE

In the field of functionalized nanoparticles one of the challenges is to easily and reliably attach peptides and proteins to larger scaffolds. Targeted nanoparticles require effective ligands and unconjugated peptides themselves are weakly immunogenic. Bioconjugate chemistry has provided a range of strategies, but most nanoparticulate conjugations suffer from limitations relating to one or more of the following: 1) low conjugation yields and necessitated purification steps; 2) incompatibility with biological buffers, making labeling of intact nanoparticles impossible; 3) variable labeling sites and conjugated polypeptide conformations, creating an inhomogeneous particle population of varying efficacy; 4) necessity for complex and exogenous chemical approaches.

Standard approaches for ligand attachment to aqueous nanoparticles make use of maleimides, succinimidyl esters and carbodiimide-activated carboxylic acids. These can covalently react with amine and thiol groups of polypeptides. The use of maleimide-lipids has been explored extensively for antibody-conjugated immunoliposomes. Conjugation yields may reach as high as 90% from an overnight reaction, but subsequent quenching of free maleimide groups and additional purification is required. Proteins may require a preparative step of thiolation and purification prior to conjugation. Antibody orientation is a major factor influencing the conjugated antibody target binding efficacy, but these approaches result in numerous antibody labeling sites and indiscriminate orientations. Biorthogonal synthetic strategies such as the click reaction have recently been applied to pre-formed liposomes, however these require the use exogenous catalysts and unconventional amino acids.

Another approach that is suitable for smaller peptides which are less prone to permanent denaturation in organic solvents is to conjugate the peptides to a lipid anchor. The resulting lipopeptides can then be incorporated along with the other lipids during the liposome formation process. This approach has been used to generate synthetic vaccines that induce antibody production against otherwise non-immunogenic peptides. However, due to their amphipathic character, in that case the lipopeptides were difficult to purify, with a yield of 5-10%. It has also been shown that lipopeptides do not fully incorporate into liposomes during the formation process, resulting in aggregation.

SUMMARY OF THE DISCLOSURE

The present disclosure provides functionalized nanostructures. The nanostructures can be used for delivery of cargo, targeted delivery and/or delivery of presentation molecules. The nanostructures can be monolayers or bilayers which enclose an aqueous compartment therein. Bilayer structures enclosing an aqueous compartment are referred to herein as liposomes. The nanostructures can be monolayer or bilayer coating on a nanoparticle. The monolayer or bilayer comprises cobalt porphyrin-phospholipid conjugate, optionally phospholipids that are not conjugated to porphyrin, optionally sterols, and optionally polyethylene glycol (PEG). One or more targeting peptides or polypeptides (referred to herein as presentation molecules) having a polyhistidine tag are incorporated into the monolayer or bilayer such that a portion of the polyhistidine tag resides in the monolayer or bilayer and the presentation molecule is exposed to the exterior of the monolayer or bilayer. Instead of, or in addition to the cobalt porphyrin phospholipid conjugate, cobalt porphyrin can be used.

The nanostructures of the present disclosure can be loaded with cargo for delivery to sites that can be targeted by the polyhistidine tagged presentation molecules. For example, liposomes can be loaded with cargo for delivery to desired sites by using polyhistidine tagged presentation molecules.

Data presented here demonstrates that a bilayer containing a cobalt-porphyrin, such as a cobalt porphyrin-phospholipid (CoPoP) can stably bind polyhistidine-tagged (also referred to herein as "his-tagged") polypeptides (FIG. 1a). Other metallo-porphyrins such as zinc, nickel, and copper are not able to stably bind a his-tagged polypeptide. This represents a new binding paradigm, with at least some polyhistidines buried in the membrane phase, as the porphyrins themselves form the hydrophobic portion of the bilayer and are not accessible to the external aqueous environment (FIG. 1b). This leads to more stable binding, allows for significantly simpler non-covalent post-labeling paradigms following nanoparticle formation, and eliminates ambiguity regarding ligand orientation.

We show that lipid bilayers containing porphyin-phospholipid which is chelated with cobalt, but not other metals, can effectively capture his-tagged proteins and peptides. The binding follows a Co(II) to Co(III) transition and occurs within the sheltered hydrophobic bilayer, resulting in, for example, essentially irreversible attachment in serum or in million-fold excess of competing imidazole. Using this approach we inserted homing peptides into the bilayer of pre-formed empty and cargo-loaded liposomes to enable site targeting (such as tumor-targeting) without disrupting the bilayer integrity. Peptides or synthetic peptide can be bound to liposomes containing an adjuvant (such as the lipid monophosphoryl lipid A) for antibody generation for an otherwise non-antigenic peptides.

The present disclosure provides monolayer or bilayer structures, wherein the monolayer or bilayer comprises porphyrins with cobalt chelated thereto such that the cobalt metal resides within monolayer or bilayer and the porphyrin macrocycle and further has molecules with a histidine tag non-covalently attached thereto, such that at least a part of the his-tag is within the monolayer or bilayer and coordinated to the cobalt metal core. The presentation molecules can be used for various applications including targeting and generation of immune responses. Liposomes or micelles formed by the present layers may be loaded with cargo for release at desired locations. The cobalt porphyrin maybe be cobalt porphyrin-phospholipid (CoPoP). The present layers may also be used as coatings for other nanostructures including metal nanoparticles, nanotubes and the like.

DESCRIPTION OF THE DISCLOSURE

Figure 1:
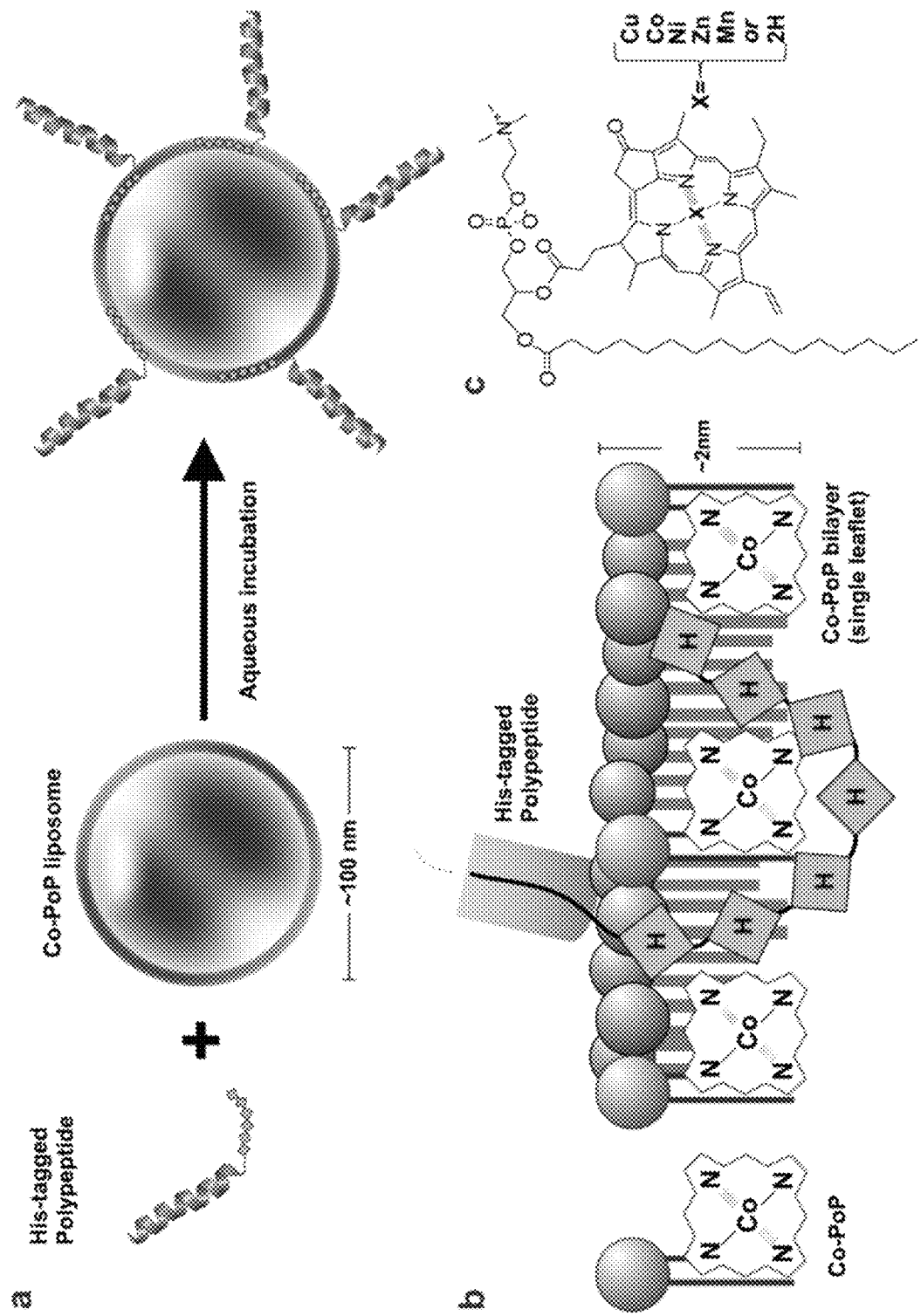
FIG. 1. His-tag binding to PoP-bilayers. (a) Schematic showing a peptide with a His-tag (green) binding to preformed CoPoP liposomes in aqueous solution. (b) Insertion of a His-tagged polypeptide into a bilayer containing CoPoP. Only a single leaflet of the bilayer is shown. (c) Chemical structure of metallo-PoPs used in this study.

The present disclosure provides nanostructures comprising at least a monolayer. For example, the structures can comprise a monolayer or a bilayer wherein the monolayer or bilayer comprise porphyrin-phospholipid conjugates that have cobalt chelated thereto such that the cobalt resides within the bilayer. The bilayer structures can form liposomes. The structures can comprise two monolayers (bilayers), where the hydrophobic groups of the two monolayers are opposed and the hydrophilic groups are exposed to the surface.

The disclosure herein regarding bilayers is also applicable to monolayers. The bilayers or monolayers are sometimes referred to herein as "membranes".

All ranges provided herein include all values that fall within the ranges to the tenth decimal place, unless indicated otherwise.

Some or all of the cobalt porphyrins in the monolayer or bilayer can non-covalently bind polyhistidine-tagged molecules, such that at least part of the polyhistidine tag resides within the bilayer and the tagged molecule is presented on the surface of the bilayer. In the present bilayers or monolayers, it is considered that one or more histidine residues in the polyhistidine tag are coordinated to the cobalt metal core within the bilayer, thereby providing stability to the structure. The histidine residues of a polyhistidine tag may be coordinated to the cobalt metal in the core of the porphyrin in the membrane. The entire histidine tag may reside within the bilayer. A porphyrin phospholipid conjugate which has cobalt metal conjugated thereto is referred to herein as CoPoP. Liposomes wherein the bilayer comprises CoPoP are referred to herein as CoPoP liposomes. The CoPoP liposomes can be functionalized with histidine tagged molecules. The term "his-tagged molecules" as used herein means molecules—such as, for example, peptides, polypeptides, or proteins—which have a histidine tail. For example a peptide with a histidine tail is a his-tagged molecule. Such his-tag containing CoPoP liposomes are referred to herein as his-tagged CoPoP liposomes or his-tagged CoPoP.

The CoPoP monolayers or bilayers functionalized with his-tagged presentation molecules of the present disclosure provide a platform for presentation of various molecules of interest in the circulation or for delivery to desired locations or for generation of specific immune responses to those his-tagged molecules. These molecules are referred to herein as presentation molecules (PMs). Structures containing his-tagged CoPoP bilayers, which have PMs attached to the histidine tag exhibit desirable stability. The his-tagged molecules are non-covalently attached to (coordinated to) the CoPoP and can be prepared by an incubation process. Therefore, the process does not need removal of reactive moieties—such as maleimide and the like—or exogenous catalysts or non-natural amino acids that are used in other types of conjugation chemistries.

The cobalt-porphyrin may be in a bilayer in self-assembling liposomes enclosing therewithin an aqueous compartment. Alternatively, it may be in a single layer or bilayer coating that coats other nanoparticles. Cobalt-porphyrin phospholipid (CoPoP) behaves like a conventional lipid with respect to its amphipathic nature. Therefore, monolayers or bilayers comprising CoPoP can be used for coating of nanoparticles by methods that are known to those skilled in the art. In one embodiment, the bilayer or monolayer of the present disclosure may be present on other nanoparticles, such as, for example, in the form of a coating. In one embodiment, the bilayer or monolayer containing cobalt-porphyrin (e.g., cobalt porphyrin-phospholipid) is present as a coating on gold or silica nanoparticles, or other nanoparticles with a hydrophilic surface. In one embodiment, the coating may be in the form of monolayers. In one embodiment the monolayer or bilayer containing cobalt-porphyrin (e.g., cobalt porphyrin-phospholipid) is present as a coating on hydrophobic surfaces such as carbon nanotubes. In one embodiment, the monolayers may form micelles surrounding one or more hydrophobic molecules.

This disclosure provides a nanostructure comprising a monolayer or a bilayer, wherein the monolayer or bilayer comprises: i) optionally, phospholipids and ii) porphyrin which has cobalt coordinated thereto forming cobalt-porphyrin. Optionally, the nanostructure also has one or more polyhistidine-tagged presentation molecule. At least a portion of the polyhistidine tag resides in the hydrophobic portion of the monolayer or the bilayer and one or more histidines of the polyhistidine tag are coordinated to the cobalt in the cobalt-porphyrin. At least a portion of the polyhistidine-tagged presentation molecule is exposed to the outside of the nanostructure. The nanostructure can be in the form of a liposome that encloses an aqueous compartment. However, the nanostructure may also coat a hydrophilic or hydrophobic material such as a gold or silica nanoparticle. The cobalt porphyrin may be conjugated to a phospholipid to form a cobalt porphyrin-phospholipid conjugate. The cobalt porphyrin can make up from 1 to 100 mol % of the monolayer or the bilayer, including 0.1 mol % values and ranges therebetween. For example, the cobalt porphyrin can make up from 1 to 20 mole %, or from 5 to 10 mol % of the monolayer or the bilayer. If the cobalt porphyrin makes up 100% of the monolayer or the bilayer, then there are no phospholipids present that are not conjugated to cobalt porphyrin. The bilayer or the monolayer can also comprise sterol and/or polyethylene glycol. The sterol can be cholesterol.

The number of histidines in the polyhistidine-tag in the monolayer or bilayer can be from 2 to 20. For example, the number of histidines in the polyhistidine-tag can be from 6 to 10. For example, the number of histidines can be 3, 4, 5, 6, 7, 8, 9, 10, 11, 12, 13, 14, 15, 16, 17, 18, 19, or 20.

The liposomes may be spherical or non-spherical. The size of the liposomes can be from 50 to 1000 nm or more. In one embodiment, the liposomes have a size (e.g., a longest dimension such as, for example, a diameter) of 50 to 1000 nm, including all integer nm values and ranges therebetween. For example, the size may be from 50 to 200 nm or from 20 to 1000 nm. If the liposomes are not spherical, the longest dimension can be from 50 to 1000 nm. These dimensions can be achieved while preserving the nanostructure width of the monolayer of the bilayer. The liposomes can carry cargo in the aqueous compartment. The cargo, or part thereof, can also, or alternatively, be incorporated in the monolayer or the bilayer.

In one embodiment, this disclosure provides a liposome comprising: a monolayer or a bilayer, wherein the monolayer or bilayer comprises cobalt-porphyrin phospholipid conjugate, optionally phospholipids that are not conjugated to cobalt porphyrin, and a polyhistidine-tagged presentation molecule, wherein at least a portion of the polyhistidine tag resides in the hydrophobic portion of the monolayer or the bilayer and one or more histidines of the polyhistidine tag are coordinated to the cobalt in the cobalt-porphyrin phospholipid conjugates. At least a portion of the polyhistidine-tagged presentation molecule is exposed to the outside of the nanostructure. The nanostructure, such as a liposome, can enclose an aqueous compartment. The monolayer or the bilayer need not contain any phospholipids that are not conjugated to cobalt porphyrin and in this case only has cobalt porphyrin phospholipid conjugates. Cargo can be present in the aqueous compartment. The cargo need not reside exclusive in the aqueous compartment and a part thereof can reside in the monolayer or the bilayer.

The disclosure also provides a monolayer or a bilayer, wherein the monolayer or bilayer comprises phospholipid monomers and porphyrin having cobalt coordinated thereto (forming cobalt-porphyrin). The monolayer or the bilayer has associated therewith one or more polyhistidine-tagged presentation molecules, wherein at least a portion of the polyhistidine tag resides in the hydrophobic portion of the monolayer or the bilayer. One or more histidines of the polyhistidine tag are coordinated to the cobalt in the cobalt-porphyrin and at least a portion of the polyhistidine-tagged presentation molecule is outside of the bilayer or the monolayer. In various examples, the monolayer or the bilayer encloses an aqueous compartment or forms a coating on a nanoparticle—such as a gold or silica nanoparticle.

The disclosure provides a nanostructure comprising a core, and a monolayer or a bilayer coating on the core, wherein the monolayer or bilayer comprises phospholipids, and porphyrin having cobalt coordinated thereto forming cobalt-porphyrin. The nanostructure can have one or more polyhistidine-tagged presentation molecules, wherein at least a portion of the polyhistidine tag resides in the hydrophobic portion of the monolayer or the bilayer and one or more histidines of the polyhistidine tag are coordinated to the cobalt in the cobalt-porphyrin. At least a portion of the polyhistidine-tagged presentation molecule is exposed to the outside of the nanoparticle. The core of the nanostructure can be a nanoparticle such as a gold or silica nanoparticle.

The liposomes, or nanoparticles having a coating or monolayer or bilayer, as described herein can have presentation molecules thereon, which can be antigenic molecules and/or targeting molecules. The presentation molecules can also provide targeting ability and/or imaging or other functionalities.

Liposomes or other nanostructures comprising his-tagged polypeptides and CoPoP compositions exhibit high serum-stability with respect to binding of the his-tagged polypeptide to the liposome. In one embodiment, when incubated with serum (such as diluted serum) at room temperature, more than 60% of the his-tagged peptide remains bound to the CoPoP-containing bilayer after 24 hours incubation. In one embodiment, more than 85% of the his-tagged peptide remains bound to the CoPoP layer after incubation with serum for 24 hours.

The CoPoP liposomes or the his-tagged CoPoP liposomes can be loaded with cargo—which typically resides in the aqueous compartment, but may reside entirely or partially embedded in the bilayer—if it is hydrophobic or has a hydrophobic component. In addition to having presentation molecules on the surface, these structures can be used to load cargo in the aqueous compartment within the structures, or in the bilayer. The release of cargo from the CoPoP-liposomes can be triggered by near infrared (NIR) light. The cargo can be released at desired locations—such as by being internalized in targeted cells or by light triggered release.

The cobalt-porphyrin of the monolayers or bilayers is a porphyrin having a cobalt (Co) cation conjugated to the porphyrin. The porphyrin can be conjugated to a phospholipid (referred to herein as a cobalt porphyrin-phospholipid or cobalt porphyrin-phospholipid conjugate).

The porphyrin portion of the cobalt-porphyrin or cobalt-porphyrin conjugate making at least part of some of the bilayer of the liposomes or other structures comprise porphyrins, porphyrin derivatives, porphyrin analogs, or combinations thereof. Exemplary porphyrins include hematoporphyrin, protoporphyrin, and tetraphenylporphyrin. Exemplary porphyrin derivatives include pyropheophorbides, bacteriochlorophylls, Chlorophyll A, benzoporphyrin derivatives, tetrahydroxyphenyl chlorins, purpurins, benzochlorins, naphthochlorins, verdins, rhodins, keto chlorins, azachlorins, bacteriochlorins, tolyporphyrins, and benzobacteriochlorins. Exemplary porphyrin analogs include expanded porphyrin family members (such as texaphyrins, sapphyrins and hexaphyrins) and porphyrin isomers (such as porphycenes, inverted porphyrins, phthalocyanines, and naphthalocyanines). For example, the cobalt-porphyrin can be a vitamin $B_{12}$ (cobalamin) or derivative.

In one embodiment, the PoP is pyropheophorbide-phospholipid. The structure of pyropheophorbide-phospholipid is shown below:

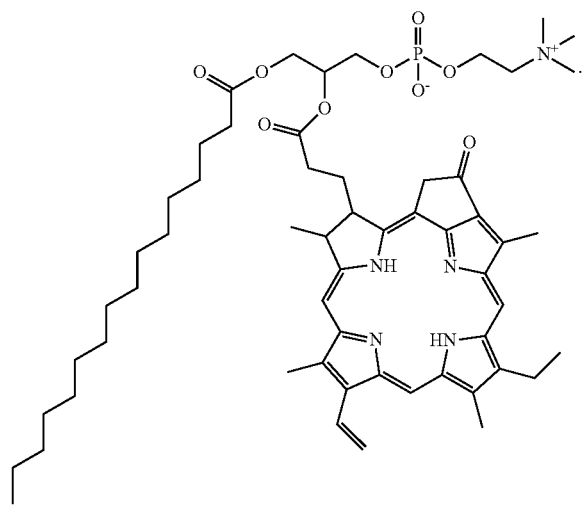 [SMILES: C=CC1=C(C)c2cc3[nH]c(c4c5nc(cc6[nH]c(cc1n2)c(C)c6CC)C(C)=C5C(=O)C4)C(CCC(=O)OC(COC(=O)CCCCCCCCCCCCCCC)COP(=O)([O-])OCC[N+](C)(C)C)C3C]

In one embodiment, the layer (monolayer or bilayer) has only CoPoP which has his-tagged presentation molecules embedded therein. In this embodiment, the only phospholipid in the layer is CoPoP (i.e., CoPoP is 100 mol %). In one embodiment, the layer (monolayer or bilayer) has only CoPoP and porphyrin conjugated phospholipids (PoP), wherein CoPoP has histidines embedded therein, with the histidines having a peptide or other presentation molecules attached thereto. In certain embodiments, there are no other phospholipids, but the layer (monolayer or bilayer) may optionally contain sterols and/or PEG-lipid.

In one embodiment, in addition to the CoPoP, the bilayer or monolayer also has phospholipids which are not conjugated to porphyrin and therefore, not coordinated with Co. Such phospholipids may be referred to herein as "additional phospholipids". The bilayer or monolayer may also comprise sterol and PEG-lipid. In one embodiment, the bilayer or monolayer consists essentially of, or consists of CoPoP, phospholipids that are not conjugated to porphyrins, and optionally sterol and/or PEG, wherein the PEG may be conjugated to lipid. In one embodiment, the only metal-PoP in the bilayer is CoPoP, which has his-tagged presentation molecules embedded therein. In one embodiment, the only metal in the bilayer is Co.

In one embodiment, the bilayer of the liposomes comprises CoPoP and PoP. In addition to the CoPoP and the PoP, the bilayer can have additional phospholipids. The bilayer or monolayer may further comprise sterol and/or PEG. The PEG may be conjugated to lipid. In one embodiment, the bilayer consists essentially of, or consists of CoPoP, PoP, additional phospholipids, and optionally sterol and/or PEG, wherein the PEG may be conjugated to lipid. In one embodiment, the only metal-PoP in the bilayer is CoPoP. In one embodiment, the only metal in the bilayer is Co.

In one embodiment, the CoPoP is present in the nanoparticles from 0.1 to 10 mol % with the remainder 99.9 to 90 mol % being made up by additional lipids, with the percent being of the entire bilayer lipids. For example, the combination of CoPoP can be present from 0.1 to 10 mol %, sterol can be present from 0.1 to 50 mol %, optionally, attenuated lipid A derivatives such as monophosphoryl lipid A or 3-deacylated monophosphoryl lipid A or a related analog can be present from 0 to 20 mol % or 0.1 to 20 mol %, and the remainder can be made up by additional phospholipids. The phospholipids are DOPC, DSPC, DMPC or combinations thereof, and sterol, if present, can be cholesterol.

In one embodiment, the combination of CoPoP and PoP may be present in the nanoparticles from 0.1 to 10 mol % with the remaining 99.9 to 90 mol % being made up by additional phospholipids. For example, the combination of CoPoP and PoP can be present from 0.1 to 10 mol %, sterol can be present from 0 to 50 mol % or 0.1 to 50 mol %, optionally PEG can be present from 0 to 20 mol % or 0.1 to 20 mol %, and the remainder can be made up by phospholipids. The phospholipids can be DOPC, DSPC, DMPC or combinations thereof and sterol, if present, can be cholesterol.

As used herein, "phospholipid" is a lipid having a hydrophilic head group having a phosphate group connected via a glycerol backbone to a hydrophobic lipid tail. The phospholipid comprises an acyl side chain of 6 to 22 carbons, including all integer number of carbons and ranges therebetween. In certain embodiments, the phospholipid in the porphyrin conjugate is 1-palmitoyl-2-hydroxy-sn-glycero-3-phosphocholine. The phospholipid of the porphyrin conjugate may comprise, or consist essentially of phosphatidylcholine, phosphatidylethanoloamine, phosphatidylserine and/or phosphatidylinositol.

In certain embodiments, the porphyrin is conjugated to the glycerol group on the phospholipid by a carbon chain linker of 1 to 20 carbons, including all integer number of carbons therebetween.

In various embodiments, in addition to the porphyrin conjugates disclosed herein, the bilayer of the liposomes also comprises other phospholipids. The fatty acid chains of these phospholipids may contain a suitable number of carbon atoms to form a bilayer. For example, the fatty acid chain may contain 12, 14, 16, 18 or 20 carbon atoms. In different embodiments the bilayer comprises phosphatidylcholine, phosphatidylethanoloamine, phosphatidylserine and/or phosphatidylinositol.

The present bilayers and monolayers may also comprise sterols. The sterols may be animal sterols or plant sterols. Examples of sterols include cholesterol, sitosterol, stigmasterol, and cholesterol. In embodiments, cholesterol may be from 0 mol % to 50 mol %, or 0.1 to 50 mol %. In other embodiments, cholesterol may be present from 1 to 50 mol %, 5 to 45 mol %, 10 to 30 mol %.

In certain embodiments, the bilayer or monolayer further comprises PEG-lipid. The PEG-lipid can be DSPE-PEG such as DSPE-PEG-2000, DSPE-PEG-5000 or other sizes of DSPE-PEG. The PEG-lipid is present in an amount of 0 to 20 mol % including all percentage amounts therebetween to the tenth decimal point. The average molecular weight of the PEG moiety can be between 500 and 5000 Daltons and all integer values and ranges therebetween.

In certain embodiments, the bilayer or monolayer further comprises an adjuvant such as attenuated lipid A derivatives such as monophosphoryl lipid A or 3-deacylated monophosphoryl lipid A.

The histidine tag (his-tag) may carry a variety of presentation molecules of interest for various applications. At least one or both ends of the his-tag can reside close to the outer surface of the liposome. In one embodiment, at least one end of the polyhistidine tag is covalently attached to a presentation molecule. In one embodiment, the his-tag is a string of at least 2 histidines. In one embodiment, the his-tag is a string of 2-20 histidines. In one embodiment, the his-tag is a string of from 4-12 histidines and all integer numbers therebetween. In one embodiment, it is from 6-10 histidines. In one embodiment, it is 6, 7, 8, 9 or 10 histidines. In one embodiment, one end of the his-tag is free and a peptide or other molecule is attached to the other end. It is considered that at least a part of the his-tag is located within the bilayer such that it is coordinated with the cobalt metal core.

The liposomes of the present disclosure (without the his-tagged molecules) can be substantially spherical and have a size (e.g., a longest dimension such as, for example, a diameter) of 30 nm to 250 nm, including all integers to the nm and ranges therebetween. In one embodiment, the size of the liposomes is from 100-175 nm. In one embodiment, at least 50%, 60%, 70%, 80%, 85%, 90%, 95%, 99%, or 100% of the liposomes in the composition have a size of from 30 to 250 nm or from 100 to 175 nm. The liposomes or nanostructures can be more than 200 nm. In one embodiment, the nanostructures are more than 1000 nm. In one embodiment, the nanostructures are from 200 to 1000 nm. The liposomes or nanostructures may be spherical or non-spherical. In one embodiment, the largest dimensions of the nanostructure are less than 200 nm, while preserving the nanostructure width of the monolayer or bilayer. In one embodiment, the size of the nanostructure exceed 200 nm in some dimensions, while preserving the nanostructure width of the monolayer or bilayer. In one embodiment, the size of the nanostructure exceed 1000 nm in some dimensions, while preserving the nanostructure width of the monolayer or bilayer.

In one aspect, the disclosure provides a composition comprising liposomes or other structures of the present disclosure or a mixture of different liposomes or other structures. The compositions can also comprise a sterile, suitable carrier for administration to individuals including humans, such as, for example, a physiological buffer such as sucrose, dextrose, saline, pH buffering (such as from pH 5 to 9, from pH 7 to 8, from pH 7.2 to 7.6, (e.g., 7.4)) element such as histidine, citrate, or phosphate. In one embodiment, the composition comprises at least 0.1% (w/v) CoPoP liposomes or his-tagged-CoPoP liposomes or other structures. In various embodiments, the composition comprises from 0.1 to 100 mol % CoPoP liposomes or his-tagged CoPoP liposomes or other structures such as bilayer coated nanoparticles. In one embodiment, the composition comprises from 0.1 to 99 mol % CoPoP liposomes having his-tagged presentation molecules associated therewith.

In one embodiment, the compositions of the present disclosure are free of maleimide or succinimidyl ester reactive groups. In one embodiment, the tagged molecule to be attached to the membrane does not have a non-natural amino acid.

The presentation molecule bearing the his-tag may be a small molecule or a macromolecule. In one embodiment, the molecule is a peptide or a peptide derivative. In one embodiment, the molecule is a polypeptide, polynucleotide, carbohydrate or polymer. The his-tag may be chemically conjugated to the molecule of interest. The his-tag may be incorporated into the primary amino acid sequence of a polypeptide. In one embodiment, the molecule is an antigen, such as a peptide (2-50 amino acids and all peptides of amino acid lengths between 2 and 50) or a polypeptide (50-1,000 amino acids and all polypeptides of amino acid lengths between 50-1,000) or a protein (larger than 1,000 amino acids). The peptide, polypeptide or protein can have only naturally occurring amino acids, or can be a mixture of naturally occurring and non-naturally occurring amino acids, or can have only non-naturally occurring amino acids.

The presentation molecules attached to the his-tag may be antigenic molecules, targeting molecules, therapeutic molecules, diagnostic molecules or molecules providing any other type of functionality. The tagged molecules may be used for targeting i.e., to guide the structures bearing the monolayers or bilayers to its targeted locations. For example, a peptide ligand can be attached to the his-tag such that the ligand guides liposomes (or other structures) to cells that have receptors or recognition molecules for the ligands. In one embodiment, the attached peptide could provide alternative or additional functionality—such as, for example, the attached peptide could provide therapeutic, diagnostic, or immunogenic functionality.

In specific embodiments, the presentation molecule may be a targeting molecule such as an antibody, peptide, aptamer or other molecules such as folic acid. The term "targeting molecule" is used to refer to any molecule that can direct the bilayer bearing structure such as liposome, to a particular target, for example, by binding to a receptor or other molecule on the surface of a targeted cell. Targeting molecules may be proteins, peptides, nucleic acid molecules, saccharides or polysaccharides, receptor ligands or other small molecules. The degree of specificity can be modulated through the selection of the targeting molecule. For example, antibodies typically exhibit high specificity. These can be polyclonal, monoclonal, fragments, recombinant, single chain, or nanobodies, many of which are commercially available or readily obtained using standard techniques.

The presentation molecule can be an antigenic molecule—i.e., a molecule bearing antigenic epitopes. In one embodiment, the molecule is a peptide. In one embodiment, the peptide is a RGD bearing peptide sequence. Such sequences may be 7-20 amino acids or longer bearing an epitope. The peptide may be a fragment of, or may comprise an epitope of a polypeptide or protein that is part of a microorganism, such as a pathogenic microorganism (e.g., virus, bacteria, parasites, or fungi). Examples include respiratory syncytial virus, *Borrelia burgdorferi* (referred to herein as Lyme borreliae), influenza viruses, and the like. The peptide may be a fragment of a popypeptide or protein that is generally not immunogenic, such as, for example, a viral protein that is not known to be practically immunogenic. The peptide may be fragment of, or may comprise an epitope of, a HIV antigen, such as an HIV outer envelope protein. In one embodiment, the HIV antigen is gp41. For example, the peptide can be membrane proximal external-region (MPER) of the gp41 envelope. Additional examples of antigens include, but are not limited to, DS-Cav1 for RSV, OspA for Lyme disease, and hemagglutinin and neuraminidase for influenza.

In one embodiment, the present disclosure provides antigenic compositions. The compositions comprise bilayer bearing structures in which an antigen having a histidine tail is non-covalently conjugated to the cobalt porphyrin (or cobalt porphyrin phospholipid) such that the his-tag is embedded in the bilayer and one or more epitopes of the antigen are exposed on the surface. The compositions may comprise adjuvants and other carriers known in the art. Examples of adjuvants include complete Freund's adjuvant, incomplete Freund's adjuvant, monophosphoryl lipid A (MPL), aluminum phosphate, aluminum hydroxide, alum, phosphorylated hexaacyl disaccharide (PHAD), Sigma adjuvant system (SAS), AddaVax (Invitrogen), or saponin. Other carriers like wetting agents, emulsifiers, fillers etc. may also be used.

A wide variety of cargo may be loaded into the liposomes or other structures of the present disclosure. The cargo can be delivered to desired locations using near infrared light. For example, bioactive or therapeutic agents, pharmaceutical substances, or drugs can be encapsulated within the interior of the CoPoP liposome. This includes water-soluble drugs and also drugs that are weak acids or bases that can be loaded via chemical gradients and concentrated in the aqueous core of the liposome. Thus, in various embodiments, the liposome comprises an active agent encapsulated therein, such as a therapeutic agent and/or a diagnostic agent, which can be a chemotherapy agent such as doxorubicin. The chemotherapeutic agent doxorubicin could be actively loaded and released with NIR irradiation providing for robust and direct light-triggered release using CoPoP liposomes.

In one embodiment, the ratio of lipid to drug (or any other cargo agent) is from 10:1 to 5:1. In various embodiments, the ratio of lipid to drug/cargo ratio is 10:1, 9:1, 8:1, 7:1, 6:1, or 5:1. The lipid used for calculating the ratios includes all the lipid including phospholipid that is part of the porphyrin phospholipid conjugate, additional phospholipids, or sterol, and lipid conjugated to PEG, if present. Although at times, cargo is described as a drug in the disclosure, the description is equally applicable to any agent contained for treatment and/or delivery to a desired location, and the term "drug" is intended to refer to any agent. The agent may be contained, in whole or in part, within on in the PoP-liposomes-whether present in the aqueous compartment, the bilayer or both.

In one embodiment, the cargo loaded within the liposome or other carriers is a therapeutic agent. The term "therapeutic agent" is art-recognized and refers to any chemical moiety that is a biologically, physiologically, or pharmacologically active substance. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Drugs that are known be loaded via active gradients include doxorubicin, daunorubicin, gemcitabine, epirubicin, topotecan, vincristine, mitoxantrone, ciprofloxacin and cisplatin. Therapeutic cargo also includes various antibiotics (such as gentamicin) or other agents effective against infections caused by bacteria, fungi, parasites, or other organisms. These drugs can be loaded and released in CoPoP liposomes.

In one embodiment, the cargo loaded in the liposome is a diagnostic agent. A "diagnostic" or "diagnostic agent" is any chemical moiety that may be used for diagnosis. For example, diagnostic agents include imaging agents, such as, for example, those containing radioisotopes such as indium or technetium; contrasting agents containing iodine or gadolinium; enzymes such as, for example, horse radish peroxidase, GFP, alkaline phosphatase, or beta.-galactosidase; fluorescent substances such as, for example, europium derivatives; luminescent substances such as, for example, N-methylacrydium derivatives or the like.

The cargo may comprise more than one agent. For example, cargo may comprise a combinations of diagnostic, therapeutic, immunogenic, and/or imaging agents, and/or any other type of agents. The same agent can have multiple functionalities. For example, an agent can be diagnostic and therapeutic, or an agent can be imaging and immunogenic and the like.

The structures formed by the layers of the present disclosure are serum stable. For example, in vitro, the his-tag binding stability to the CoPoP bilayers is stable when incubated in 50% bovine serum at room temperature for 24 hours. Thus, these structures can be stable under serum or concentrated or diluted serum conditions.

The present disclosure also provides methods for using structures bearing the bilayers as described herein. In one embodiment, this disclosure provides a method of eliciting an immune response in a host. The immune response may generate antibodies. The method comprises administering to an individual a composition comprising a structure bearing Co PoP bilayers to which is conjugated a histidine tagged antigen. The compositions may be administered by any standard route of immunication including subcutaneous, intradermal, intramuscular, intratumoral, or any other route. The compositions may be administered in a single administration or may be administered in multiple administrations including booster shots. Antibody titres can be measured to monitor the immune response.

The present nanostructures can be used for reducing antibody titer against desired antigens. For example, if immunogenicity is desired to be reduced, nanostructures in which PS (or other) containing phospholipids are present can be used. Compositions comprising these nanostructures can be administered for reducing immunogenicity.

In one aspect, the disclosure provides a method of delivery of agents contained as cargo in the liposomes or other nanostructures to desired locations. The agent may be contained, in whole or in part, within or in the CoPoP liposomes—whether present in the aqueous compartment, the bilayer or both. The method comprises 1) providing a composition comprising liposomes or other structures bearing the bilayers of the present disclosure optionally comprising cargo (such as an active agent); 2) allowing the liposomes to reach a selected or desired destination; 3) irradiating the liposome with radiation having a wavelength of near-infrared under conditions such that at least a portion of the cargo is released from the liposome. The cargo can alternatively, or additionally reach the interior of the cell by the liposomes being internalized and then releasing the cargo upon action of intracellular processes.

The liposomes may be irradiated with near-infrared light from a laser of power 50 to 1000 $mW/cm^2$, including all integer values to the $mW/cm^2$ and ranges therebetween, at a wavelength of from 650 to 1000 nm, including all integer values to the nm and ranges therebetween. In another embodiment, the wavelength is from 650 to 800 nm, including all integer values to the nm and all ranges therebetween. The liposomes may be irradiated for up to 30 minutes or less. In various embodiments, the liposomes in vitro or in vivo may be irradiated from 0.5 to 30 minutes and all values to the tenth decimal place therebetween. In one embodiment, the liposomes are irradiated with a 658 nm laser diode for up to 10 minutes. In other embodiments, the liposomes are irradiated with wavelengths of 665 or 671 nm. The infrared radiation can be delivered to the desired area directly by shining laser light on the area or fiber optic probes may be used. In the case of a tumor, the fiber optic probe can be inserted into the tumor (i.e., via a catheter or endoscopic device) to provide irradiation to a localized area.

In one aspect, the disclosure provides a method of preparing bilayers comprising CoPoPs. Freebase PoP can be produced by esterifying a monocarboxlic acid porphyrin such as pyropheophorbide-a with 2-palmitoyl-2-hydroxy-sn-glycero-3-phosphocholine (lyso-C16-PC), Avanti #855675P) using 1-Ethyl-3-(3-dimethylaminopropyl)carbodiimide and 4-dimethylaminopyridine in chloroform at a 1:1:2:2 lyso-C16-PC:Pyro:EDC:DMAP molar ratio by stirring overnight at room temperature. The PoP is then purified by silica gel chromatography. CoPoP can be generated by contacting porphyrin-phospholipid conjugate with a molar excess (e.g., 10-fold molar excess) of a cobalt salt (e.g., cobalt (II) acetate tetrahydrate) in a solvent (e.g., methanol) in the dark.

In one embodiment, this disclosure provides a method for coating a nanoparticle with a cobalt-porphyrin (e.g., CoPoP) bilayer or monolayer. The method generally comprises hydrating nanoparticles with a lipid solution in order to disperse the particles in water.

For delivery of cargo to desired locations or for general administration, the composition comprising the liposomes in a suitable carrier can be administered to individuals by any suitable route. In one embodiment, it is administered by intravenous infusion such that it will enter the vasculature (circulatory system). The composition may be administered systemically or may be administered directly into the blood supply for a particular organ or tissue or tumor. When irradiated by NIR, the contents of the PoP liposomes may be released within the circulatory system and may then enter the surrounding tissue.

In the following Statements, various examples of nanostructures, compositions, and methods of the present disclosure are described:

1. A nanostructure (e.g., a liposome) comprising: a) a monolayer or bilayer, wherein the monolayer or bilayer comprises: i) optionally, phospholipid, and ii) porphyrin having cobalt coordinated thereto forming cobalt-porphyrin; and b) optionally, a polyhistidine-tagged presentation molecule, where at least a portion of the polyhistidine tag resides in the hydrophobic portion of the monolayer or the bilayer or monolayer and one or more histidines of the polyhistidine tag are coordinated to the cobalt in the cobalt-porphyrin, where at least a portion of the polyhistidine-tagged presentation molecule is exposed to the outside of the nanostructure (e.g., liposome), and where, in the case of liposomes, the liposome encloses an aqueous compartment.
2. A nanostructure (e.g., liposome) of Statement 1, where the cobalt porphyrin is conjugated to a phospholipid to form a cobalt porphyrin-phospholipid conjugate.
3. A nanostructure (e.g., liposome) of Statement 2, where the cobalt porphyrin-phospholipid conjugate makes up from 1 to 25 mol % of the monolayer or the bilayer.
4. A nanostructure (e.g., liposome) of Statement 3, where the cobalt porphyrin-phospholipid conjugate makes up from 5 to 10 mol % of the monolayer or bilayer.
5. A nanostructure (e.g., liposome) of any one of Statements 1 to 4, where the bilayer further comprises a sterol (e.g., cholesterol).
6. A nanostructure (e.g., liposome) of any one of Statements 1 to 4, where the bilayer further comprises phosphatidylserine and, optionally, cholesterol.
7. A nanostructure (e.g., liposome) of any one of Statements 1 to 4, where the polyhistidine-tag comprises 6 to 10 histidine residues.
8. A nanostructure (e.g., liposome) of any one of Statements 1 to 4, where size of the liposome is 50 nm to 200 nm.
9. A nanostructure (e.g., liposome) of any one of Statements 1 to 4, where the nanostructure (e.g., liposome) comprises a cargo and, in the case of liposomes, at least a portion of the cargo resides in the aqueous compartment of the liposome.
10. A nanostructure (e.g., liposome) of any one of the preceding Statements, where the presentation molecule is a peptide of from 4 to 50 amino acids, said number of amino acids not including the histidines of the his-tag.
11. A nanostructure (e.g., liposome) of any one of the preceding Statements, wherein the presentation molecule is a protein from 4 to 500 kDa.
12. A nanostructure (e.g., liposome) of any one of the preceding Statements, where the presentation molecule is an antigenic molecule and the monolayer or the bilayer further comprises an adjuvant incorporated therein.
13. A nanostructure (e.g., liposome) of Statement 12, where the adjuvant is attenuated lipid A derivative.
14. A nanostructure (e.g., liposome) of Statement 13, where the attenuated lipid A derivative is monophosphoryl lipid A or 3-deacylated monophosphoryl lipid A.
15. A nanostructure comprising: a) a core; and b) a monolayer or a bilayer on said core, wherein the monolayer or bilayer comprises: i) optionally, phospholipid monomers, and ii) porphyrin having cobalt coordinated thereto forming cobalt-porphyrin (e.g., CoPoP); and c) optionally, a polyhistidine-tagged presentation molecule, where at least a portion of the polyhistidine tag resides in the hydrophobic portion of the monolayer or the bilayer, one or more histidines of the polyhistidine tag are coordinated to the cobalt in the cobalt-porphyrin, and at least a portion of the polyhistidine-tagged presentation molecule is exposed on the outside of the nanostructure.
16. A nanostructure of Statement 15, where the core is a gold nanoparticle.
17. A method of targeted delivery of a cargo comprising: a) administering to an individual a composition comprising nanostructures (e.g., liposomes) of any one of Statements 9 to 16 or a combination of nanostructures (e.g., liposomes) of any one of Statements 9 to 16 in a pharmaceutical carrier; and b) after a suitable period of time to allow the nanostructures (e.g., liposomes) to reach a desired location in the individual, exposing the liposomes to near infrared radiation of a wavelength from 650 to 1000 nm to effect release of the cargo from the liposomes.
18. A method of Statement 17, where the individual is a human or non-human animal.
19. A method for generating an immune response in a host individual comprising administering to the individual a composition comprising nanostructures (e.g., liposomes) of any one of Statements 1 to 16 or a combination nanostructures (e.g., liposomes) of any one of Statements 1 to 16 of in a pharmaceutical carrier, where the presentation molecule comprises an immunogenic epitope.
20. A method of Statement 19, where the presentation molecule is a peptide, polypeptide or protein derived from a pathogenic microorganism.
21. A method of any one of Statements 19 or 20, where the individual is a human or non-human animal.

The following examples are presented to illustrate the present disclosure. They are not intended to limiting in any manner.

Example 1

This example describes the synthesis and functionalization of cobalt porphyrin-phospholipid (CoPoP) bilayers with histidine-tagged ligands and antigens.

Materials and Methods.

Materials were obtained from Sigma unless otherwise noted. Peptides were obtained from commercial vendors that determined purity by HPLC and confirmed identity by mass spectrometry:

TABLE 1

Properties of peptides

| Name | Sequence | Expected | Observed mass | Purity mass | Source |
|---|---|---|---|---|---|
| RGD-His | 5-FAM-GRGDSPKGAGAKG-HHHHHHH (SEQ ID NO: 1) | 2475.52 | 2475.60 | 99.1% | GenScript |
| Free RGD | GRGDSPK (SEQ ID NO: 2) | 715.76 | 715.8 | 99.3% | GenScript |
| RGD-palm | 5-FAM-GRGDSPKGAGAKG (lys(palmiticacid) (SEQ ID NO: 3) | 1882.15 | N.D. | 96.7% | GenScript |
| cRGD-His | Cyclo(RGDY(D-)K(-Suc-PRG12-HHHHHHH)) (SEQ ID NO: 4) | 2280.5 | 2280.1 | 94.7% | Anaspec |
| 0-His | 5-FAM-KKGGGG (SEQ ID NO: 5) | 860.9 | 861.68 | 95.3% | Biomatik |
| 2-His | 5-FAM-KKGGGGHH (SEQ ID NO: 6) | 1135.18 | 1135.63 | 96.8% | Biomatik |
| 4-His | 5-FAM-KKGGGGHHHH (SEQ ID NO: 7) | 1409.46 | 1409.20 | 93.6% | Biomatik |
| 6-His | 5-FAM-KKGGGGHHHHHH (SEQ ID NO: 8) | 1683.75 | 1683.40 | 92.8% | Biomatik |
| 8-His | 5-FAM-KKGGGGHHHHHHHH (SEQ ID NO: 9) | 1958.03 | 1957.30 | 92.9% | Biomatik |
| 10-His | 5-FAM-KKGGGGHHHHHHHHHH (SEQ ID NO: 10) | 2232.32 | 2231.64 | 90.9% | Biomatik |
| MPER-His | NEQELLELDKWASLWNGGKG-HHHHHHH (SEQ ID NO: 11) | 3304.52 | 3304.75 | 93.6% | GenScript |
| MPER-Biotin | NEQELLELDKWASLWNGGK-Biotin (SEQ ID NO: 12) | 2584.91 | 2285.55 | 90.1% | GenScript |

For protein binding, the recombinant heptahistidine-tagged cerulean-venus fusion reporter protein was produced in *Escherichia coli* and was purified and characterized as previously described. Stoichiometry approximations were based on the assumption that each ~100 nm liposome contains 80,000 lipids.

Generation of PoP-Lipid, PoP-Liposomes and PoP-Gold.

Freebase (2H) PoP sn-1-palmitoyl sn-2-pyropheophorbide phosphtatidylcholine was synthesized as previously described. CoPoP was generated by stirring 100 mg 2H-PoP with 10 fold molar excess of cobalt (II) acetate tetrahydrate in 4 mL methanol for 17 hours in the dark. Reaction completion and product purity was monitored by TLC (>90% purity). The solvent was then removed by rotary evaporation and PoP was extracted with chloroform:methanol:water (1:1.8:1) 3 times. The chloroform layer was collected, the solvent was removed by rotary evaporation and the product was freeze-dried in 20% water in tert-butanol to give 81.5 mg (77% yield) (Identity was confirmed with mass spectrometry). Other metallo-PoPs were synthesized using the same method. For Ni-PoP, Ni (II) acetate tetrahdrate was used and incubated for 17 hours. For Zn-PoP, Zn (II) acetate dehydrate was used and incubated for 17 hours. For Mn-PoP, Mn (II) acetate was used and incubated for 30 hours. For Cu-PoP, Cu (II) acetate was used and incubated in tetrahydrofuran for 3 hours.

PoP-liposomes were formulated at a 1 mg scale. After dissolving lipids in chloroform in a test tube, the solvent was evaporated and the film was further dried under vacuum overnight. Lipids were rehydrated with 1 mL of phosphate buffered saline (PBS), sonicated, subjected to 10 freeze-thaw cycles and then extruded through 100 nm polycarbonate membranes (VWR #28157-790) with a handheld extruder (Avanti #610000). For protein and peptide binding analysis, liposomes were formed with 10 mol % PoP along with 85 mol % DOPC (Avanti #850375P), and 5 mol % PEG-lipid (Avanti #880120P). Ni-NTA liposomes included 10 molar % Ni-NTA lipid dioleoyl-glycero-Ni-NTA (Avanti #790404P) as well as 10 molar % 2H-PoP. Liposomes incorporating free Co-porphyrin included 10 molar % Co-pyropheophorbide with 85 mol % DOPC and 5 mol % PEG-lipid. Co-NTA-liposome was prepared using liposomes containing 10 mol % dioleoyl-glycero-NTA (Avanti #790528P). Liposomes were incubated with 20 mg/mL cobalt (II) chloride for 2 hours and then dialyzed in PBS. Sulforhodamine B loading liposomes contained 10 mol % PoP, 35 mol % cholesterol (Avanti #700000P), 55 mol % DOPC and PEG-lipid as indicated. A solution of sulforhodamine B (VWR #89139-502) was used to hydrate the lipid film, which was then freeze-thawed then sonicated. Unentrapped dye was removed with a 10 mL Sephadex G-75 (VWR #95016-784) column followed by dialysis in PBS.

For bilayer integrity and quantitative cell binding studies, 50 mM dye was used, whereas microscopy studies used 10 mM dye.

For gold coating, 60 nm citrate-stabilized gold nanospheres (Ted Pella #15709-20) were used to hydrate a 1 mg lipid film composed of 45 mol % distearoyl phosphocholine (Avanti #850365P), 45 mol % distearoyl phosphoglycerol (Avanti #840465X) and 10 mol % PoP. Following brief vortexing and sonication, the samples were repeatedly centrifuged at 1500 relative centrifugal force (rcf) for 15 min. The supernatant was discarded and the pellet was resuspended and re-centrifuged 2 more times. PoP gold was resuspended in water for further analysis.

Polypeptide Binding.

1 μg of fluorescent reporter protein was incubated with 20 μg of liposomes in 200 μL PBS in a 96 well plate. Fluorescence in the FRET channel (ex: 430 nm, em: 525 nm) was measured periodically with a fluorescence microplate reader (Tecan Infinite II). Data were normalized to the FRET signal in the protein without addition of liposomes. EMSA experiments were performed with 2.5 μg protein incubated with 50 μg liposomes followed by electrophoresis in a 0.75% agarose gel with 50 V applied for 90 minutes and imaging with an IVIS Lumina II system with the indicated excitation and emission filters. For serum stability test, 3 mg protein was pre-incubated with 60 mg liposome in 40u 1 PBS. After 24 incubation, 40u 1 FBS was added and incubated for another 8 h (hours). For imidazole displacement experiments, 1 μg of reporter protein was bound to 20 μg liposomes in PBS. Imidazole was then titrated and binding was assessed with fluorescence. For serum stability, 1 μg of reporter protein was bound to 20 μg liposomes in 100 μL PBS and then an equal volume of fetal bovine serum (VWR #82013-602) was added and binding was monitored with fluorescence. Peptide binding was assessed with RGD-His FAM fluorophore quenching following incubation of 500 ng peptide with 20 μg liposomes.

Targeting Experiments.

U-87 and MCF-7 cell lines were obtained from ATCC and cultured according to vendor protocol. $2 \times 10^4$ cells were seeded overnight in 96-well-plate wells. 500 ng RGD-His peptide was bound with 20 μg of sulforhodamine B loaded liposomes and liposomes were incubated with cells for 2 h. Media was removed, cells were washed with PBS 3 times and then cells and liposomes were lysed with a 1% Triton X-100 solution. Liposomal uptake was assessed by measuring the fluorescence of sulforhodamine B.

For confocal imaging, $10^4$ cells were seeded overnight in a Nunc chamber slide (Nunc #155411) in DMEM with 10% fetal bovine serum (FBS). 20 μg of liposomes were added to the serum containing media and incubated for 2 h. Media was removed and the cells were washed with PBS 3 times. Fresh media was added and cells were imaged with microscopy using a Zeiss LSM 710 confocal fluorescence microscope. Gold imaging was carried out in the same way but 633 nm light was used for both excitation and emission for back scatter imaging. After peptide binding, gold was centrifuged to remove any unbound RGD peptide.

For in vivo experiments, animal procedures were conducted in accordance with the policies and approval of the University at Buffalo Institutional Animal Care and Use Committee (IACUC). 5-week old female athymic nude mice (Jackson Labs) were inoculated on the flank with U87 cells and mice were treated when tumor growth reached 4-5 mm diameter. Mice were intravenously injected with 200 μL of sulforhodamine B-loaded liposomes (1 mg/mL llipid) targeted with or without cRGD-his. 45 minutes after injection mice were sacrificed, organs were extracted, weighed, mechanically homogenized in a 0.2% Triton X-100 solution and fluorescence was assessed to determine biodistribution.

Vaccinations.

Unless otherwise indicated, 8-week-old female BALB/c mice (Harlan Laboratories) received hind ventral footpad injections on days 0 and 14 containing 25 μg of MPER peptide in 50 μL of sterile PBS. Where indicated, injections also included 25 μg MPL (Avanti #699800P) or TDB (Avanti #890808P) in liposomes comprising DOPC:Cholesterol:MPL:PoP at a molar ratio of 50:30:5:5. For Freund's adjuvant, the peptide was mixed directly in Fruend's complete adjuvant (Fisher #PI-77140) and injected. 4 weeks following the first injection, or as indicated, blood was collected from the submandibular vein and serum was obtained following blood clotting and centrifugation at 2000 rcf for 15 min and stored at −80° C.

Anti-MPER titer was assessed by ELISA in 96-well streptavidin-coated plates (GBiosciences #130804). 1 μg of His-tag-free MPER-biotin in 100 μL of PBS containing 0.1% Tween 20 (PBS-T) was incubated in the wells for 2 h at 37° C. Wells were then washed 5 times with PBS-T and mouse sera was serially diluted in PBS containing 0.1% casein (PBS-C) and incubated for 30 min at 37° C. Wells were washed 5 times with PBS-T then 100 μL of goat anti-mouse IgG-HRP (GenScript #A00160) diluted in PBS-C was added to the wells to provide a final concentration of containing 1 μg/mL secondary antibody and incubated for 30 min at 37° C. The wells were washed 5 times with PBS-T then 100 μL tetramethylbenzidine substrate solution (Amresco #J644) was added to each well and incubated for 20 min at 37° C. The reaction was stopped by 100 μL 1M HCl and absorption was measured at 450 nm. Titers were defined as the reciprocal dilution at which the absorbance at 450 nm exceeded the identical dilution of non-serum background by greater than 0.05 absorbance units. Every sample was averaged from duplicate measurements.

Viral Entry Experiments.

Viral entry experiments were carried out as previously described. In short, HIV-1 was produced by co-transfection of pHXB2-env and pNL4-3.HSA.R-E- in 293T cells. 2 days post-transfection, the cell media was passed through a 0.45 μm filter and centrifuged. The viral pellet was dried, resuspended in 600 μL of PBS and stored at −80° C. The infectious titer of HIV-1 stock was determined by X-Gal staining as previously described.

Sera from 3 mice immunized with MPER and CoPoP liposomes was pooled and IgG was isolated using immobilized Protein G beads (VWR #PI20398) according to vendor protocol. Concentration was determined with absorption with the Bradford assay. 2F5 was obtained from the free NIH AIDS reagent program. $1 \times 10^4$ TZM-b1 receptor cells per well were plated to a 96-well plate the day before infection. HIV (multiplicity of infection of 0.1) was incubated with antibodies for 30 min at 37° C., added to the cells and spinoculated at 1000 rcf for 1 h at 25° C. followed by further incubation for 2 days at 37'C in a 5% $CO_2$ incubator. Cell viability was then measured using a CellTiter-Fluor Assay (Promega) according to manufacturer protocol. Viral entry level was then measured by a luciferase assay system (ONE-Glo, Promega) according to manufacturer protocol and was normalized to the virus only sample. Data were further normalized to cellular viability (all groups exhibited viability within 10% of the control untreated cells).

Results

His-Tagged Protein Binding to CoPoP Liposomes.

A series of sn-1-palmitoyl sn-2-pyropheophorbide phosphtatidylcholine chelates was generated with the transition metals Co, Cu, Zn, Ni and Mn (FIG. 1c). PoP bilayers were then formed with 10 molar % metallo-PoP along with 85 molar % dioleoylphosphocholine (DOPC) and 5 molar % polyethylene glycol-conjugated distearoylphosphoethanolamine (PEG-lipid) via extrusion into 100 nm liposomes. His-tagged protein binding to PoP bilayers was assessed with a fluorescent protein reporter. As shown in FIG. 2a, the system comprised a fusion protein made up of two linked fluorescent proteins; Cerulean (blue emission) and Venus (green emission). Due to their linked proximity and spectral overlap, Cerulean serves as a Förster resonance energy transfer (FRET) donor for Venus, so that Cerulean excitation results in FRET emission from Venus. Cerulean was tagged at its C-terminus with a heptahistidine tag. However, if bound to a PoP bilayer, energy transfer from Cerulean is diverted to the bilayer itself, which is absorbing in the Cerulean emission range and thus competes with FRET to Venus. On the other hand, because Venus is not directly attached to the photonic bilayer, it is not completely quenched upon direct excitation, which enables tracking of the bound fusion protein.

A 3-color electrophoretic mobility shift assay (EMSA) was developed to assess reporter fusion protein binding to various PoP liposomes. 2.5 µg protein was incubated with the 50 µg of various PoP liposomes for 24 hours and then subjected to agarose gel electrophoresis. As shown in the top image in FIG. 2b, when the PoP-liposomes were imaged only the free base (2H) liposomes were readily visualized, along with the Zn-PoP liposomes to a lesser degree. This demonstrates that the metals have a quenching effect on the PoP and confirms they were stably chelated in the bilayer. As expected, the liposomes exhibited minimal electrophoretic mobility due to their relatively large size. Next, the same gel was imaged using Cerulean excitation and Venus emission to probe for inhibition of FRET, which would be indicative of the fusion protein binding to PoP liposomes. All the samples exhibited the same amount of FRET and migrated the same distance as the free protein with the exception of the protein incubated with CoPoP liposomes, in which case FRET disappeared completely (middle image). To verify the presence of the protein, Venus was directly excited and imaged. Only with the CoPoP liposomes was the reported protein co-localized with the liposomes. Together, these images demonstrate that the protein bound quantitatively to CoPoP liposomes. Solution-based studies confirmed this finding (FIG. 2c). Of all the types of PoP liposomes examined, only the CoPoP ones induced a dramatic decrease in the FRET efficiency between Cerulean and Venus, due to liposomal binding. The binding required approximately a day to fully complete, although the time to achieve 50% binding (the $t_{1/2}$) was just 3 hours. It was shown by molecular dynamics simulations of a 2H-PoP bilayer that the center of the porphyrins (where metal chelation would occur) are inaccessible to the aqueous phase surrounding the bilayer. Thus, this slow binding can be attributed to a His-tag that is partially obscured by the rest of the protein as well as having to making its way into the sheltered hydrophobic bilayer.

Polyhistidine Coordination with CoPoP.

The mechanism underlying His-tag binding to immobilized metals involves metal coordination with the nitrogenous imidazole groups of histidine residues. The absence of His-tag binding to liposomes formed with Ni(II), Cu(II), Zn(II) and Mn(II) PoP likely relates to axial ligand binding affinity or the coordination number within the porphyrin. For instance, it has been proposed that Ni(II) and Cu(II) porphyrin chelates can coordinate completely with the 4 surrounding macrocyclic nitrogens atoms without axial ligands. For the Zn (II) and Mn (III) porphyrins, the ligand binding strength is likely insufficient to confer stable polyhistidine binding.

Figure 2:
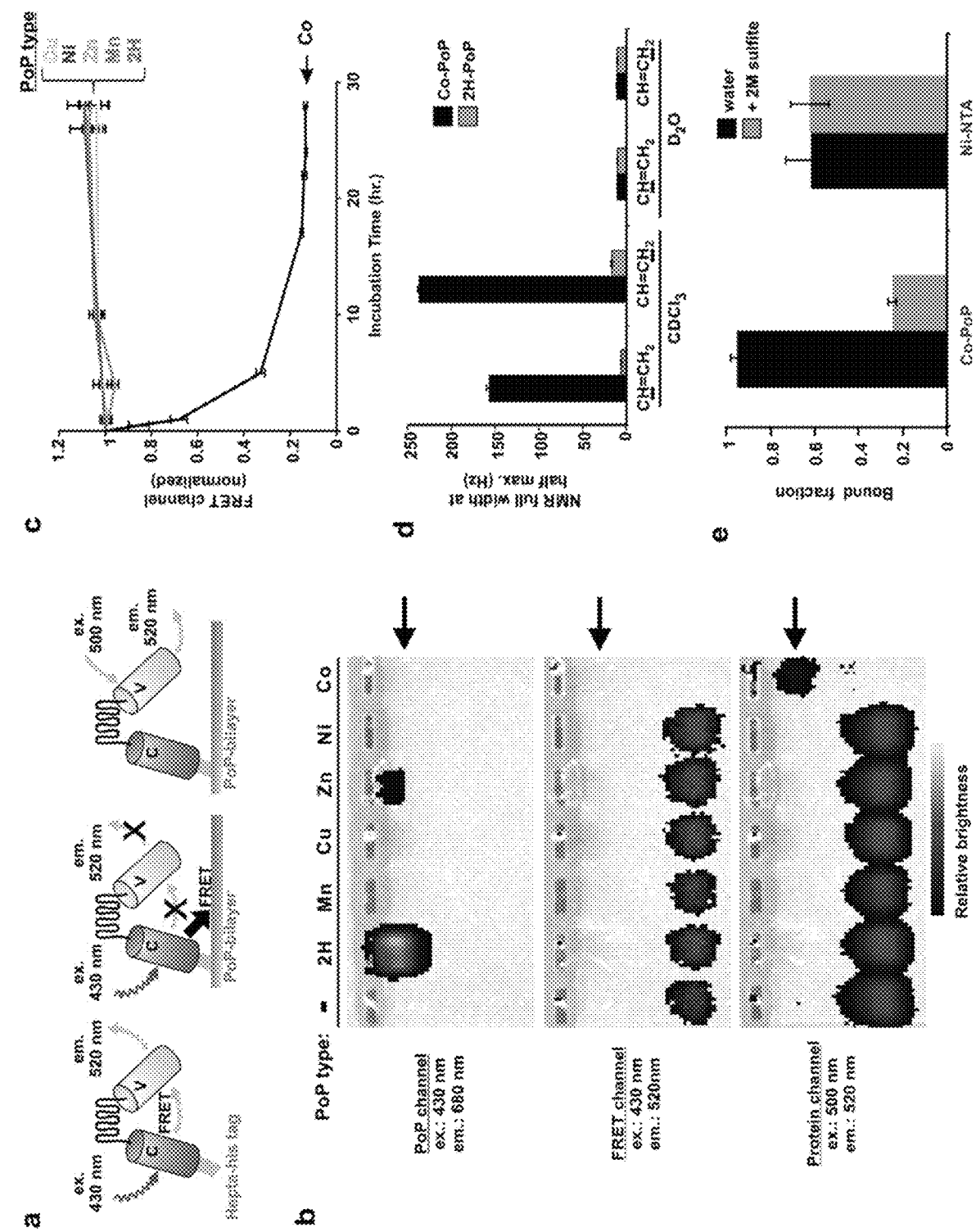
FIG. 2. His-tagged protein binding to Co(III)-PoP liposomes. (a) A heptahis-tagged fluorescence protein comprising Cerulean (C) fused to Venus (V) reveals binding to PoP-bilayers. When C is excited, FRET occurs and V emits fluorescence (left), but this is inhibited when bound to the PoP-bilayer due to competing FRET with the photonic bilayer (middle). C fluorescence can be directly probed even when the protein is bound to the bilayer (right). (b) Multispectral fluorescence images of fusion protein electrophoretic mobility shift following incubation with indicated metallo-PoP liposomes. (c) Binding kinetics of the fusion protein to the indicated metallo-PoP liposomes based on loss of C to V FRET. (d) NMR peak widths of the underlined proton of the vinyl group on CoPoP demonstrate paramagnetic broadening of Co (II) in deuterated chloroform ($CDCl_3$) but non-paramagnetic peaks of Co(III) following CoPoP-liposome formation in deuterated water. For each set of bars, left to right are bars for: CoPoP and 2H-PoP (e) Reversal of His-tagged peptide binding to CoPoP liposomes following addition of 2 M sodium sulfate. Liposomes were formed with 10 molar % CoPoP or Ni-NTA phospholipid. For each set of bars, the bars from left to right are: water, and +2M sulfite.

To determine the electronic state of the CoPoP, paramagnetism was assessed. Because Co(II) is paramagnetic, but Co (III) porphyrins are low-spin and diamagnetic, NMR was used to probe for peak broadening induced by paramagnetic species. As shown in FIG. 2d, based on the hydrogens of each carbon of the vinyl group within the PoP, wide peak broadening was observed only for the CoPoP, and only in organic solvent. When CoPoP was formed into aqueous liposomes, the peaks narrowed, indicative of oxidation to diamagnetic Co (III) within the bilayer. To further verify this mechanism, the reducing agent sodium sulfite was added to CoPoP liposomes after they quantitatively bound a fluorescently-labeled His-tagged peptide. As shown in FIG. 2e, 2 M sulfite induced peptide release from CoPoP liposomes. Liposomes were also formed with commercially available Ni-NTA lipid. The His-tagged peptide did not bind as avidly to the Ni-NTA liposomes. Upon addition of sulfite to the system, no release of the peptide was observed, as would be expected with Ni (II) which cannot readily be reduced. Together, these data suggest that CoPoP transitions from Co (II) to Co (III) upon forming CoPoP liposomes and the polyhistidine imidazole groups coordinate in the bilayer with chelated Co (III) in the PoP.

Stable His-Tag Binding to CoPoP Liposomes.

Figure 3:
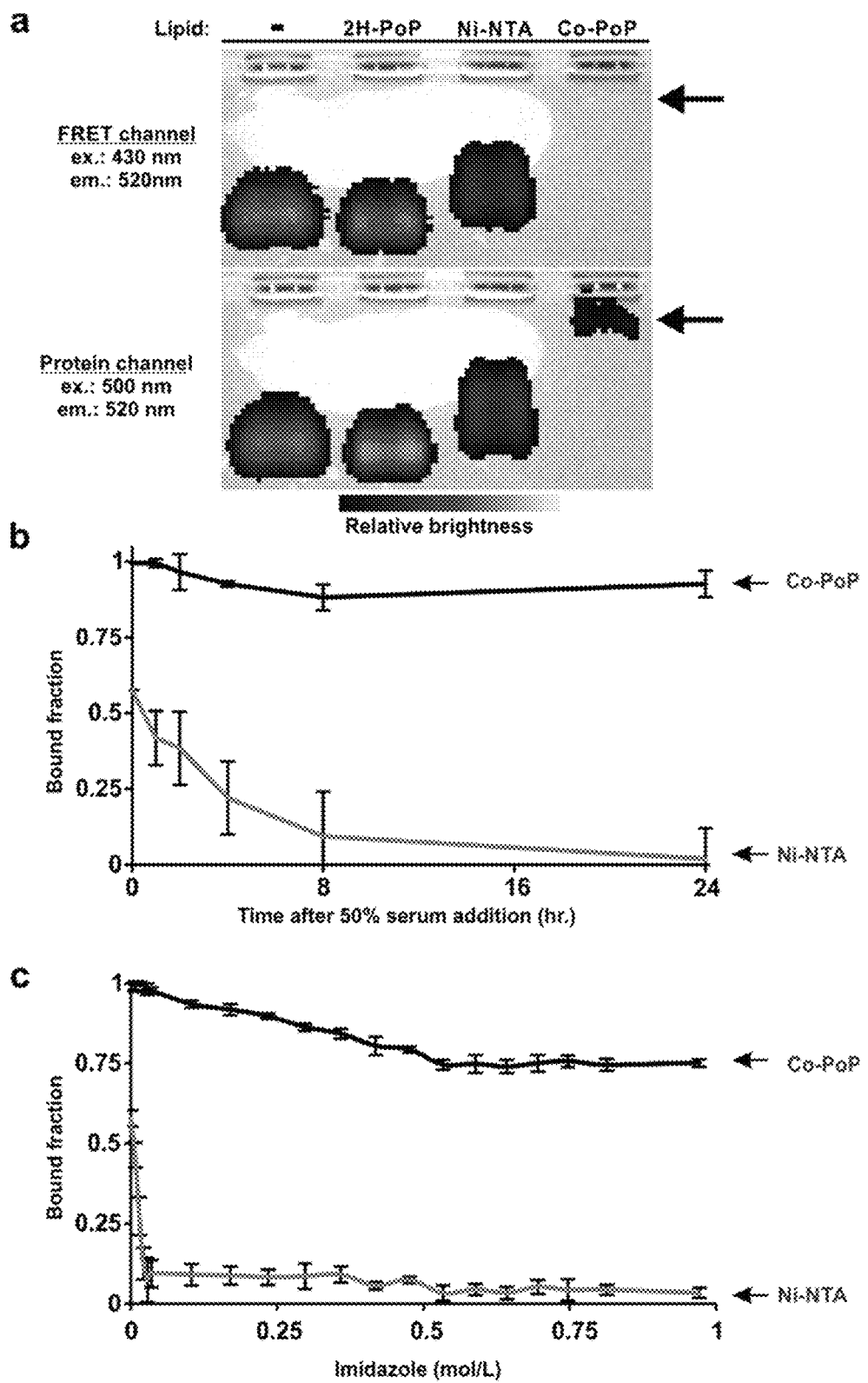
FIG. 3. Robust His-tagged protein binding to CoPoP liposomes (a) Multispectral electrophoretic mobility shift images of the fluorescent reporter protein incubated with liposomes containing the indicated lipid. (b) Binding stability of reporter protein bound to indicated liposomes in 1:1 serum. (c) Binding stability of reporter protein bound to indicated liposomes in excess free imidazole. Mean+/−std. dev. for n=3.

The fluorescence reporter protein was then used to compare the binding of His-tagged proteins to liposomes incorporating either CoPoP or Ni-NTA-lipid (FIG. 3a). Ni-NTA liposomes included 10 molar % 2H-PoP to enable protein binding determination based on FRET. By EMSA, the protein migrated unimpeded when incubated without liposomes or when incubated with 2H-PoP liposomes in both the FRET channel and protein channel. When incubated with Ni-NTA liposomes, migration of the protein was only slightly inhibited, indicating that the protein binding did not withstand the conditions of electrophoresis. The FRET channel was unquenched, confirming a lack of binding to the Ni-NTA liposomes. In contrast, when incubated with the CoPoP liposomes, the protein stably bound with a complete disappearance of the FRET channel and decreased electrophoretic mobility that was consistent with the protein remaining bound to liposomes.

For biomedical applications, an intractable obstacle of using Ni-NTA-lipid is that it does not maintain stable His-tag binding in biological media such as serum. To examine whether liposomes could maintain binding in the presence of serum, fetal bovine serum was added at a 1:1 volume ratio to a solution of liposomes that had bound the His-tagged protein. As shown in FIG. 3b, Ni-NTA liposomes did not fully sequester all the protein, which is consistent with the weak binding exhibited in the EMSA result. Furthermore, following serum addition, all binding was abrogated over a 24 hour period. In the same conditions CoPoP liposomes stably sequestered the His-tagged reporter protein without substantial protein release.

Since the histidine side chain comprises an imidazole group, an imidazole competition assay was used to compare the Ni-NTA and CoPoP liposomes binding stability with His-tagged polypeptides. As shown in FIG. 3c, CoPoP liposomes maintained over 75% binding to the reporter protein even at concentration approaching 1 M imidazole.

This represents an approximate 10 million fold imidazole excess over the 100 nM protein concentration used in the binding study. In contrast, the Ni-NTA liposomes released over 90% of the His-tag in the presence of just 30 mM imidazole. The drastically stronger binding of the CoPoP liposome to the His-tag may be attributed to at least 2 factors; the superior stable chelation of Co(III) to imidazole groups and the protected hydrophobic environment of the CoPoP bilayer which limits access to competing external molecules.

Figure 7:
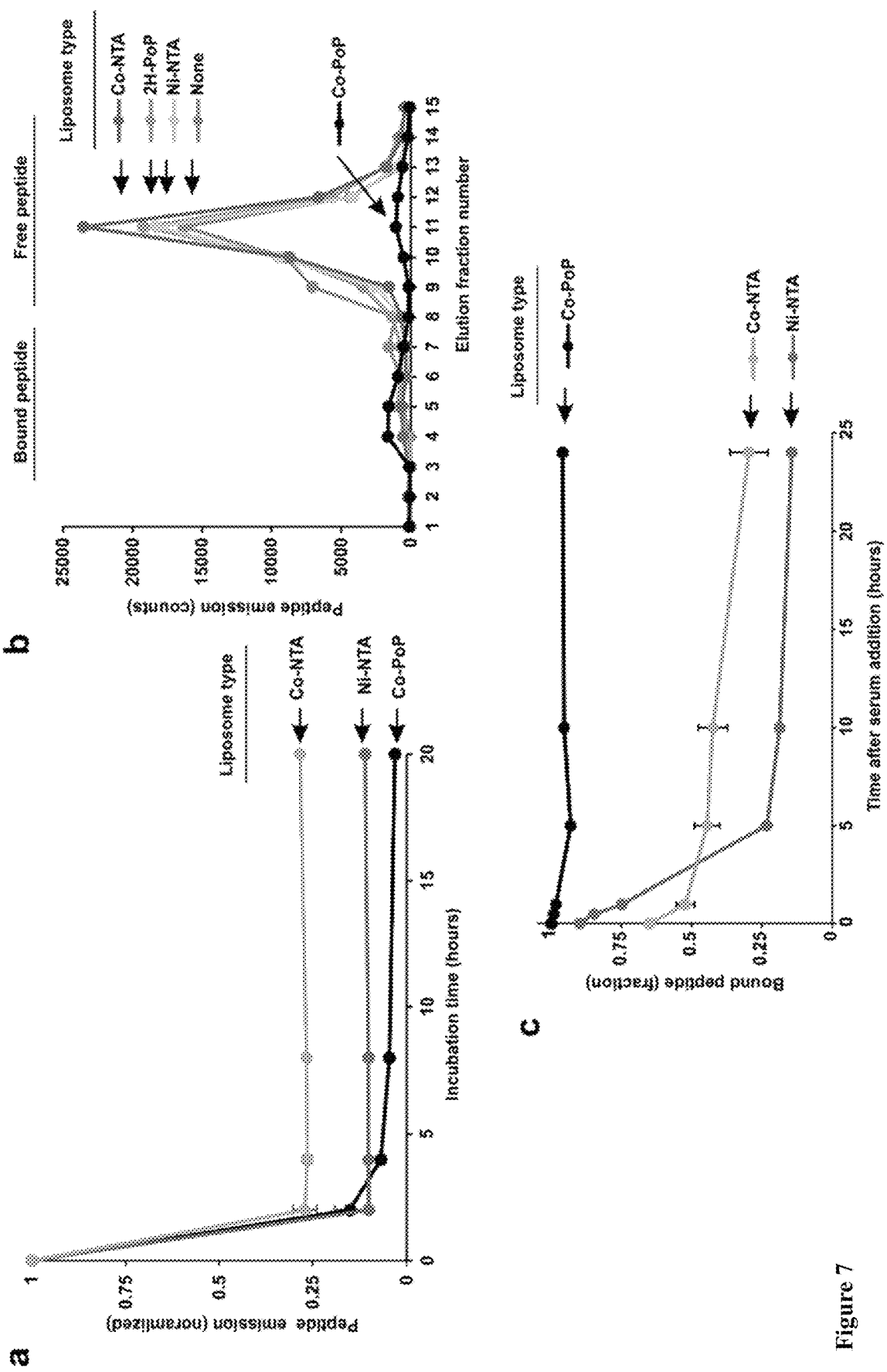
FIG. 7. Stability of RGD-His peptide binding to liposomes. (a) FAM-labeled RGD-His peptide binding to liposomes containing 10 molar % Ni-NTA-lipid, Co-NTA-lipid or CoPoP. (b) Gel filtration following peptide binding. Only CoPoP liposomes maintained stable binding (c) Peptide stability following incubation with a 1:1 dilution in fetal bovine serum. Only CoPoP liposomes maintained stable binding.
Figure 8:
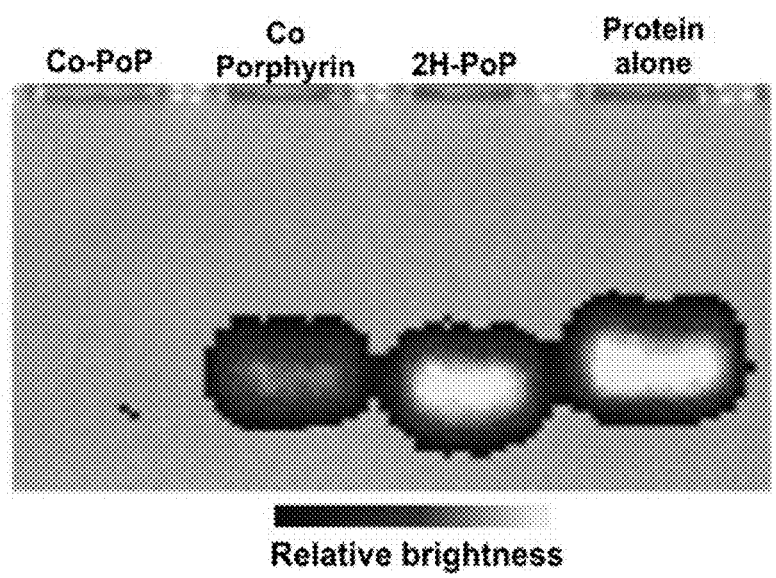
FIG. 8. Stable his-tagged protein binding to liposomes containing CoPoP. The reporter protein was incubated with liposomes containing CoPoP, free Co-porphyrin or 2H-PoP, then incubated in serum and subjected to EMSA. The protein was then imaged using the FRET channel (ex: 430 nm, em: 525 nm). The lack of signal in the CoPoP lane demonstrates stable binding to the liposomes. The diminished signal in the Co-porphyrin lane demonstrates some binding of the his-tagged protein to the liposomes.

Liposomes formed with Ni-NTA-lipid, the cobalt-chelated Co-NTA-lipid, and CoPoP could bind a fluorescent peptide in solution (FIG. 7a). However, the binding of Co-NTA and Ni-NTA was not maintained during gel filtration chromatography (FIG. 7b). Liposomes formed with Co-NTA and Ni-NTA, but not CoPoP, released the peptide when incubated in serum (FIG. 7c). This demonstrates the significance of bilayer-confined polyhistidine binding. We next examined whether or not CoPoP was required for stable binding in serum, or whether a simple liposome-inserted cobalt porphyrin (Co-pyro) could be sufficient. After initial binding, incubation with serum caused the polypeptide to become displaced from the liposomes (FIG. 8). This result is consistent with recent demonstrations that membrane-inserted porphyrins, but not PoP, rapidly exchange with serum components and exit the liposome. Together these results point to the essential role of CoPoP in order to stably bind His-tagged polypeptides.

Peptide Binding to CoPoP Liposomes

Figure 4:
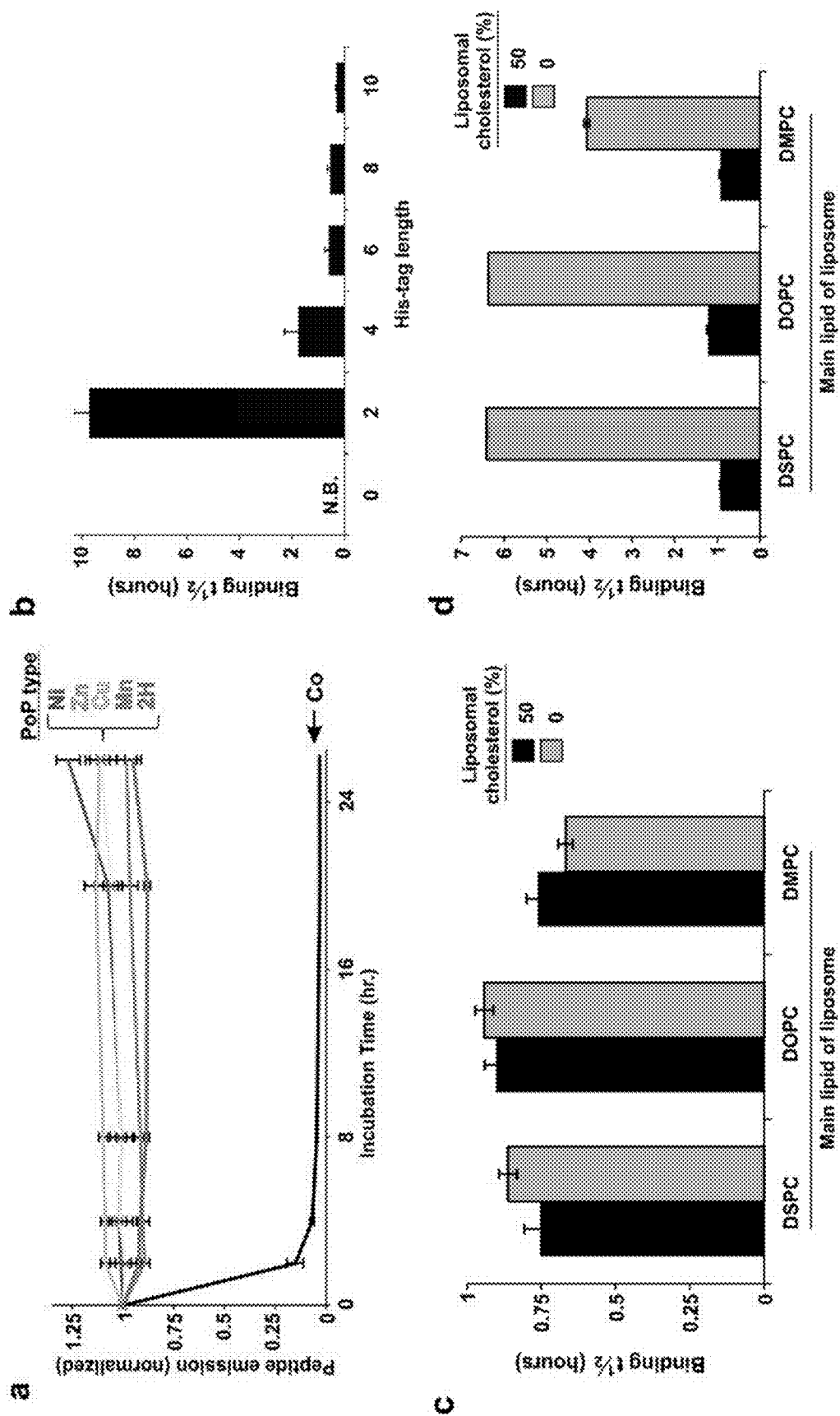
FIG. 4. Binding of a short His-tagged RGD peptide to CoPoP liposomes. (a) Binding of a short peptide labeled with FAM to metallo-PoP liposomes. (b) Effect of His-tag length on binding half-time to CoPoP liposomes. No binding "N.B." was observed for the peptide lacking a His-tag. Effect of liposome composition on binding half-time to CoPoP liposomes of indicated composition when incubated in PBS (c) or in 5 mg/mL BSA (d). Mean+/−std. dev. shown for triplicate measurements. In (c) and (d), for each set of bars, the bars from left to right are 50 and 0.

Peptide targeting has attracted interest for use as disease and tissue-specific "zip codes". The short RGD tripeptide, which is found in fibronectin and vibronectin, is a promising targeting ligand for its effective binding to the integrin $\alpha v\beta_3$ expressed on tumor endothelial cells. CoPoP liposomes were examined to verify whether they can be delivered to molecular receptors on target cells via a His-tagged ligand approach with the short linear amino acid sequence GRGDSPK-GAGAKG-HHHHHHH (SEQ ID NO:1). Carboxy fluorescein (FAM) was labeled on the N-terminus to enable detection of binding to PoP-liposome via FRET. It has been shown that linear RGD peptides can be labeled with fluorophores without disrupting integrin binding. As shown in FIG. 4a, when this peptide was incubated with various metallo-PoP liposomes, only the CoPoP ones bound the peptide. Compared to protein-binding, peptide-binding was about five times faster. Presumably, the smaller size, faster molecular motion and decreased steric hindrance of the peptide enabled more rapid interdigitation into the bilayer to interact with and irreversibly bind the CoPoP. Based on previous estimates that each ~100 nm liposome contains approximately 80,000 lipids, this equates to 8000 CoPoPs and 750 peptides per liposome. Since each peptide contained 7 histidine residues, the ratio of CoPoP to histidine in the bilayer was 1:0.66. For conventional His-tag binding to Ni-NTA, of all the residues in the His-tag, just the ith and i+2 or i+5 histidine residues are believed to be involved in coordinating with the metal. The porphyrin and polyhistidine density within the CoPoP bilayer is likely higher and therefore the coordination mechanism may be different.

The effect of His-tag length on peptide binding to CoPoP liposome was examined. A series of N-terminus FAM-labeled peptides was synthesized with varying lengths of His-tag attached to the C-terminus. As demonstrated in FIG. 4b, when the His-tag was omitted from the peptide, no peptide binding was observed. With 2 histidine residues, the binding was slow, with a binding $t_{1/2}$ of nearly 10 hours. As the His-tag length increased, binding speed rapidly increased. With 6 residues, corresponding to the common hexahistidine tag, binding $t_{1/2}$ was less than one hour. By increasing the His-tag length to 10 residues, binding $t_{1/2}$ decreased to 20 minutes.

Figure 9:
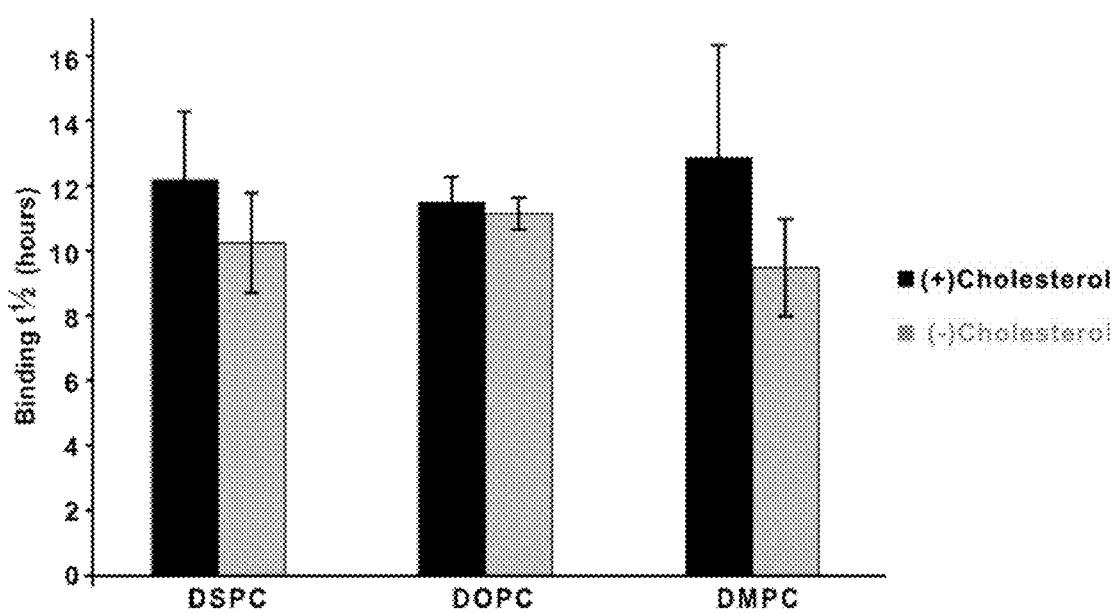
FIG. 9. Time for 90% peptide binding of RGD-His to CoPoP liposomes of different compositions. Effect of liposome composition on the time for 90% peptide binding to CoPoP liposomes (10 molar % CoPoP), containing the indicated components when incubated in PBS with the RGD-His peptide. For each set of bars, the bars from left to right are: +cholesterol, and −cholesterol.
Figure 10:
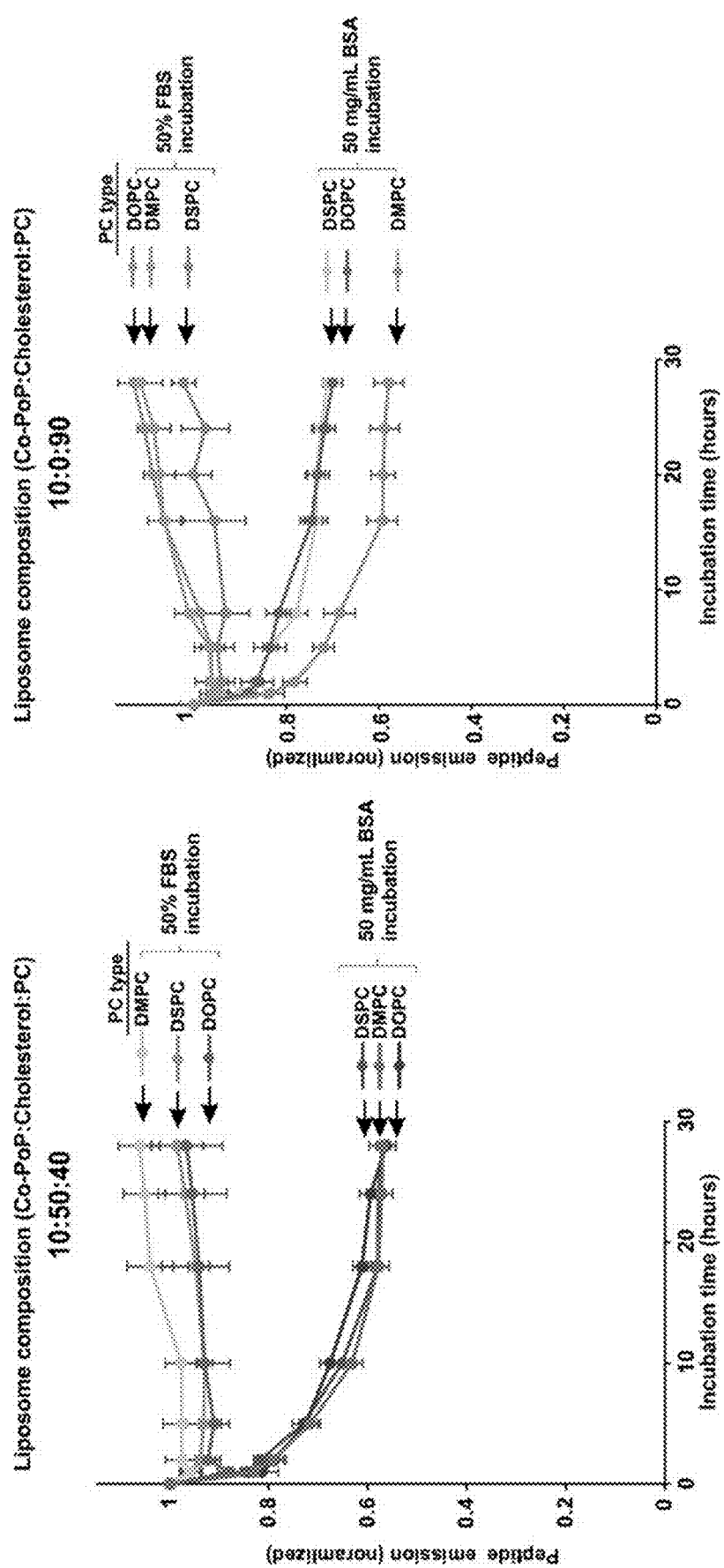
FIG. 10. RGD-His binding to CoPoP liposomes in the presence of serum or albumin. Liposomes of the indicated composition were incubated with the RGD-his peptide in the presence of 50% fetal bovine serum or 50 mg/mL bovine serum albumin. The FAM-labeled peptide emission was normalized by comparing the peptide emission when bound to CoPoP liposomes to 2H-PoP liposomes.

Next, lipid composition was varied to determine the effect of membrane fluidity on His-tag binding. Liposomes were formed with 90 mol % of either DSPC, DMPC or DOPC along 10 mol % CoPoP, Alternatively, 50 mol % cholesterol was incorporated in the bilayer with a corresponding reduction in the amount of standard lipid used. DSPC forms rigid, gel-phase bilayers at room temperature, whereas DMPC and DOPC have lower transition temperatures and are in the liquid crystal phase. Cholesterol occupies space in the bilayer and can have a moderating effect on membrane fluidity. Interestingly, no major differences were observed in the peptide binding rate to membranes of different compositions, with or without cholesterol (FIG. 4c). The peptide binding process might occur in a multi-step process and that once the peptide begins insertion into the bilayer, cooperative effects of the polyhistidine are not impacted by lipid composition. However, in 5 mg/mL bovine serum albumin (BSA), dramatic differences between the membranes with and without cholesterol were observed (FIG. 4d). The slower binding in cholesterol-free liposomes was likely due to greater interaction of BSA with the membrane interfering with peptide binding. Binding half-times were not reached with BSA at 50 mg/mL and serum completely inhibited binding (FIG. 9 FIG. 10).

Biotargeting of Cargo-Loaded Liposomes.

Figure 5:
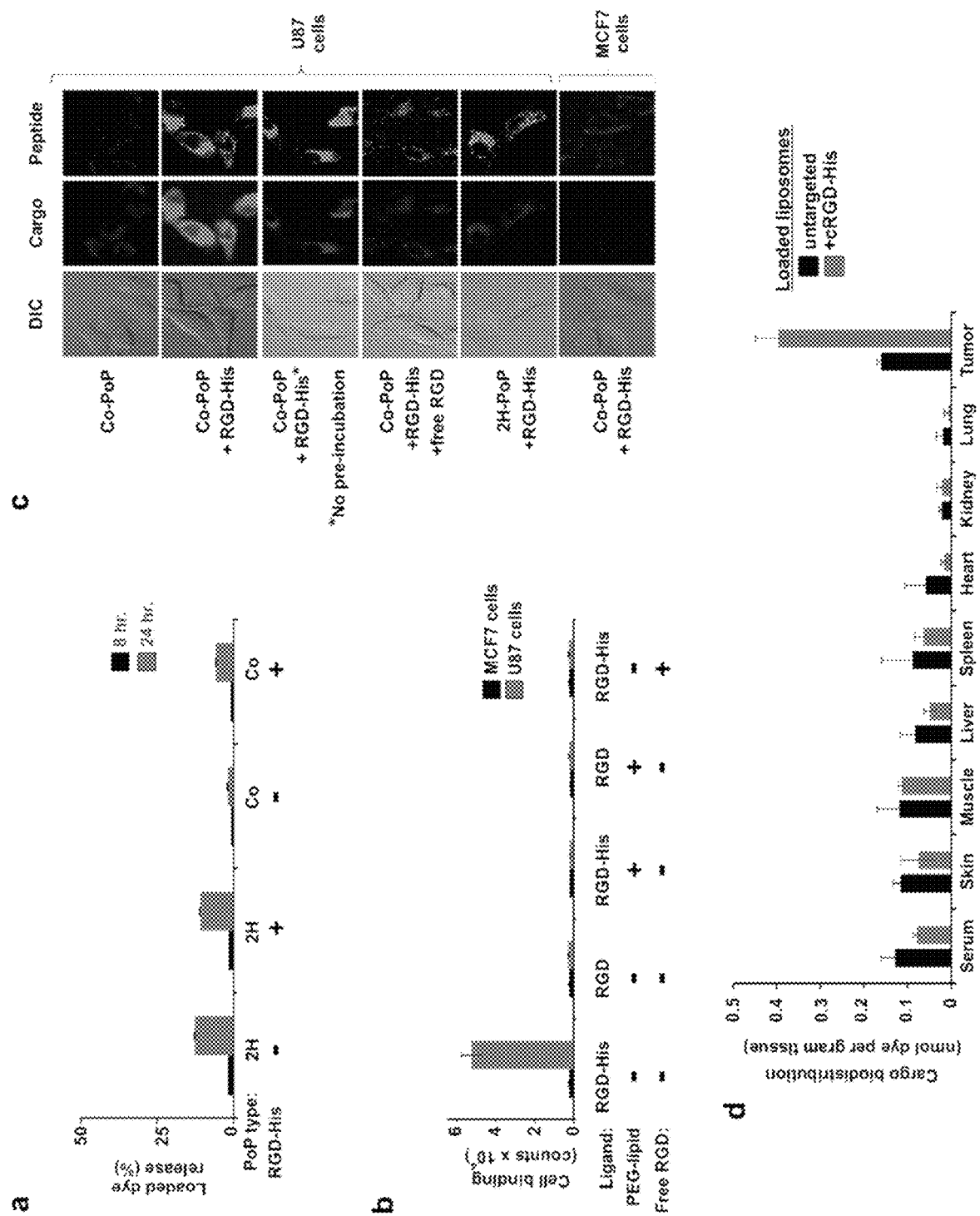
FIG. 5. RGD-His targeting of cargo-loaded liposomes. (a) Release of entrapped sulforhodamine B in PoP liposomes during peptide binding. For each set of bars, the bars from left to right are: 8 hr, and 24 hr. (b) Targeted uptake of sulforhodamine B-loaded liposomes. Cells were incubated in the indicated conditions and uptake was assessed by examining sulforhodamine B fluorescence. For each set of bars, the bars from left to right are: MCF7 cells, and U87 cells (c) Confocal micrographs showing liposome uptake. Cells were incubated with the indicated liposome solutions for 2 hours, washed and imaged. All images were acquired with the same settings. (d) Biodistribution of sulforhodamine B entrapped in CoPoP liposomes with or without attachment of a His-tagged cyclic RGD targeting peptide 45 minutes following injection into nude mice bearing subcutaneous U87 tumors. Mean+/−std. dev. for n=3. For each set of bars, the bars from left to right are: untargeted, and +cRGD-His.
Figure 11:
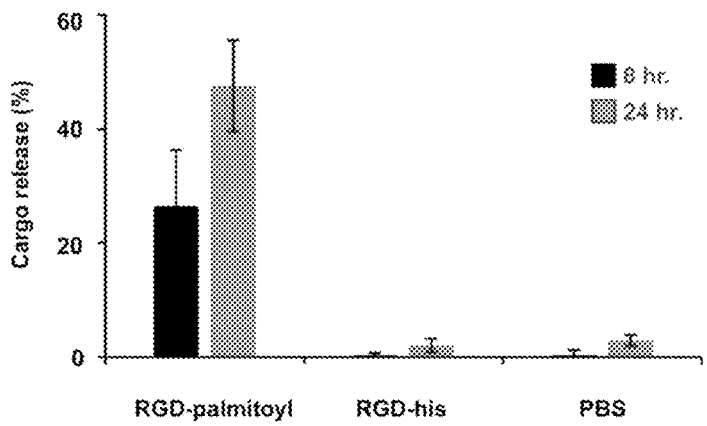
FIG. 11. Membrane permeabilization by lipopeptides. Sulforhodamine B loaded liposomes were incubated with the indicated peptides (5 μg/mL) at room temperature and release was assessed using fluorescence. For each set of bars, the bars from left to right are: 8 hr, and 24 hr.

Given the binding efficacy of the His-tagged peptide to liposomes, bilayer integrity was assessed to determine whether peptide binding induces membrane destabilization. The aqueous core of liposomes was loaded with the fluorophore sulforhodamine B, a water soluble dye, at self-quenching concentrations to probe for membrane permeabilization. As shown in FIG. 5a, dye-loaded liposomes did not release a substantial amount of dye over the 8 hour period in which the peptide had fully bound to the liposomes. At 24 hours, the CoPoP liposomes with the peptide bound released less than 10% of the dye. Thus, His-tag insertion and binding process is sufficiently gentle and non-disruptive so that the bilayer integrity and entrapped cargo remains intact. The analogous palmitoylated lipopeptide resulted in permeabilization of cargo-loaded liposomes upon incubation (FIG. 11), further demonstrating the robustness of the His-tag approach.

Figure 12:
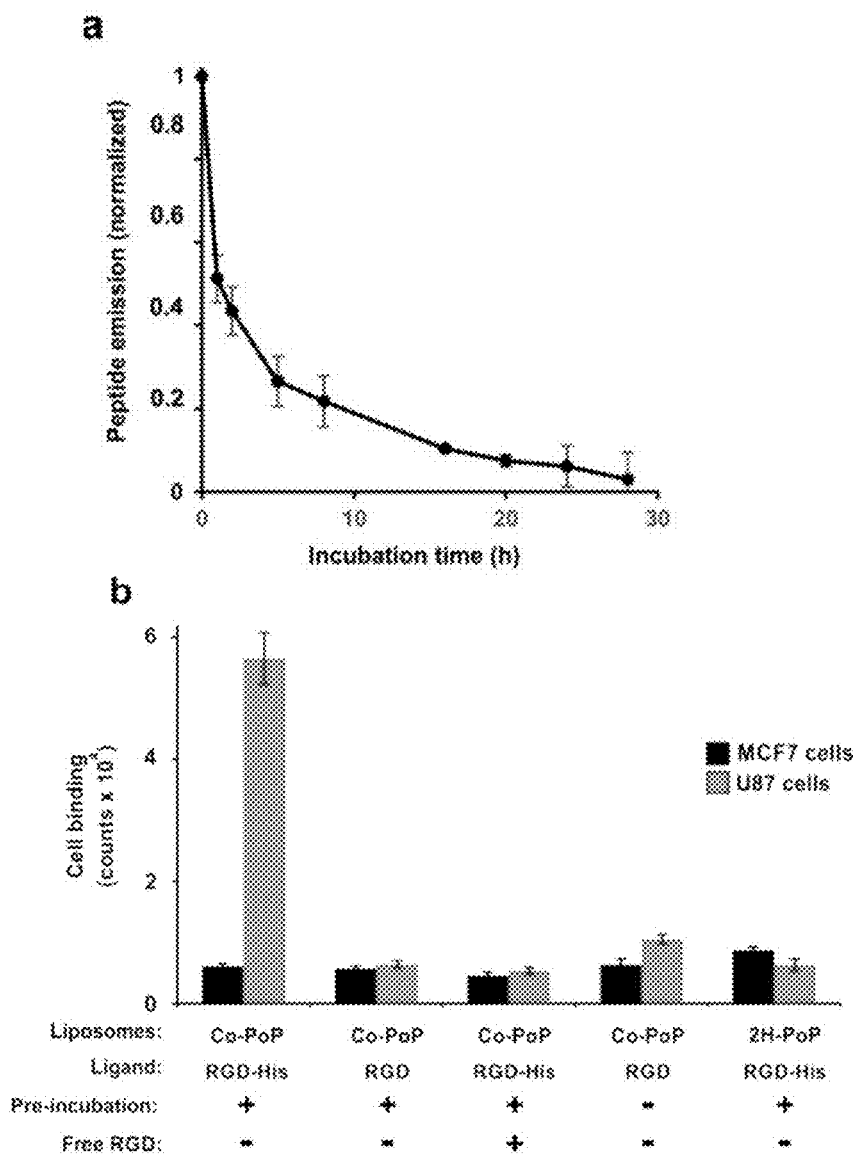
FIG. 12. RGD-His peptide binding to liposomes containing 1 molar % CoPoP and cell targeting. (a) Normalized peptide fluorescence upon incubation with CoPoP liposomes containing 1 molar % CoPoP. Emission was normalized by comparing CoPoP samples with 2H-PoP. (b) Cell uptake of sulforhodamine B liposomes containing 1 molar % CoPoP, incubated with cells as indicated. For each set of bars, the bars from left to right are: MCF7 cells, and U87 cells.

Next, RGD-decorated liposomes were assessed whether they could bind to their molecular targets with the established cell-line pair of U87 glioblastoma cells (RGD-binding) and MCF7 breast cancer cells (RGD non-binding). Following sulforhodamine B entrapment, liposomes were first incubated with the His-tagged RGD peptide and then with both cell lines. Approximately 550 peptides were attached to each liposome. Liposomal uptake was assessed by examining the fluorescence in the cells following washing and lysis (to remove any effects of cargo self-quenching). As shown in FIG. 5b, high liposome uptake was observed in U87 cells incubated with targeted CoPoP liposomes, whereas negligible binding occurred with MCF7 cells. As expected, without the RGD targeting ligand, no uptake occurred in either cell line. Inclusion of PEG-lipid in the liposome formulation resulted in liposomes that did not target to either cell line. It is likely that the presence of the PEG had an effect of obstructing the peptide, which is directly tethered to the bilayer surface. Binding could be inhibited with the presence of excess free RGD peptide, confirming the targeting specificity of the approach. Confocal microscopy substantiated these binding results (FIG. 5c). Although the FAM-labeled peptide was quenched by the PoP liposomes, sufficient signal remained to verify the binding of both the targeting peptide and the liposomal cargo. Both cargo and the peptide were internalized and remained co-localized in U87 cells. When the CoPoP liposomes and targeting peptide were ad-mixed immediately prior to incubation with U87 cells, the targeting peptide itself bound to U87 cells but did not have time to attach to the liposomes, which remained untargeted. The same result was observed for 2H-PoP liposomes which did not bind the peptide. Peptide binding was maintained when liposomes were formed with only 1 molar % CoPoP (FIG. 12a) and maintained selective binding to U87 cells (FIG. 12b). Cargo-loaded liposomes incubated a His-tagged cRGD moiety were intravenously injected into nude mice bearing U87 tumors. As shown in FIG. 5d, 45 minutes after intravenous injection, the targeted liposomes accumulated in tumors with 2.5 fold activity compared to the untargeted liposomes. These data show that CoPoP liposomes can be loaded with cargo in the core of the liposome, be labeled with a His-tagged targeting peptide without inducing cargo leakage, and be directed to molecular receptors expressed on cells expressing specific surface proteins in vitro and in vivo.

Figure 13:
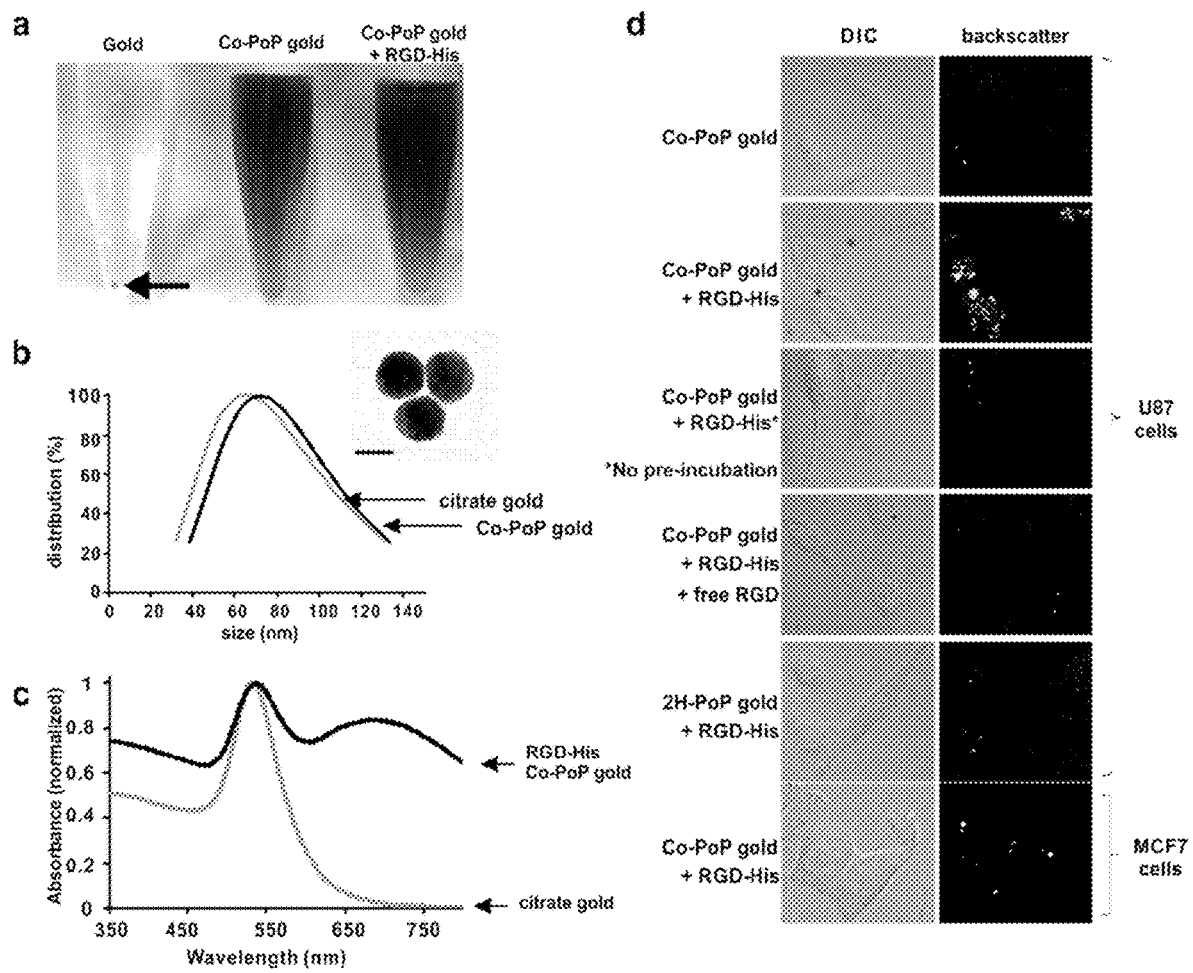
FIG. 13. Coating gold nanoparticles with a CoPoP his-tag binding surface. (a) Photograph of coating protocol to disperse gold nanosphere. Without the PoP coating, citrate stabilized gold aggregates following repeated centrifugation steps (arrow). (b) Size of nanospheres before and after lipid coating. Inset shows transmission electron micrograph of CoPoP gold with 50 nm scale bar. (c) Absorption spectra of citrate stabilized gold and CoPoP gold following RGD-His binding. (d) Confocal reflectance images showing uptake of targeted nanospheres. Cells were incubated with the indicated gold nanospheres for 2 hours, washed and then imaged. All images were acquired with the same settings.

Liposomes represent only a subset of all the types of nanomaterials used in biomedical applications. CoPoP was assessed as a generalized surface coating with selective adhesion for His-tags. Gold nanoparticles were used as a model nanoparticle since these have are used in numerous biological applications. Using an established protocol to lipid-coat gold nanospheres, a citrate-stabilized 60 nm gold dispersion was used to hydrate a thin film of PoP-lipid. Upon repeated centrifugation and re-suspension, the citrate was displaced, causing the nanospheres to aggregate (FIG. 13a). However, in the presence of PoP-lipid, the nanospheres became coated and remained dispersible. Compared to citrate-stabilized gold, PoP-coated nanospheres had a slightly larger hydrodynamic size, corresponding to a bilayer coating on the gold (FIG. 13b). The presence of the coating following His-tag binding did not influence the plasmonic peak of the gold at 540 nm, demonstrating the mild nature of the ligand binding (FIG. 13c). As shown in FIG. 13d, only RGD-His CoPoP-coated gold nanoparticles targeted U87 cells and free RGD inhibited the binding as determined by backscatter microscopy. CoPoP gold alone, as well as 2H-PoP-coated gold with the RGD-His peptide were ineffective at targeting U87 cells.

Development of Antigenic Liposomes.

Many of the monoclonal antibodies that broadly neutralize HIV viral entry, such as 2F5, Z13 and 4E10, target a conserved linear epitope in the membrane proximal external region (MPER) of the gp41 envelope protein, making the MPER a prime target for HIV peptide vaccines. However, it is exposed only during viral entry and attempts to use MPER peptides to generate neutralizing antibodies have faced challenges. This has given rise to the paradigm that vaccination strategies should consider antibody interaction with the lipid bilayer in which the MPER is presented. We have made use of liposomes containing the Toll-like receptor 4 (TLR-4) agonist monophosphoryl lipid A (MPL) combined with liposome-bound MPER peptide sequences. However, the use of a simple anchoring techniques based on biding of MPER His-tagged polypeptides to Ni-NTA liposomes generated low antibody titers. We set out to examine if the same approach could be enhanced with CoPoP liposomes.

Figure 6:
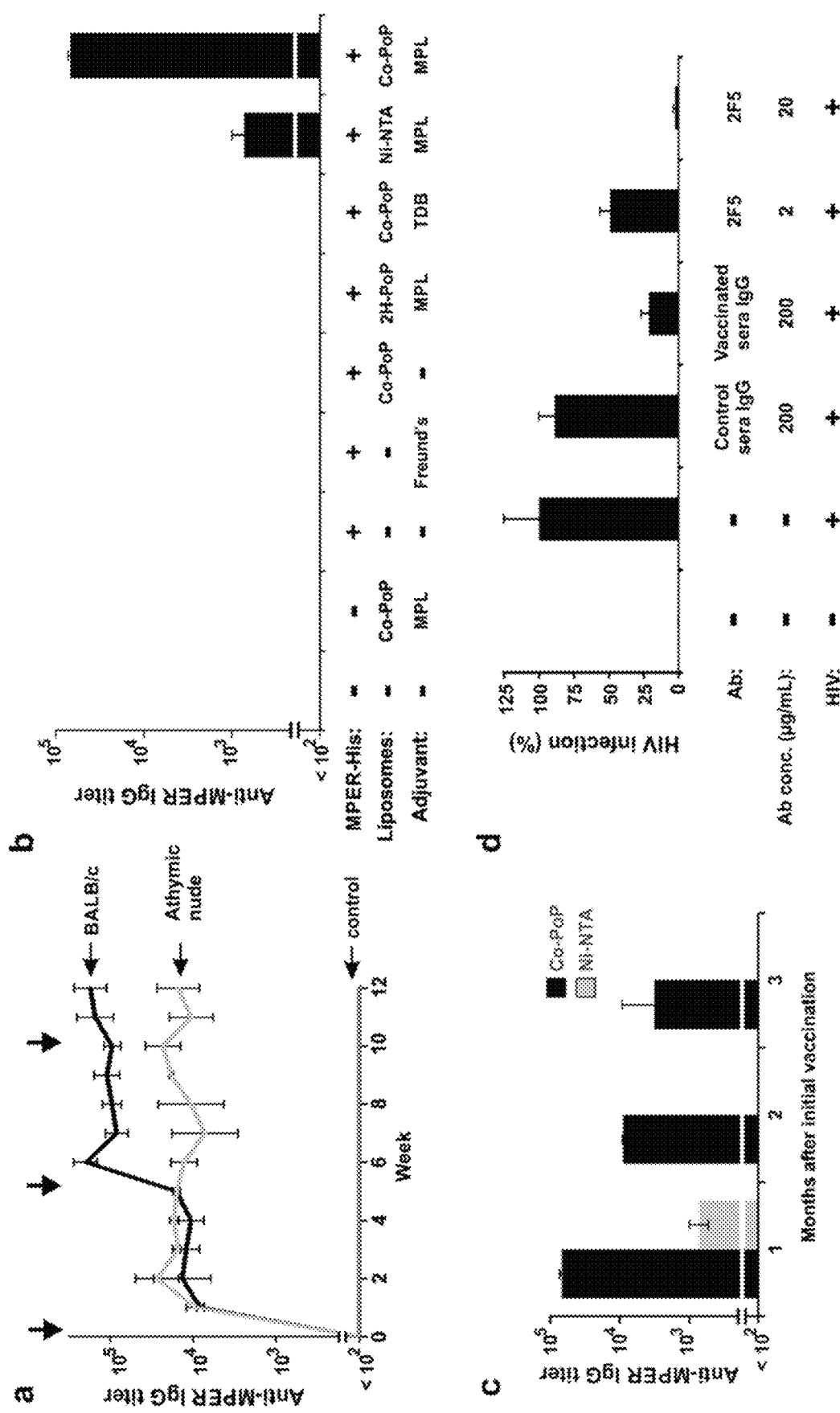
FIG. 6. HIV peptide vaccination using immunogenic CoPoP liposomes. (a) BALB/c or athymic nude mice were immunized with CoPoP liposomes containing a 25 μg of MPL and 25 μg of His-tagged MPER peptide derived from the HIV gp41 envelope protein. Sera titer was assessed with an ELISA using a biotinylated MPER peptide lacking a His-tag and probed with an anti-IgG secondary antibody. Arrows indicate time of vaccinations. (b) Anti-MPER titer in BALB/c mice vaccinated as indicated. Mice were vaccinated on week 0 and week 2 and serum was collected on week 4. (c) Sustained anti-MPER titer in mice vaccinated with CoPoP liposomes containing MPL. Mean+/−std. dev. for n=4 mice per group. The first two bars (joined) on the left are CoPoP and Ni-NTA (d) Neutralization of HIV infection in 293 cells in the presence of indicated antibodies. IgGs were purified from mouse sera using Protein A. Mean+/−std. dev. for n=3.

A liposomal-peptide vaccination system was used with the MPER-His sequence NEQELLELDK-WASLWNGGKGG-HHHHHH (SEQ ID NO:11). The MPER-His peptide was bound to CoPoP liposomes containing MPL. A single injection containing 25 μg MPER-His and 25 μg of MPL was administered to BALB/c mice and to athymic nude mice. This elicited a titer on the order of $10^4$ in both BALB/c mice and nude mice, demonstrating a strong humoral immune response (FIG. 6a). This may be significant since HIV infects helper T cell populations, making B cell mediated responses important. Following a booster injection, the anti-MPER titer in athymic nude mice was unaffected, but in healthy mice there was a titer increase by an order of magnitude, demonstrating a T cell-mediated memory effect. Thus, the vaccination protocol resulted in both B cell and T cell-mediated immunity.

Next, various vaccine components were examined to better determine the specificity of the immune response (FIG. 6b). The MPER-His peptide did not elicit any antibodies when injected on its own, in Freund's complete adjuvant or along with 2H-PoP liposomes containing MPL. Interestingly, when the peptide was administered with CoPoP liposomes lacking MPL, no antibodies were generated whatsoever. Another lipid adjuvant, trehalose dibehenate (TDB) also failed to elicit any antibody production. TDB does not act on TLR-4, which underscores the importance of MPL in immune activation of the liposomal vaccine system. When MPER-His bound to Ni-NTA liposomes were used, a weak antibody titer of less than $10^3$ was achieved, consistent with previous reports. However, when CoPoP lipsoomes were used, a stronger response by 2 orders of magnitude was observed. Presumably, the stable binding of the peptide to the liposomes in vivo is directly responsible for this effect. The CoPoP immunization strategy was effective, with antibody titers persisting for at least 3 months, whereas no antibodies were detected with Ni-NTA liposomes after one month (FIG. 6c).

Post vaccination sera from mice was pooled and purified using Protein G agarose to yield purified IgG. This was then used to assess inhibition of viral entry by HIV (FIG. 6d). When the purified IgG from vaccinated mice was used at a final concentration of 0.2 mg/mL, viral entry was inhibited by more than 75%. This efficacy of inhibition is greater than that of the broadly neutralizing monoclonal antibody 2F5 when incubated at a concentration of 2 μg/mL but less than and 20 μg/mL. These data show the potential for a vaccination approach making use of CoPoP liposomes with HIV-derived peptides in order to induce antibody generation that can prevent viral entry.

Example 2

In this example, a vaccine was developed that made use of his-tagged Pfs25, a recombinant protein derived from *Plasmodium falciparum* and liposomes containing CoPoP and MPLA.

Liposome Preparation. For generation of CoPoP and 2H-PoP liposomes, 1,2-dimyristoyl-sn-glycero-3-phosphocholine (DMPC), cholesterol (CHOL), monophosphoryl lipid A (MPLA) and CoPoP (or 2H-PoP) were dissolved in chloroform at the indicated molar ratio (Table 2). A dried lipid film was formed after $N_2$ stream and vacuum overnight and was rehydrated in PBS to a final lipid concentration of 3 mg/mL. The liposomal suspension was subjected to 11 times freeze/thaw cycles using ice cold $CO_2$/acetone and a water bath followed by extrusion 10 times at 60° C. through 200 nm polycarbonate membranes.

The Psf25 insect protein (Recombinant subunit Pfs25 purified from super sf9 cells, concentration determined by BCA assay as 1 mg/mL) was combined with liposomes overnight (20 h) at 4° C. Psf25 incubated in $H_2O$ served as a control. BSA was combined with liposomes as a negative control. The binding of Psf25 protein and liposomes was determined by a micro-centrifugal filtration method.

TABLE 2

Formulation of Psf25 CoPoP/MPLA liposomes for each mouse injection

| Each mice injection dose | DMPC | CHOL | CoPoP | MPLA | Psf25 |
|---|---|---|---|---|---|
| Molar ratio | 55 | 35 | 5 | 5 | |
| μg/50 μl | 84.6 | 30.7 | 12.1 | 20.0 | 5/0.5/0.05 |
| nmole | 127.75 | 79.39 | 11.34 | 11.34 | 0.25/0.025/0.0025 |

Microcentrifugal filtration for binding. Psf25 protein with CoPoP, Psf25 protein with standard PoP (no cobalt) and Psf25 protein with water were placed into Nanosep Centrifugal Devices (100K, OMEGA). The device was rinsed with $QH_2O$ and centrifuged at 1100 rpm for 3 min before use. Each of the samples was added and spun for 3 min at 1400 rpm. The device was washed twice with $QH_2O$ and centrifuged at 1400 rpm for 3 min (minutes). The sample from the bottom filtrate was collected and the protein concentration was analyzed by BCA assay measuring absorbance at 562 nm (Thermo cat. 23235).

Vaccinations. On days 0 and 21, CD-1 mice (8 week females, Envigo) received intramuscular injections (i.m.) of 5, 0.5 and 0.05 μg Psf25 protein. Where indicated, the injections also included 20 μg MPLA incorporated into the liposomes (Avanti No. 699800P). ISA720 was also used as an adjuvant incubated with 5 μg Psf25 protein. The treatment groups and flow chart are shown in Table 3.

TABLE 3

Treatment groups for serum IgG titer (n = 10 mice per group).

| | CoPoP/MPLA | Psf25 (ug) | ISA720 |
|---|---|---|---|
| Group 1 (G1) | + | 5 | − |
| Group 2 (G2) | + | 0.5 | − |
| Group 3 (G3) | + | 0.05 | − |
| Group 4 (G4) | + | 0 | − |
| Group 5 (G5) | − | 5 | − |
| Group 6 (G6) | − | 5 | + |

Serum anti-Psf25 IgG level by ELISA. Anti-Psf25 titer was assessed by enzyme-linked immunosorbent assay (ELISA) in 96-well plates (Thermo, Maxisorp). His-tagged Psf25 (0.1 μg) in 100 μl coating buffer (3.03 g $Na_2CO_3$ and 6.0 g $NaHCO_3$/1 L distilled water, pH 9.6) was incubated in the wells for overnight at 4° C. Wells were washed with PBS containing 0.1% Tween (PBS-T) for 3 times and block with PBS containing 0.1% casein (PBS-C) and then incubated for 2 h. Wells were wash with then washed with PBS-T for 3 times and goat anti-mouse IgG-HRP (GenScript No. A00160) was diluted in PBS-C to become 1 μg/ml and added to each well. The wells were washed again with PBS-T for 6 times before the addition of tetramethylbenzidine (Amresco No. J644).

Results.

Figure 14:
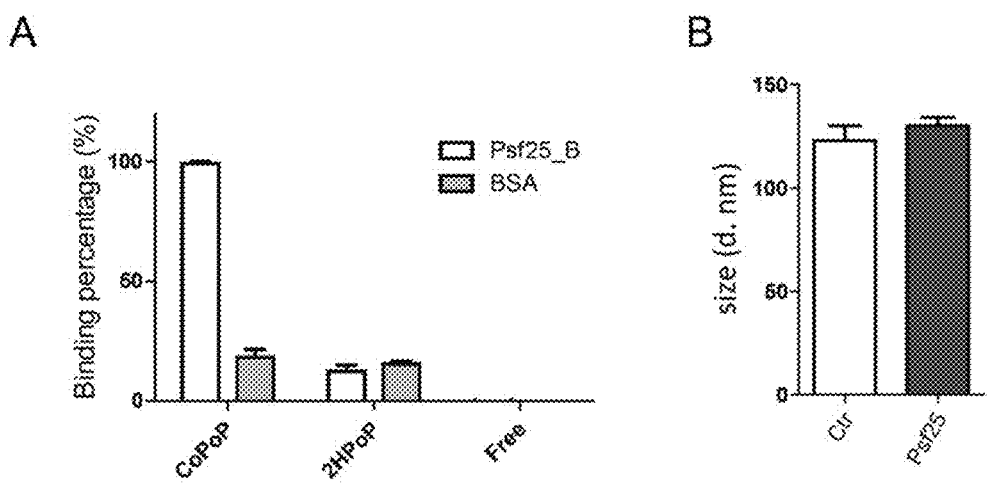
FIG. 14. (A) Psf25 (Pfs25_B) binding was measured by a centrifugal filtration assay. These data indicate 100% binding of the Psf25 protein to Co-pop liposomes. (B) Particle size of CoPoP liposomes before and after Psf25 protein binding.
Figure 15:
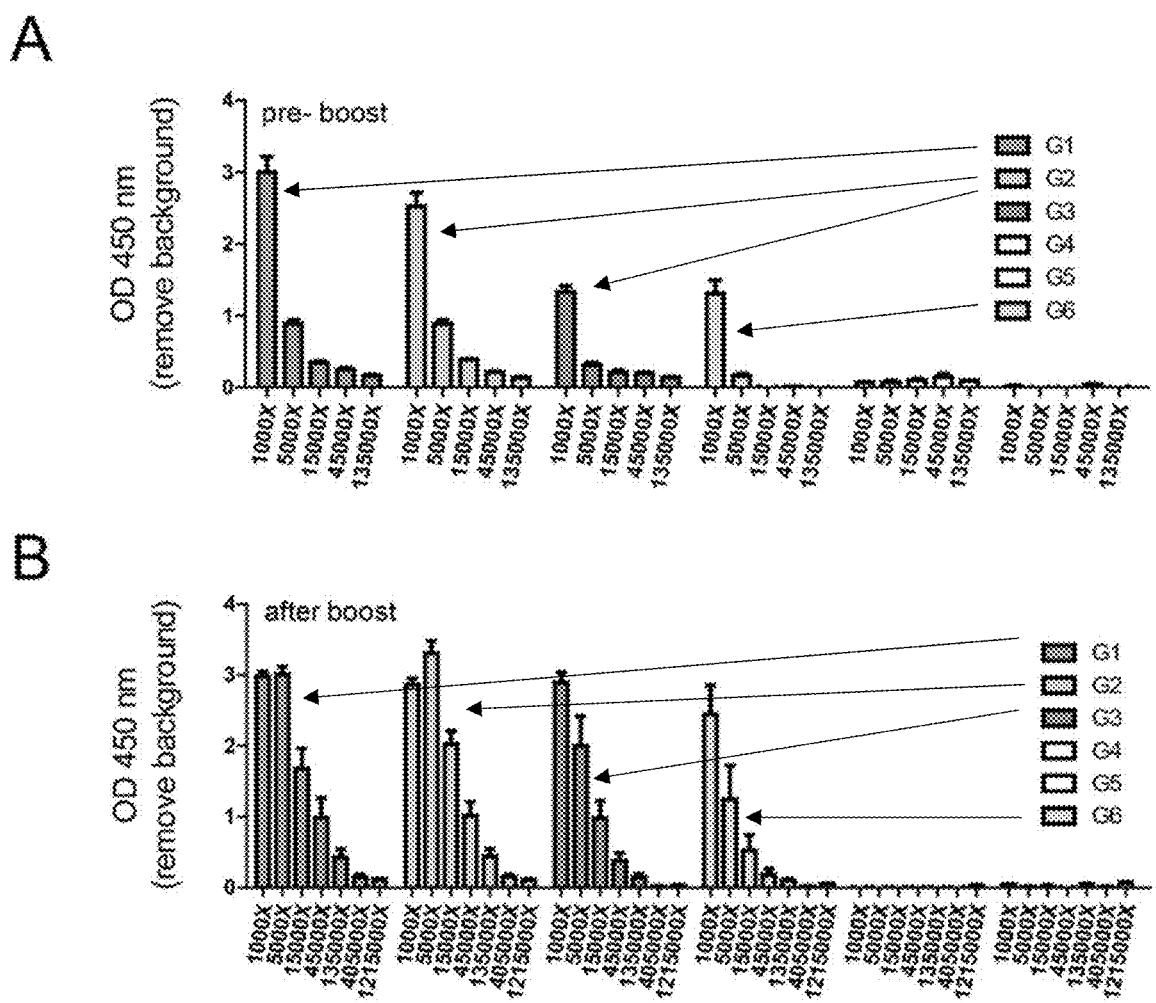
FIG. 15. Anti-Psf25 IgG levels in CD-1 mice. Mice were vaccinated with Psf25 in CoPoP/MPL or ISA70 following intramuscular injections with (A) pre-boost and (B) after boost, three-week prime/three-week boost (5, 0.5 or 0.05 ug Pfs25 per injection). IgG titers were measured by ELISA on a 96-well plates from mice vaccinated with CoPoP (Psf25) liposomes, or free Psf25 protein (with or without ISA70). Data show mean+/−S.D. with n=5 mice per group).
Figure 16:
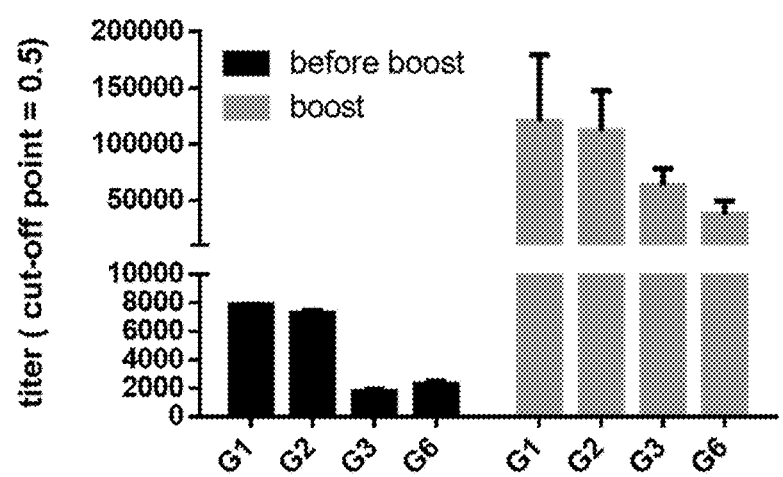
FIG. 16. Anti-Psf25 IgG titers. Titers were defined as reciprocal serum dilution that produced an absorbance greater than 0.5 over background.
Figure 17:
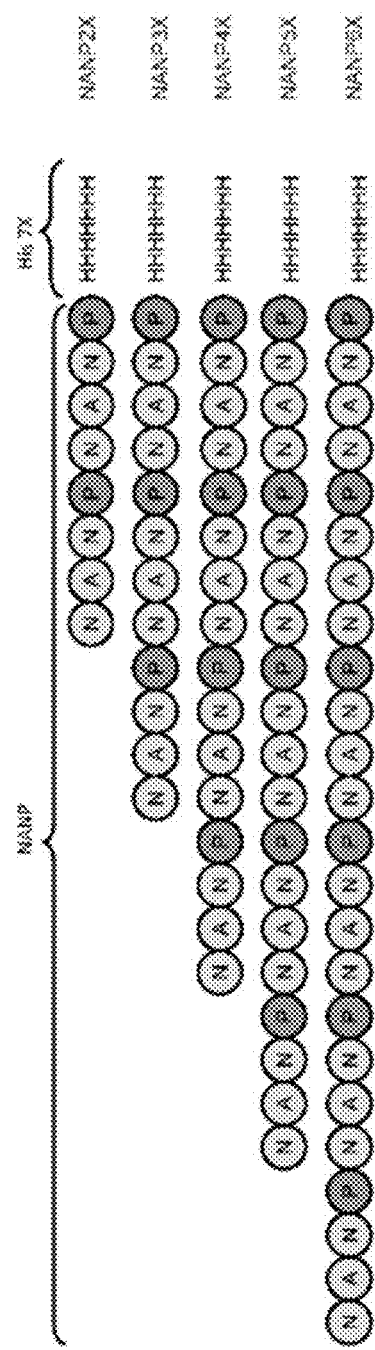
FIG. 17. Illustration and characterization of different length of NANP peptide coating on CoPoP liposomes. (A) Different numbers of NANP repeated peptide containing 7× histidine (His) tag. (B) Mean diameter and polydispersity (PDI) of CoPoP liposomes conjugated with different length of NANP peptide were calculated by dynamic light scattering (n=3). Error bars, SD. (C) peptide binding of NANP peptides to CoPoP liposomes and 2HCoPoP liposomes were measured by the microcentrifugal filtration process and BCA assay (n=3).
Figure 17:
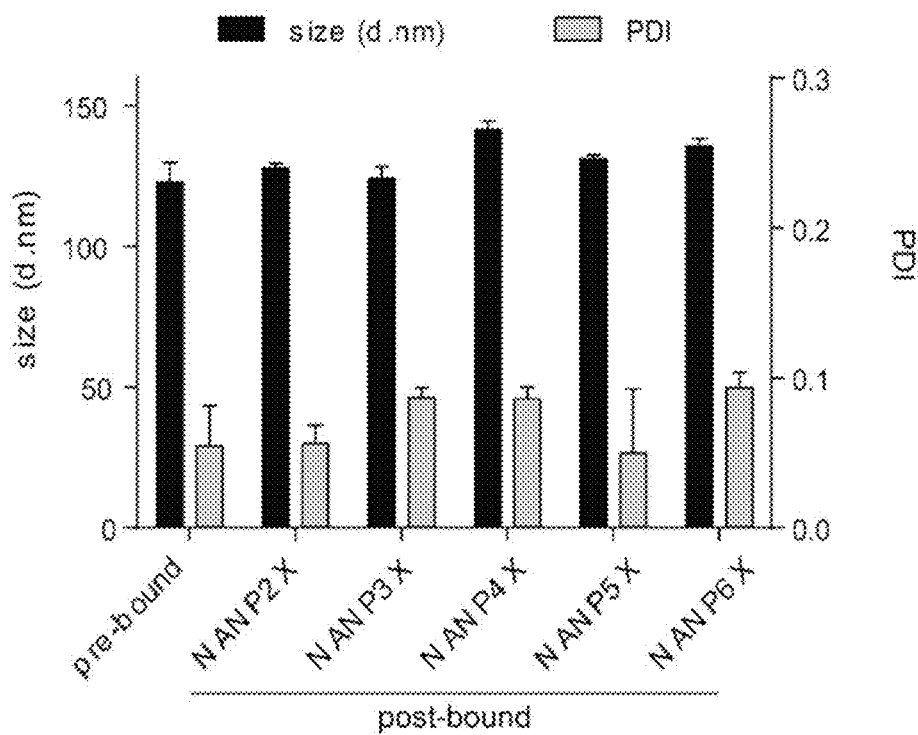
Figure 17:
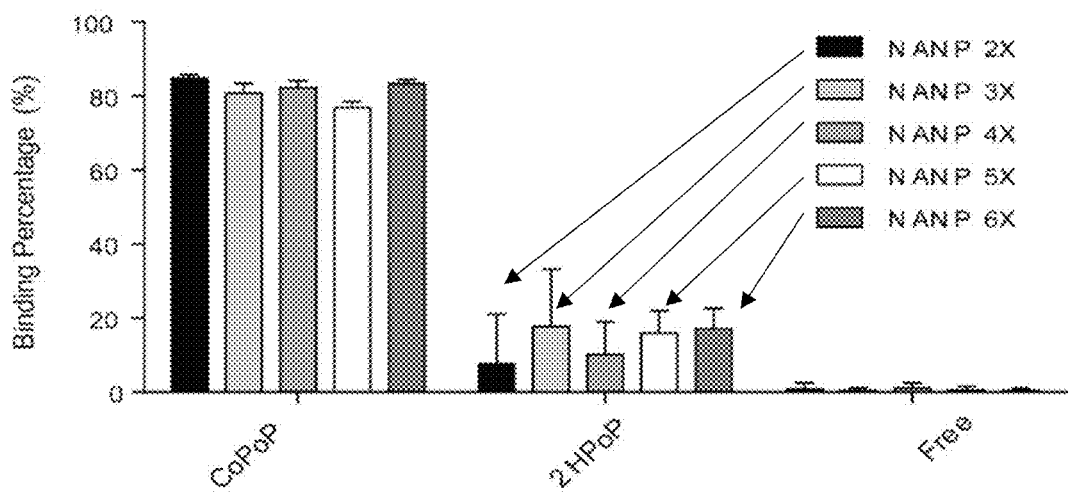
Figure 18:
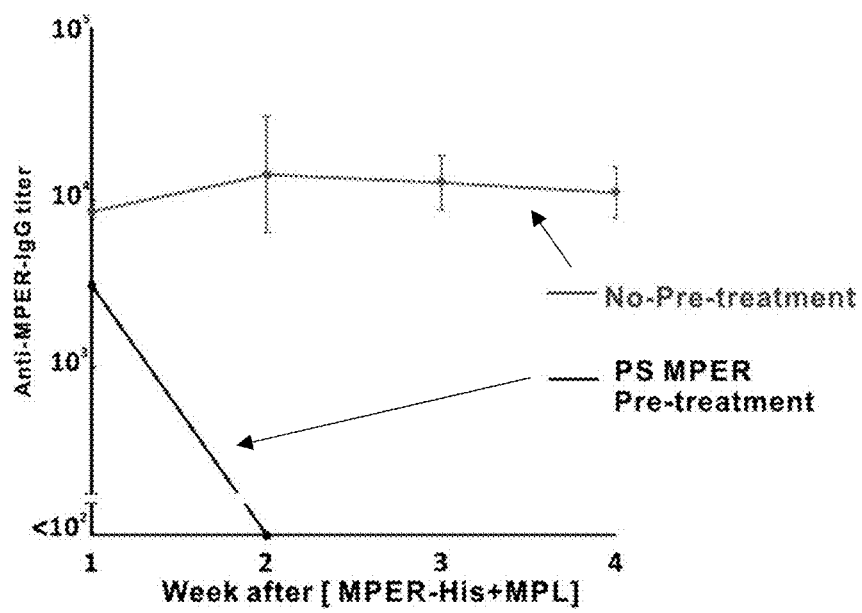
FIG. 18. Anti MPER IgG titers in mice pretreated with CoPoP/phosphatidyl serine liposomes bound to his-tagged MPER. Mice were pretreated MPER/CoPoP/PS liposomes 4 weeks and 2 weeks prior to injection of MPER in CoPoP/MPLA liposomes to induce an antibody response against MPER.

Characterization of liposomes and protein binding binding ability after Psf25 protein coated. The average size of the CoPoP liposomes before and after Psf25 protein binding was measured by dynamic light scattering was 122.9 and 139 nm, respectively (FIG. 14A), with similar polydispersity indexes around 0.05, showing favorable liposome size after binding with high monodispersity. Furthermore, to investigate if the Psf25 protein bound efficiency and specifically to CoPoP liposomes, we incubated Pfs25 with CoPoP liposomes or 2H-PoP liposomes at 4° C. overnight, followed by microcentrifugal filtration to determine protein binding to liposomes. Based on the amount of Pfs25 in the filtrate as detected by BCA assay, most of the Psf25 bound CoPoP liposomes (99.27%) but not the 2H-Pop liposomes (12.33%). The binding of Pfs25 to CoPoP liposomes was ~99% (FIG. 14A).

Anti-Pfs25 IgG levels.

CD-1 mice were vaccinated with the CoPoP/MPLA/Pfs25 liposomes conjugated with or without Psf25 (with concentration of 5, 0.5 and 0.05 μg); via i.m. or with free Psf25 (with or without ISA70) on day 0 (prime) and day 21 (boost). On day 20 and 42, serum was collected and anti-Psf25 IgG titers were determined by ELISA (FIG. 15A and FIG. 15B). Mice preboost with the CoPoP/MPLA/Psf25 liposomes showed similar IgG level in serum in both 5 μg and 0.5 μg Psf25 conjugated groups. Different dilutions (starting at 1/1000) of anti-Psf25 IgG-serum sample were tested by the Psf25 (plant) ELISA for each treatment groups (Table 3). Here, the cutoff point was set at O.D. equal to 0.5. The data shows that the IgG titer changed from 1/5000 to 1/45000 after boosting in G1, as well as in G2, which represent CoPoP/MPLA/Pfs25 liposomes conjugated with 5 or 0.5 μg Psf25 protein (Table 3). On the other hand, the IgG titer of CoPoP/MPLA/Pfs25 liposomes conjugated with 0.05 μg Psf25 protein switch from 1/1000 to 1/15000 after boosting, similar results were shown in G6, which represent the 5 μg Psf25 protein incubated with ISA70. This data is also reflected in FIG. 16, which shows titers of 0.05 ug Pfs25 in CoPoP/MPLA liposomes producing a higher titer than 5 μg Pfs25 in ISA720.

Example 3

In this example, a liposomal vaccine was developed that made use of synthetic his-tagged peptides containing repeating NANP sequences, which are derived from the circumsporozoite protein of *Plasmodium falciparum*. The liposomes had the same composition as Example 1, but peptides instead of protein were used. The peptides examined are shown in FIG. 17A. The average size of the CoPoP liposomes before and after different NANP binding was measured by dynamic light scattering was 122.9 and 139 nm, respectively (FIG. 17B), with similar polydispersity indexes around 0.05, showing favorable liposome size after binding with high monodispersity. Furthermore, to investigate if the NANP peptide bound efficiency and specifically to CoPoP liposomes, we incubated NANP peptide with CoPoP liposomes or 2H-PoP liposomes at 4° C. overnight, followed by microcentrifugal filtration to determine peptide binding to liposomes. Based on the amount of peptide in the filtrate as detected by BCA assay, a large amount of the NANP bound CoPoP liposomes (~80% in different length of peptides) but not the 2H-Pop liposomes (less than 20%). The binding of NANP to CoPoP liposomes was ~80% in all different length of peptides. (FIG. 17C)

Example 4

In this example, CoPoP liposomes containing phosphatidylserine (PS) was used to reduce antibody response to his-tagged presentation molecules. Liposomes were formed with 10:30:30:30 CoPoP:phosphatidylserine:DOPC:Cholesterol via thin film hydration and extrusion. His-tagged MPER was then bound to the liposomes. These PS liposomes were injected via footpad to mice 4 weeks and 2 weeks prior to vaccination with CoPoP/MPLA liposomes decorated with MPER. As shown in FIG. 18, pretreatment with PS liposomes resulted in decreased IgG titers against MPER.

Example 5

Figure 19:
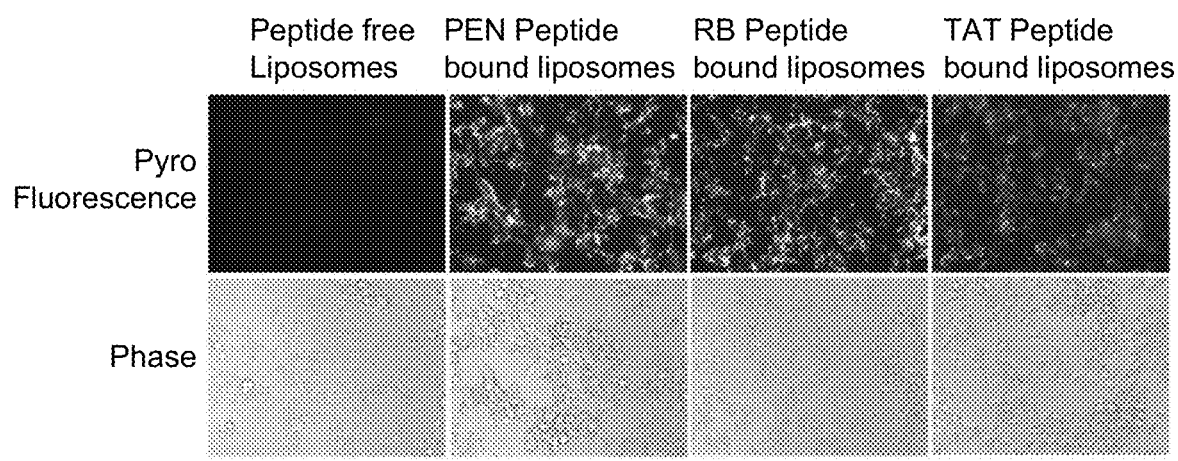
FIG. 19. Fluorescence of U87 cells following incubation with CoPoP liposomes bound to various his-tagged CPPs.
Figure 20:
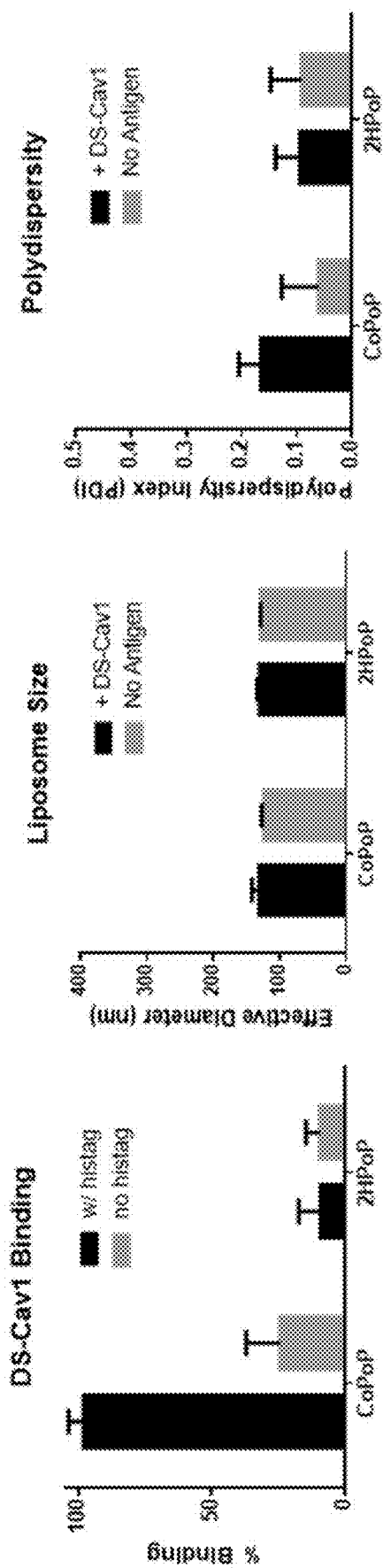
FIG. 20. After incubating at room temperature for 2 hours, DS-Cav1 bearing a his-tag achieved near complete binding with CoPoP nanoparticles (FIG. 20, left). His-tagged DS-Cav1 did not bind significantly to PoP particles lacking cobalt (2HPoP), and DS-Cav1 without the his-tag present did not achieve significant binding with either particle. His-tagged DS-Cav1 did not induce liposome aggregation upon binding based on liposome diameter (FIG. 20, center) or polydispersity (FIG. 20, right).

In this example, CoPoP liposomes were targeted to cells via his-tagged cell penetrating peptides. The following his-tagged cell penetrating peptides were obtained: HHHHHHHHGRKKRRQRRRPPQ (SEQ ID NO:13) (TAT peptide); HHHHHHHHRRRRRRRR (SEQ ID NO:14) (R8 peptide); HHHHHHHRQIKIWFQNRRMKWKK (SEQ ID NO:15) (PEN peptide). As shown in FIG. 19, following straightforward aqueous incubation with CoPoP liposomes containing [2:5:30:63] [PoP:CoP:CHOL:DMPC], these liposomes could bind and get uptaken following 1 hour incubation with U87 cells.

Example 6

In this example, CoPoP liposomes were used with a pre-fusion RSV antigen (a his-tagged antigen, DS-Cav1 for RSV). His-tagged antigens can be used with the CoPoP/PHAD system for generating functional antibodies.

The antigen DS-Cav1 is a pre-fusion form of the F protein on the surface of the RSV virus. His-tagged DS-Cav1 has been show to induce neutralizing antibodies to RSV A2.

CoPoP liposomes bind his-tagged proteins with simple mixing of antigen and liposomes, so that the resulting liposomes become decorated with conformationally-intact antigens, presented in a uniform orientation. The antigen binding is non-covalent stable in biological environments. It was shown (with another his-tagged antigen, Pfs25, a malaria transmission blocking antigen) that CoPoP liposomes result in improved antigen delivery to antigen presenting cells in vitro and in vivo.

It was showed that his-tagged DS-Cav1 effectively binds to CoPoP liposomes. A 50 µL volume of antigen-liposome solution is prepared using CoPoP and PoP (also referred to as 2H) and diluted to 200 µL. Reference samples of liposomes without antigen, and antigen without liposomes, were also prepared. Samples were centrifuged at 20,000 rcf for 90 minutes, and the supernatant was extracted from the resulting liposome pellet. An equal volume of BCA was added, to a total volume of 400 µL. Samples were then incubated in a water bath at 60° C. for 10 minutes. A volume of 100 µL of each sample are transferred to each of 3 wells of a 96-well plate and the absorbance was measured at 562 nm. The absorbance difference between the antigen-liposome supernatant and liposome-only reference samples were used to calculate the percentage binding, with higher absorbance corresponding with a higher protein concentration in the supernatant and thus a lower binding.

Figure 21:
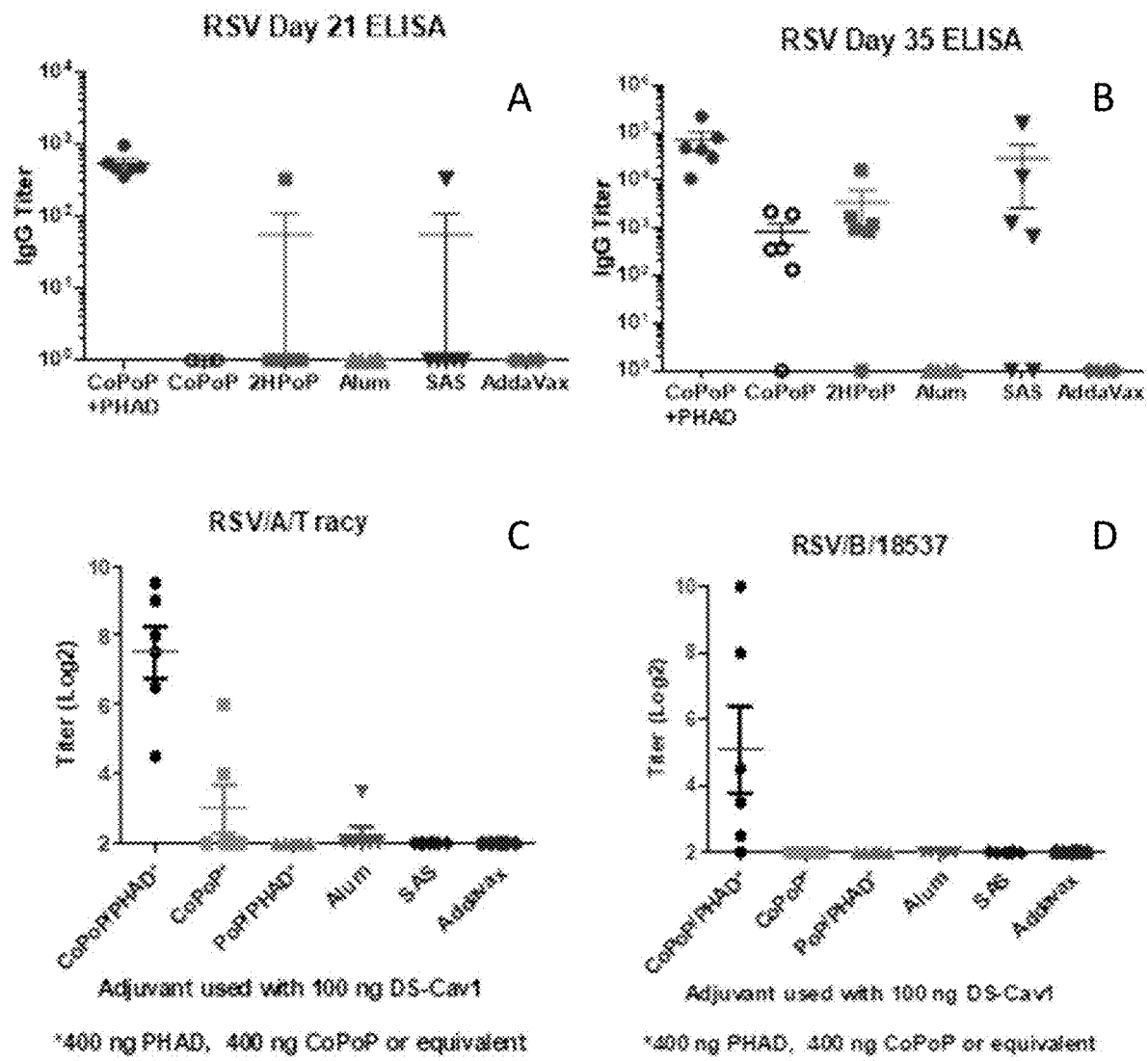
FIG. 21. CoPoP/DS-Cav1 vaccination results in higher IgG antibody titer both before and after booster injections. At 35 days post-primary injection, CoPoP vaccine achieves the greatest RSV neutralization. CD-1 mice were intramuscularly injected with 100 ng DS-Cav1 on day 0 and day 21 and serum was collected on day 42 and assessed for neutralization.

Mice were then injected with RSV antigen in conjunction with one of six adjuvants: CoPoP with PHAD, CoPoP without PHAD, 2HPoP with PHAD, aluminum hydroxide (Alum), Sigma Adjuvant System (SAS), and AddaVax. When mice were vaccinated with RSV, all mice injected with the RSV vaccine containing CoPoP/PHAD particles exhibited detectable IgG antibody titers prior to the booster vaccination (FIG. 21A). In contrast, only a total of two mice from the remaining five groups exhibited detectable IgG titers. Two weeks after the booster vaccination the IgG titers of mice vaccinated with CoPoP, 2HPoP, and SAS all showed significant increase; however, CoPoP with PHAD remained the most effective formulation for inducing antibody production (FIG. 21B). The mean antibody titer for the CoPoP/PHAD group exceeded the other five groups, and the CoPoP/PHAD was the only group without mice that were unresponsive to the vaccine after the booster injection.

An RSV neutralization assay was performed using serum taken from mice 35 days after the primary injection (FIG. 21C,D). The results of the assay indicate that the antibodies produced in response to the CoPoP/PHAD vaccine are significantly more effective at neutralizing RSV type A and B than any other vaccine group. From the data, it was concluded that CoPoP/PHAD performs favorably compared to alternative adjuvants such as Alum, SAS, and AddaVax. Furthermore, the neither the CoPoP liposomes nor PHAD adjuvant component of CoPoP alone are sufficient to increase effectiveness; these results can only be attributed to the combined effects of the novel CoPoP/PHAD formulation.

Example 7

In this example, CoPoP liposomes were used with OspA, a Lyme disease antigen. His-tagged antigens can be used with the CoPoP/PHAD system for generating functional antibodies.

Figure 22:
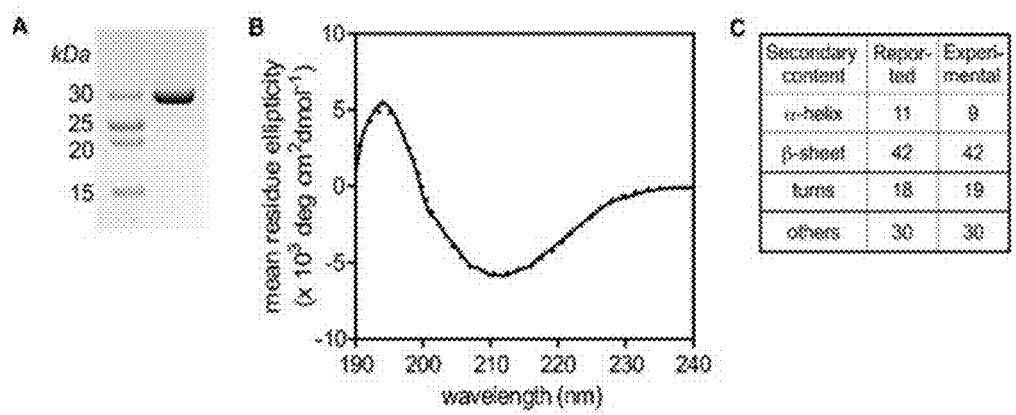
FIG. 22. Generation of his-tagged OspA.

OspA is a lyme disease antigen. A his-tagged OspA based on the B31 strain protein sequence without the lipid tail was generated, and purified it as shown in FIG. 22.

Figure 23:
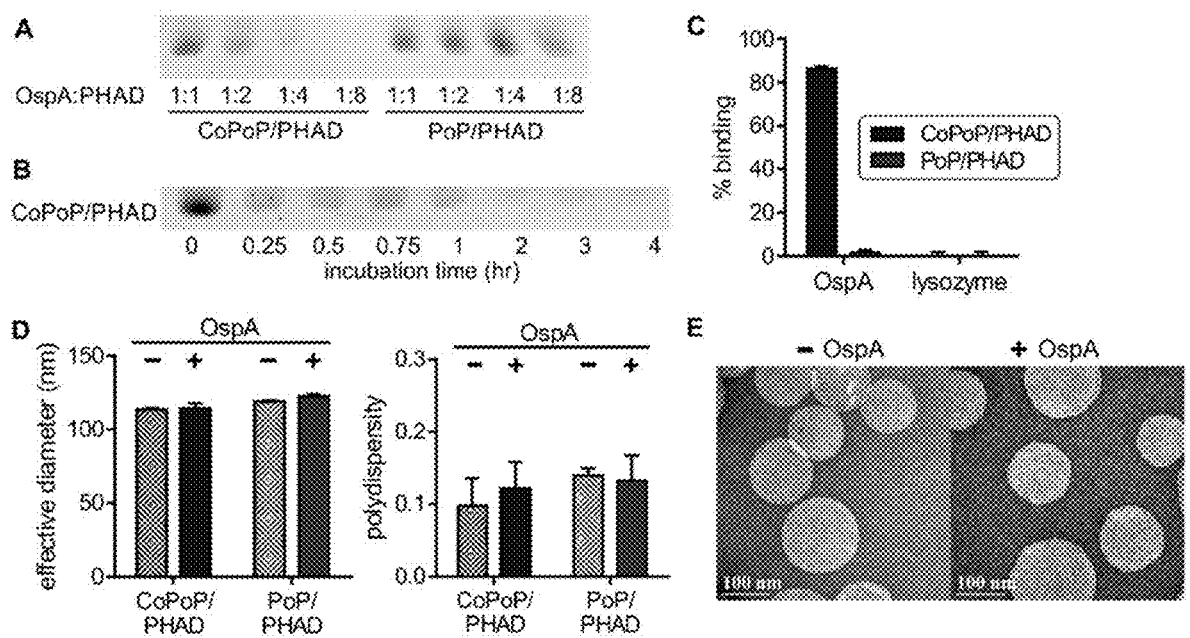
FIG. 23. Characterization of an OspA-based proteoliposome formed using CoPoP/PHAD liposomes. (A) Optimum binding mass ratio of OspA:CoPoP/PHAD liposomes evaluated by native PAGE (histidine-MOPS buffer system pH 6.8). (B) Kinetics of OspA binding to CoPoP/PHAD liposomes incubated at 1:4 mass ratio at room temperature. (C) Specific binding of his-tagged OspA to CoPoP/PHAD liposomes measured by microBCA assay of supernatant obtained from high-speed centrifugation of liposomes. (D) Hydrodynamic diameter and polydispersity index of liposomes measured using dynamic light scattering. (E) TEM images of CoPoP/PHAD liposomes with and without bound his-tagged protein. Acquisitions were made 3 hr after incubation of liposomes with protein. Error bars represent standard deviations for n=3 measurements.

Spontaneous formation of the proteoliposomes occurs via insertion of the histidine tag into the hydrophobic bilayer and subsequent coordination of the imidazole moiety to the metal center. Binding conditions for were evaluated using native electrophoresis, which allows physical separation of liposome-bound and free proteins due to the limiting pore size of the acrylamide gel. Observed optimum binding mass ratio of 4:1 of PHAD:OspA (FIG. 23A) is consistent with previous studies using the malaria antigen, Pfs25. Incubating 80 µg/mL OspA with an equal volume of 320 µg/mL CoPoP liposomes requires three hours of incubation at room temperature (FIG. 23B). Visual inspection of the acrylamide gel showed that kinetics of binding started to plateau after 15 min likely due to steric hindrance for subsequent binding to nearby unconjugated sites. It can be deduced that the initial phase of binding occurred at a fast rate based from the relative band intensities for time points, 0 and 15 min. At the particleization conditions, specific binding is estimated to be about 80% based from microBCA assay of the supernatant obtained from high speed centrifugation (FIG. 23C). Using the same method, low non-specific binding was observed for PoP/PHAD liposome, which lacks the chelating metal. A non-histidine tagged protein, lysozyme, failed to bind to neither CoPoP/PHAD nor PoP/PHAD liposomes. Based from DLS measurements, post-incubation liposomal size remains essentially the same for both CoPoP/PHAD and PoP/PHAD liposomes (FIG. 23D). Moreover, transmission electron micrographs revealed that CoPoP/PHAD liposomes retained its shape after antigen binding (FIG. 23E).

Figure 24:
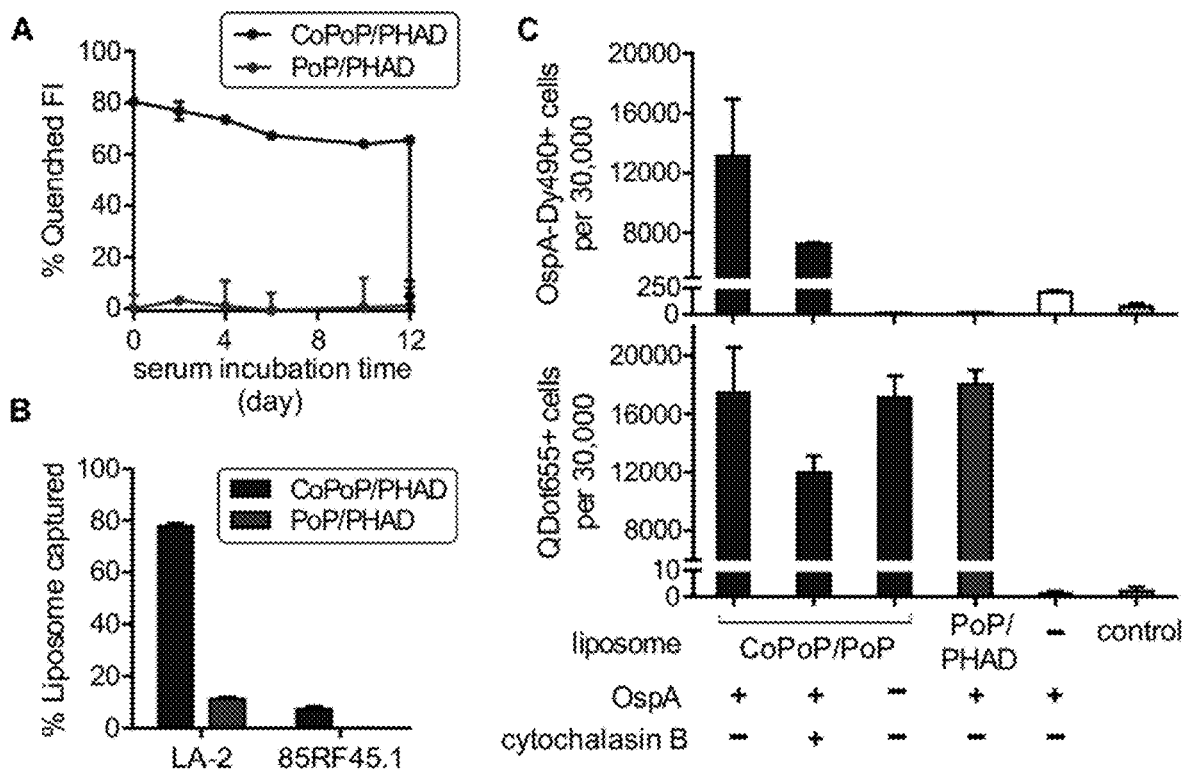
FIG. 24. Assessing epitope availability and stability of antigen-functionalized nanoliposomes. (A) Stability of nanoliposome-antigen particles in 20% (v/v) human serum based on fluorescence quenching assay. (B) Immunoprecipitation of OspA-bound liposomes by OspA-specific monoclonal antibody LA-2. (C) DY-490-OspA uptake by murine RAW 264.7 macrophage cells following 2 hr incubation with indicated samples. Cytochalasin B was supplemented to medium 1 hr prior to incubation. Error bars represent standard deviations for n=3 experiments.
Figure 25:
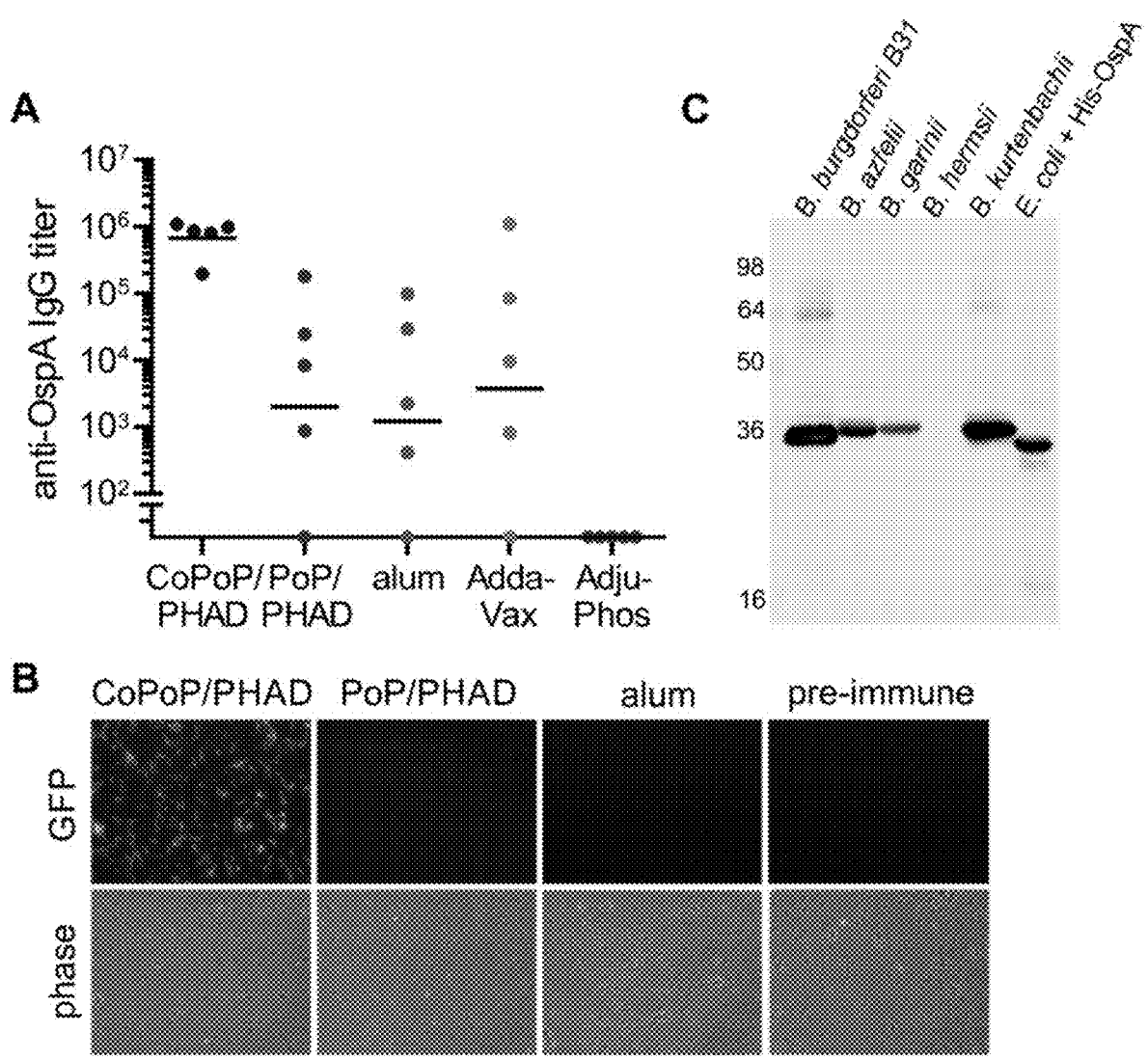
FIG. 25. Evaluation of the immunogenicity of OspA-based nanoliposomal vaccine. (A) Anti-OspA IgG titers induced by CoPoP/PHAD liposomes compared to other commercial adjuvants. Detection of anti-OspA IgG antibodies by (B) indirect immunofluorescence assay of permeabilized B. burgdorferi B31 using goat anti-Mouse IgG (H+L) secondary antibody DyLight® 488 conjugate and by (C) immunoblot assay using whole cell lysates of B. burgdorferi B31 and B. azfelii. Horizontal lines represent geometric mean.
Figure 26:
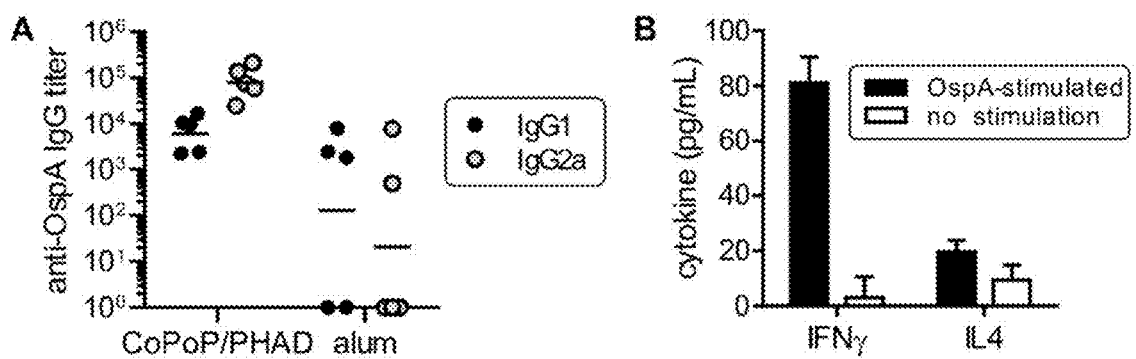
FIG. 26. Th1-biased immune response of OspA-bound CoPoP/PHAD liposomes. (A) IgG isotype profiling for post-immune sera (day 42) using ELISA. (B) Splenocyte stimulation study to detect interferon-gamma and interleukin-4 secretion after 72-hr stimulation with OspA. Error bars represent standard deviations from n=3 triplicate stimulation experiments. Horizontal lines indicate geometric mean.
Figure 27:
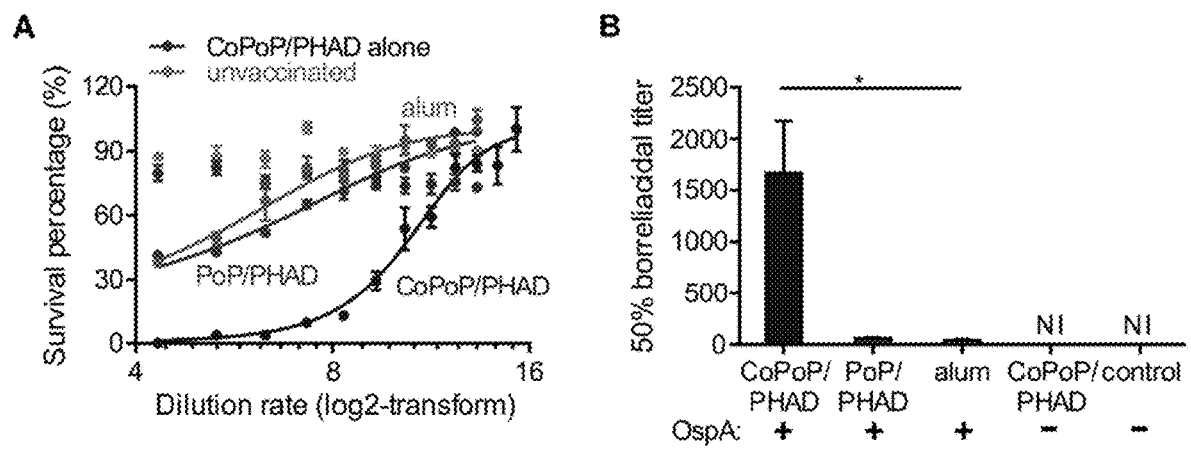
FIG. 27. Assessment of the borreliacidal activity of SNAP-induced OspA antibodies. (A) Serum bactericidal antibody assay performed using guinea pig complement. Survival percentage was derived from normalization of the number of spirochetes after overnight serum treatment to that immediately after incubation. Surviving B. burgdorferi B31-A3 were counted using dark-field microscopy. (B) Average 50% borreliacidal activity (serum dilution rate that effectively eliminated 50% of the bacteria) from three different mice sera. Error bars represent standard error of the mean. NI stands for no inhibition. Statistical significance ($p<0.05$, indicated by asterisks) of differences between bactericidal titers is assessed by Kruskal-Wallis test with Dunn's post-hoc.
Figure 28:
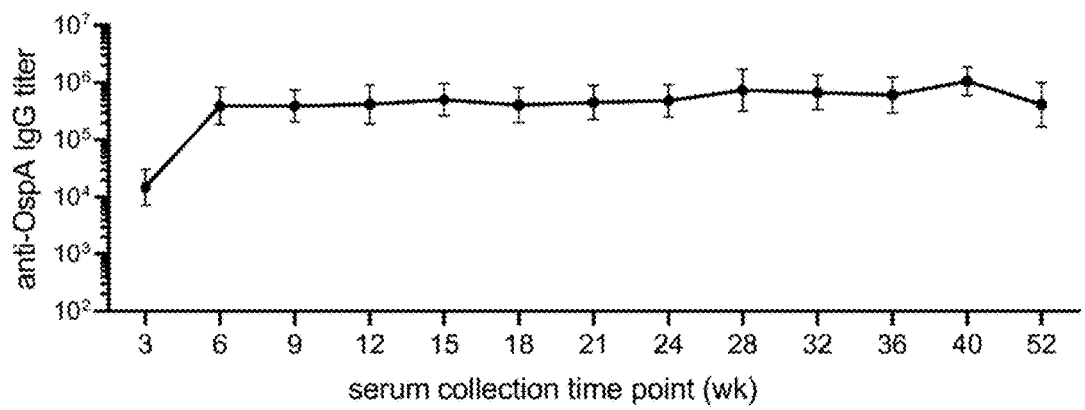
FIG. 28. Longevity of anti-OspA IgG levels in SNAP-immunized mice. Prime and boost vaccinations of 100 ng OspA with CoPoP/PHAD liposomes were administered on day 0 and 21, respectively. Endpoint titer is defined as the reciprocal of serum dilution at absorbance cut-off value of 0.5. Data points represent geometric mean and the error bars the 95% confidence interval.
Figure 29:
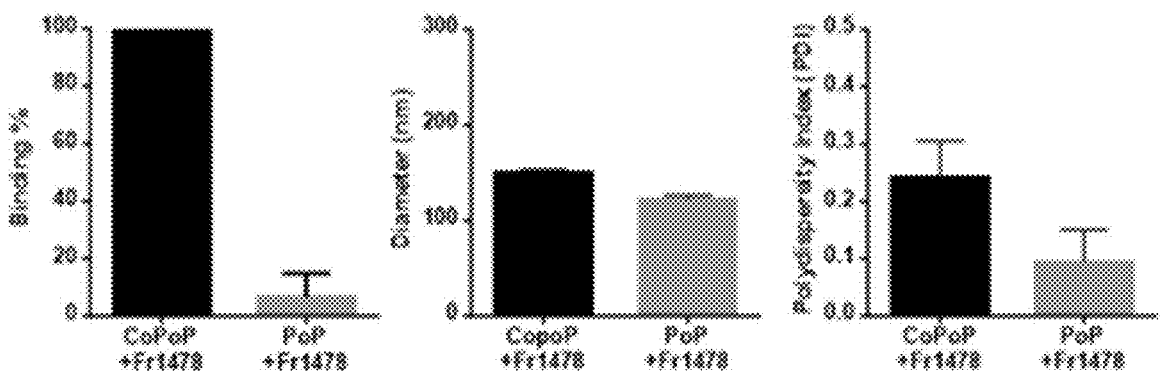
FIG. 29. Binding of his-tagged HA protein from H3N2 strain Fr1478 to CoPoP liposomes.
Figure 30:
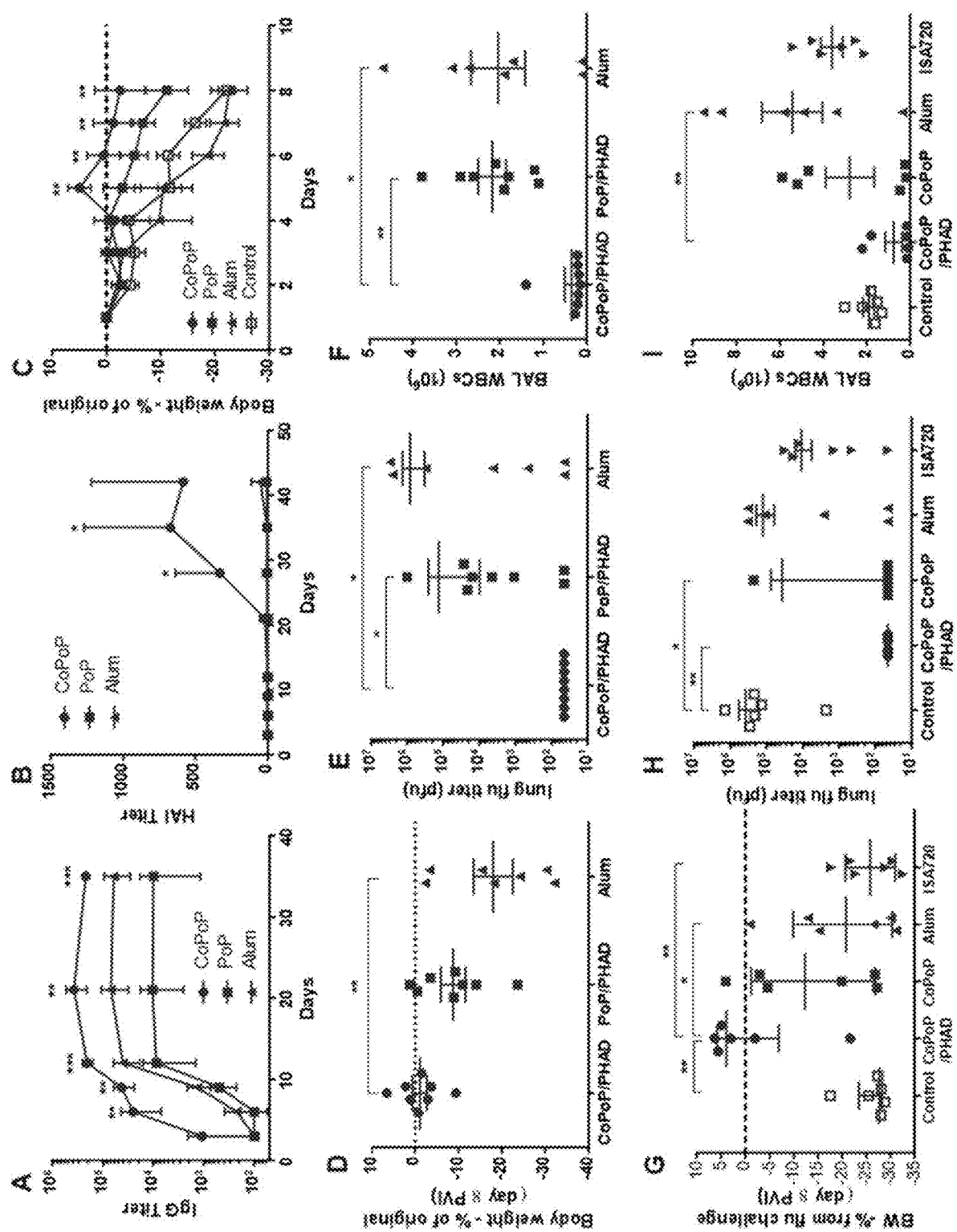
FIG. 30. Shown in (A-F), three groups of mice (n=8) were vaccinated with 100 ng of the H3 antigen Fr1478 (from flu strain A/canine/Illinois/11613/2015) adjuvated with CoPoP/MPLA, 2HPoP/MPLA, or Alum (aluminum hydroxide), and then inoculated with A/Hong Kong/1/1968. (A) The IgG ELISA and (B) HAI assays performed with serum samples taken throughout the vaccination period show that CoPoP/MPLA+Fr1478 particles achieve the best antibody response prior to viral challenge. (C-D) Body weight remained stable across the 8-day challenge period, and both (E) viral load and (F) white blood cell count in lung tissue were minimal in CoPoP vaccinated mice, indicating effective protection against the virus. (G-I) A follow-up challenge study was performed to investigate how CoPoP/MPLA protection compared to CoPoP without MPLA and another adjuvant, the montanide ISA720. Again, CoPoP/MPLA vaccinated mice exhibit the most consistent body weight retention and lowest viral load and white blood cell count in the lungs.
Figure 31:
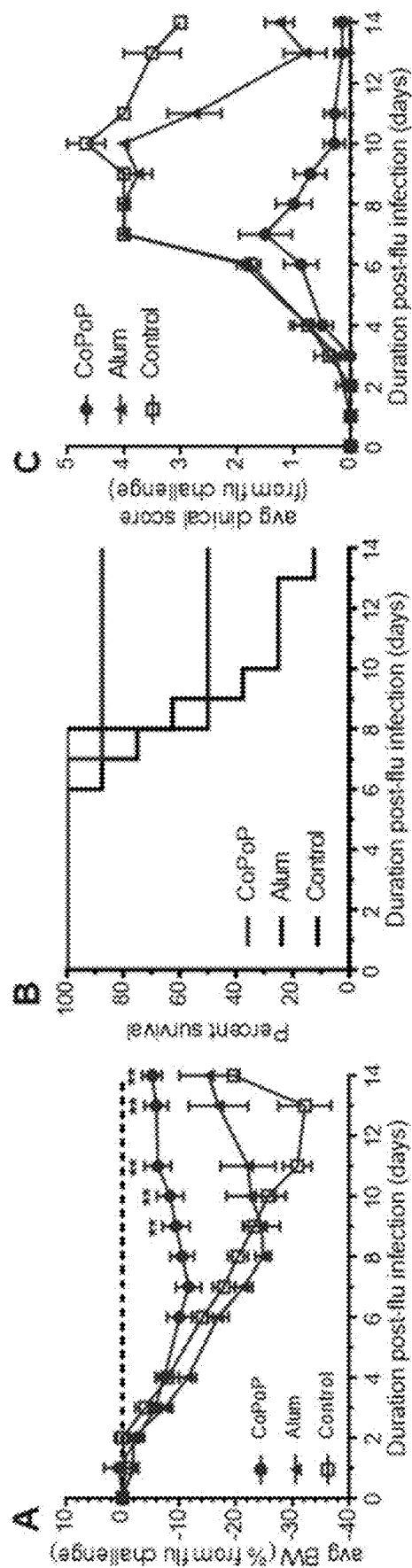
FIG. 31. While passive transfer of vaccinated mouse serum yields lower protection than direct vaccination, transfer of serum from mice vaccinated with CoPoP yields (A) significantly reduced weight loss, (B) a higher rate of survival, and (C) lower clinical scores. This data supports the hypothesis that the immune response resulting from CoPoP vaccination is significantly antibody-mediated.
Figure 32:
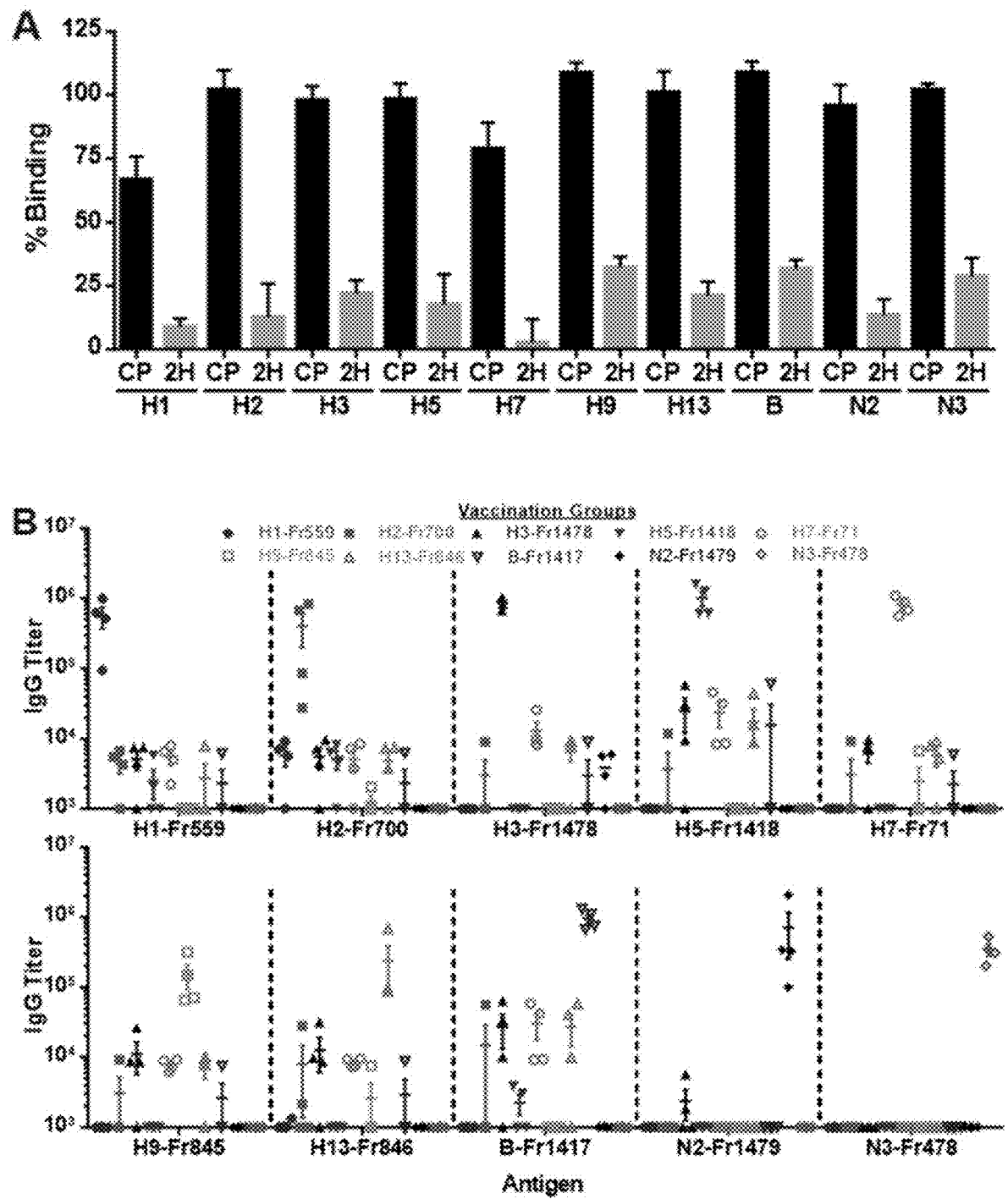
FIG. 32. Shown in (A), his-tagged influenza antigens from various subtypes were obtained and tested for binding affinity with CoPoP. The binding potential of his-tagged antigens appears to be independent of subtype, with most antigens achieving approximately 100% binding with CoPoP after 3 hours of incubation at room temperature. (B) Mice were vaccinated with CoPoP incubated with one of the ten selected antigens, and the serum was collected and ELISA was used to quantify the binding reactions of the resultant serum antibodies. Antibody reactions against the antigen that was homologous with the vaccine antigen resulted in the highest IgG binding, with the nonspecific binding of antibodies elicited by other subtypes tended to average one to two orders of magnitude lower binding.
Figure 33:
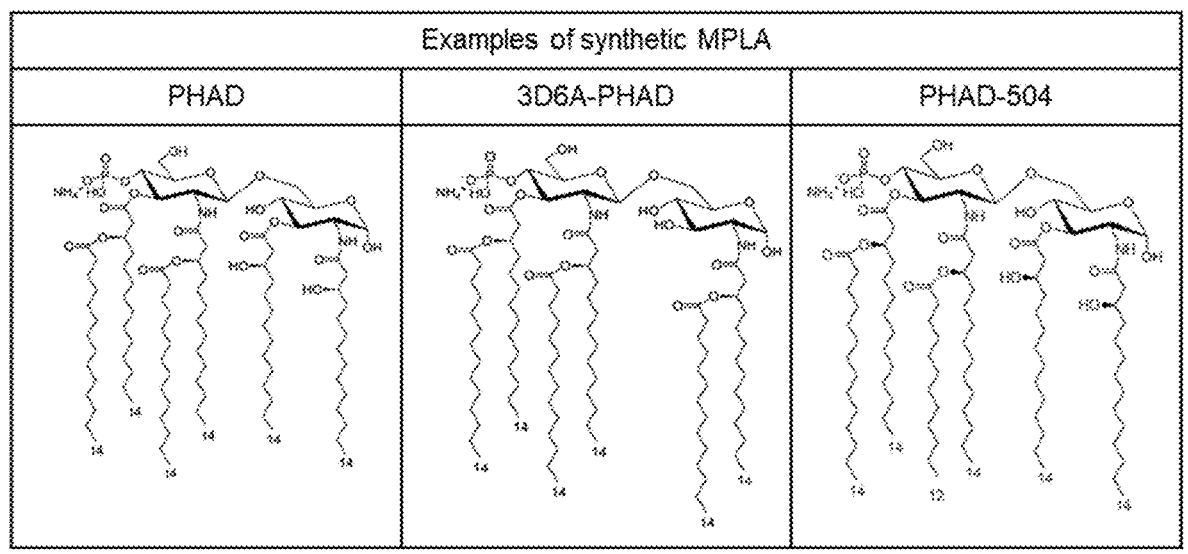
FIG. 33. Structures of some examples of synthetic adjuvants.
Figure 34:
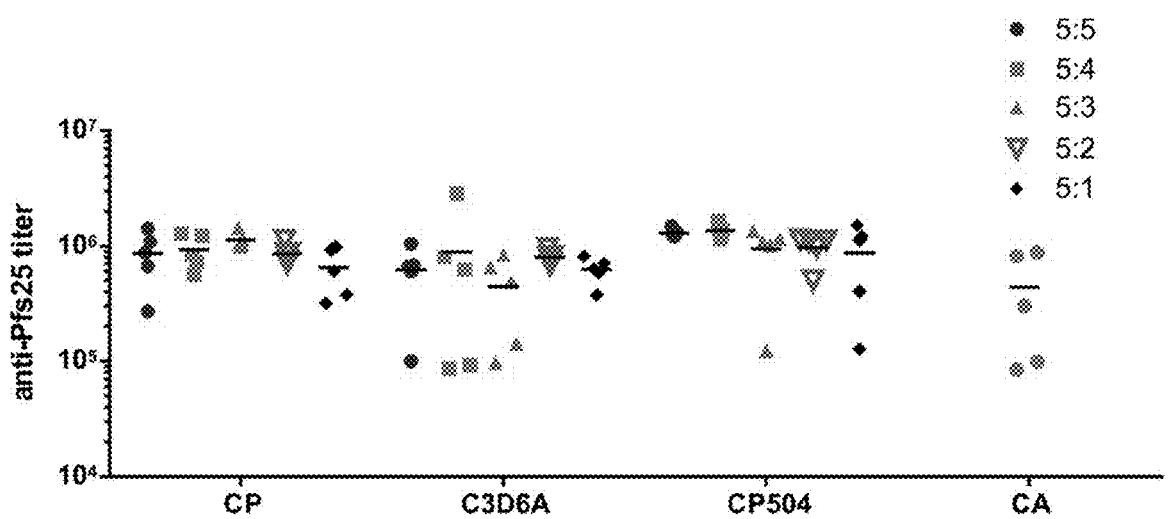
FIG. 34. Liposomes were formed with 4:2:1:X DPPC:Cholesterol:CoPoP:MPLA, where MPLA was each of these types of synthetic versions, and X varied was either 5,4,3, 2,1. Results are shown for anti-Pfs25 titer for CP (PHAD), C3D6A (3D6A-PHAD), CP504 (PHAD-504), and CA (no MPLA).

Serum stability study (FIG. 24A) showed that incubation of the proteoliposomes with human at 37° C. did not significantly increase the fluorescence signal after 12 days. This basically indicates that OspA remains mainly associated to the metallochelating liposomes within the duration of the study. CoPoP liposome exhibited more than a hundred-fold increase in stability compared to nickel-chelating liposomes due to the strategic spatial location of the metallo-chelating bond within the hydrophobic bilayer. Serum-stable antigen binding ensures integrity of the proteoliposomes during transit to draining lymph nodes.

Previous studies using analogous nanoparticle systems demonstrated variation of the immunogenicity and protective efficacy with the point of attachment to the nanoparticle scaffold. This highlights the importance of proper antigenic epitope presentation on the particle surface. In this study, polyhistidine tag was appended at the N-terminus opposite to the locality of protective epitopes to ensure epitope accessibility on the liposomal surface and avoid possible occlusion of the important C-terminal epitopes. This configuration basically mimics the lipoprotein integration to the outer membrane of Lyme borreliae. Assessment of the epitope availability using immunoprecipitation method indicated exposure of LA-2 epitope on the surface-bound OspA (FIG. 24B). The negative control, which is a monoclonal antibody for a non-homologous protein, exhibited low PoP fluorescence signal. These results indirectly corroborated findings in CD spectroscopy measurements, which elucidated the secondary structure of recombinant OspA. Furthermore, LA-2 antibody-OspA recognition suggested that structural integrity of the binding antigen is maintained after attaching to liposomes.

Practical utility of liposomes as antigen delivery vesicles is attributed from its enhanced uptake by antigen presenting cells. Nanoparticle internalization studies using murine macrophage-like cells (FIG. 24C) showed high antigen uptake only with the surface-functionalized liposome (CoPoP/PoP liposome). Minimal uptake was observed with the free non-adjuvanted or mixed non-associated (i.e., PoP/PHAD) forms of the antigen. These results corroborate studies demonstrating enhanced antigen internalization in the nanoparticulate form. The macrophage selective uptake of PoP/PHAD liposomes in the mixed form further implicates that physical association of antigen to liposomes may be necessary for liposomal adjuvanticity. Co-delivery of surface-exposed antigen and immunostimulant to immune cells is an important facet of the CoPoP/PHAD liposome. Cellular uptake mechanism via phagocytosis is supported by the diminished uptake for both antigen and liposome in the presence of cytochalasin B.

Assessment of the immunogenicity using ELISA indicates that this novel vaccine platform can stimulate strong immune response at low antigen dose. Homologous prime-boost vaccination with CoPoP/PHAD liposomes elicited OspA-specific IgG antibody titer higher than other commercial adjuvants (FIG. 25A). Furthermore, surface labeling of *B. burgdorferi* B31 cells (FIG. 25B) suggested that the generated OspA-specific antibodies can recognize epitopes on the cell surface, supporting results obtained from immunoprecipitation assay. Fluorescence micrographs further reveals low functionality of the anti-OspA antibodies induced from immunization with alum. Immunoblot using antisera from CoPoP/PHAD immunization showed that OspA-specific antibodies recognize different strains of Lyme borreliae but to different extents (FIG. 22C). Different band intensity depicts antigenic heterogeneity of OspA across different genospecies. The negative control, *B. hermsii*, which lacks the ospa gene, has no apparent band. Minimal non-specific bands were observed for *E. coli* lysate with histidine-tagged OspA. Lower molecular weight observed for the OspA band is due to the substitution of the lipidation signal sequence with a shorter polyhistidine segment.

Inclusion of the synthetic version of monophosphoryl lipid A, PHAD, which is a TLR-4 agonist, in the liposomal formulation skewed the immune response towards Th1, switching the isotype to IgG2a. CoPoP/PHAD liposomes produced higher levels of OspA-specific IgG2a antibodies than IgG1 (FIG. 23A). Alum, on the other hand, induced higher levels of IgG1 isotype. Predominance of IgG2a isotype is vital as this isotype exhibits higher bactericidal activity and greater capacity to activate complement than IgG1 isotype. The Th1-biased immune response observed for CoPoP/PHAD liposomes correlates with the higher stimulation of interferon-gamma than interleukin-4 in the splenocyte study (FIG. 23B).

The ability of OspA-specific antibodies to eradicate spirochetes was demonstrated using bactericidal assay. Generated antibodies from CoPoP/PHAD-OspA immunization exhibited higher bactericidal activity compared to alum or PoP/PHAD liposomes (FIG. 27). Calculated 50% borreliacidal titer for CoPoP/PHAD liposomes is significantly higher than alum.

An OspA-based transmission-blocking vaccine heavily relies on the high levels of circulating antibodies. ELISA titers calculated at different time points remained fairly the same after one year, indicating high durability of the antibody response in FIG. 28.

Example 8

In this example, CoPoP liposomes were used with hemagglutinin antigens and neuraminidase for influenza. His-tagged antigens can be used with the CoPoP/PHAD system for generating functional antibodies.

Influenza hemagglutinin (HA) is the major surface antigen on the flu virus and a major vaccine target. We obtained his-tagged H3 strain HA. As shown in FIG. 29, his-tagged HA bound effectively to CoPoP liposomes.

A 50 μL volume of antigen-liposome solution is prepared using CoPoP and PoP (also referred to as 2H) and diluted to 200 μL. Reference samples of liposomes without antigen, and antigen without liposomes, were also prepared. Samples were centrifuged at 20,000 rcf for 90 minutes, and the supernatant was extracted from the resulting liposome pellet. An equal volume of BCA was added, to a total volume of 400 μL. Samples were then incubated in a water bath at 60° C. for 10 minutes. A volume of 100 μL of each sample were transferred to each of 3 wells of a 96-well plate and the absorbance was measured at 562 nm. The absorbance difference between the antigen-liposome supernatant and liposome-only reference samples were used to calculate the percentage binding, with higher absorbance corresponding with a higher protein concentration in the supernatant and thus a lower binding.

As shown in FIG. 30, immunization with CoPoP liposomes and his-tagged HA was highly potent.

A passive serum transfer experiment established that the vaccine-mediated protection was at least in part due to antibody generation (FIG. 31).

The capacity for multiplexing was then assessed using multiple his-tagged HAs. As shown in FIG. 32A, various HA and NA proteins bound to CoPoP liposomes. When immunized, all the HAs could generate specific antibodies with minimal cross-reactivity (FIG. 32B).

Example 9

This example demonstrates that different types of synthetic MPLA can be used in the present compositions and methods, including PHAD, PHAD-504, and 3D6A-PHAD. The structures for these adjuvants are shown in FIG. 33. Liposomes were formed with 4:2:1:X DPPC:Cholesterol:CoPoP:MPLA, where MPLA was each of these types of synthetic versions, and X varied was either 5,4,3,2,1.

As shown in FIG. 34, inclusion of all types of MPLA could generate liposomes and result in antibody generation that was generally higher than omission of MPLA ("CA")

bleow. His-tagged Pfs25 was mixed in a 1:4 mass ratio of antigen:CoPoP and mice were immunized on day 0 and day 21. Serum was collected on day 42 and serum was assessed for Pfs25 binding IgG ELISA.

While the invention has been described through specific embodiments, routine modifications will be apparent to those skilled in the art and such modifications are intended to be within the scope of the present disclosure.

What is claimed is:

1. A liposome comprising:
    a) a bilayer, wherein the bilayer comprises:
        i) phospholipid, and
        ii) porphyrin having cobalt coordinated thereto forming cobalt-porphyrin; and
    b) a polyhistidine-tagged presentation molecule, wherein at least a portion of the polyhistidine tag resides in the hydrophobic portion of the monolayer or the bilayer and one or more histidines of the polyhistidine tag are coordinated to the cobalt in the cobalt-porphyrin, wherein at least a portion of the polyhistidine-tagged presentation molecule is exposed to the outside of the liposome and the polyhistidine-tagged presentation molecule comprises an epitope from a microorganism, and wherein the liposome encloses an aqueous compartment.

2. The liposome of claim 1, wherein the microorganism is a virus, bacteria, or parasite.

3. The liposome of claim 2, wherein the epitope is from respiratory syncytial virus (RSV), Borrelia burgdorferi or influenza virus.

4. The liposome of claim 3, wherein the epitope is from is DS-Cav1, OspA, hemagglutinin or neuraminidase.

5. The liposome of claim 1, wherein the cobalt porphyrin is conjugated to a phospholipid to form a cobalt porphyrin-phospholipid conjugate.

6. The liposome of claim 5, wherein the cobalt porphyrin-phospholipid conjugate makes up from 1 to 25 mol % of the monolayer or the bilayer.

7. The liposome of claim 6, wherein the cobalt porphyrin-phospholipid conjugate makes up from 5 to 10 mol % of the monolayer or bilayer.

8. The liposome of claim 1, wherein the bilayer further comprises cholesterol and/or phosphatidylserine.

9. The liposome of claim 1, wherein the polyhistidine-tag comprises 6 to 10 histidine residues.

10. The liposome of claim 1, wherein size of the liposome is 50 nm to 200 nm.

11. A nanostructure comprising:
   a) a core; and
   b) a monolayer or a bilayer on said core, wherein the monolayer or bilayer comprises:
      i) phospholipid monomers, and
      ii) porphyrin having cobalt coordinated thereto forming cobalt-porphyrin; and
   c) a polyhistidine-tagged presentation molecule comprising an epitope from a microorganism, wherein at least a portion of the polyhistidine tag resides in the hydrophobic portion of the monolayer or the bilayer, one or more histidines of the polyhistidine tag are coordinated to the cobalt in the cobalt-porphyrin, and at least a portion of the polyhistidine-tagged presentation molecule is exposed on the outside of the nanostructure.

12. The nanostructure of claim 11, wherein the core is a gold nanoparticle.

13. The nanostructure of claim 11, wherein the microorganism is a virus, bacteria or parasite.

14. The nanostructure of claim 11, wherein the epitope is from respiratory syncytial virus (RSV), Borrelia burgdorferi or influenza virus.

15. The nanostructure of claim 11, wherein the epitope is from DS-Cav1, OspA, hemagglutinin or neuraminidase.

16. A method for generating an immune response in a host individual comprising administering to the individual a composition comprising the liposomes of claim 1 in a pharmaceutical carrier, wherein the presentation molecule comprises an immunogenic epitope from a virus, bacteria or parasite.

17. The method of claim 16, wherein the epitope is from respiratory syncytial virus (RSV), Borrelia burgdorferi or influenza virus.

18. The method of claim 17, wherein the epitope is from is DS-Cav1, OspA, hemagglutinin or neuraminidase.

19. The method of claim 16, wherein the individual is a human or non-human animal.

20. The liposome of claim 1, wherein the monolayer or the bilayer further comprises an adjuvant.

21. The liposome of claim 20, wherein the adjuvant is an attenuated lipid A derivative or phosphorylated hexaacyl disaccharide.

* * * * *